US011471479B2

(12) United States Patent
Larson et al.

(10) Patent No.: US 11,471,479 B2
(45) Date of Patent: Oct. 18, 2022

(54) POLYSACCHARIDE AND NUCLEIC ACID FORMULATIONS CONTAINING VISCOSITY-LOWERING AGENTS

(71) Applicant: EAGLE BIOLOGICS, INC., Cambridge, MA (US)

(72) Inventors: Alyssa M. Larson, Dana Point, CA (US); Kevin Love, Boston, MA (US); Alisha K. Weight, Mill Creek, WA (US); Alan Crane, Waban, MA (US); Robert S. Langer, Newton, MA (US); Alexander M. Klibanov, Boston, MA (US)

(73) Assignee: Eagle Biologics, Inc., Cambridge, MA (US)

( * ) Notice: Subject to any disclaimer, the term of this patent is extended or adjusted under 35 U.S.C. 154(b) by 412 days.

(21) Appl. No.: 15/516,074

(22) PCT Filed: Sep. 30, 2015

(86) PCT No.: PCT/US2015/053313
§ 371 (c)(1),
(2) Date: Mar. 31, 2017

(87) PCT Pub. No.: WO2016/054259
PCT Pub. Date: Apr. 7, 2016

(65) Prior Publication Data
US 2018/0228831 A1 Aug. 16, 2018

Related U.S. Application Data

(60) Provisional application No. 62/058,123, filed on Oct. 1, 2014, provisional application No. 62/058,125, filed on Oct. 1, 2014, provisional application No. 62/058,122, filed on Oct. 1, 2014, provisional application No. 62/058,124, filed on Oct. 1, 2014.

(51) Int. Cl.
| A61K 31/727 | (2006.01) |
| A61K 31/721 | (2006.01) |
| A61K 9/08 | (2006.01) |
| A61K 9/19 | (2006.01) |
| A61K 9/00 | (2006.01) |
| A61K 45/06 | (2006.01) |
| A61K 31/715 | (2006.01) |
| A61K 31/7088 | (2006.01) |
| A61K 31/7105 | (2006.01) |
| A61K 31/713 | (2006.01) |
| A61K 31/722 | (2006.01) |
| A61K 31/724 | (2006.01) |
| A61K 31/728 | (2006.01) |
| A61K 31/734 | (2006.01) |
| A61K 31/737 | (2006.01) |
| A61K 47/26 | (2006.01) |
| A61K 47/36 | (2006.01) |

(52) U.S. Cl.
CPC ......... *A61K 31/727* (2013.01); *A61K 9/0019* (2013.01); *A61K 31/7088* (2013.01); *A61K 31/713* (2013.01); *A61K 31/715* (2013.01); *A61K 31/7105* (2013.01); *A61K 31/722* (2013.01); *A61K 31/724* (2013.01); *A61K 31/728* (2013.01); *A61K 31/734* (2013.01); *A61K 31/737* (2013.01); *A61K 45/06* (2013.01); *A61K 47/26* (2013.01); *A61K 47/36* (2013.01)

(58) Field of Classification Search
None
See application file for complete search history.

(56) References Cited

U.S. PATENT DOCUMENTS

| 3,682,174 A | 8/1972 | Cohen et al. |
| 4,092,410 A | 5/1978 | Ogata et al. |
| 4,171,698 A | 10/1979 | Genese |
| 4,816,567 A | 3/1989 | Cabilly |
| 5,001,000 A | 3/1991 | Rohrbacher et al. |
| 5,034,506 A | 7/1991 | Summerton et al. |
| 5,142,047 A | 8/1992 | Summerton et al. |
| 5,166,315 A | 11/1992 | Summerton et al. |
| 5,168,062 A | 12/1992 | Stinski |
| 5,217,866 A | 6/1993 | Summerton et al. |
| 5,334,162 A | 8/1994 | Harris |
| 5,356,802 A | 10/1994 | Chandrasegaran |
| 5,385,839 A | 1/1995 | Stinski |
| 5,436,150 A | 7/1995 | Srinivasan |
| 5,454,786 A | 10/1995 | Harris |

(Continued)

FOREIGN PATENT DOCUMENTS

| CN | 1483814 A | 3/2004 |
| CN | 1789575 A | 6/2006 |

(Continued)

OTHER PUBLICATIONS

Malvern, Bohlin CVO Rheological properties,2010, pp. 1-4.*

(Continued)

*Primary Examiner* — Maria Marvich
(74) *Attorney, Agent, or Firm* — BakerHostetler

(57) ABSTRACT

Concentrated, low-viscosity, low-volume liquid pharmaceutical formulations of polysaccharides and nucleic acids have been developed. Such formulations can be rapidly and conveniently administered by subcutaneous or intramuscular injection, rather than by lengthy intravenous infusion. These formulations include low-molecular-weight and/or high-molecular-weight polysaccharides and nucleic acids, and viscosity-lowering agents.

32 Claims, 3 Drawing Sheets

(56) References Cited

U.S. PATENT DOCUMENTS

| | | |
|---|---|---|
| 5,487,994 A | 1/1996 | Chandrasegaran |
| 5,506,337 A | 4/1996 | Summerton et al. |
| 5,521,063 A | 5/1996 | Summerton et al. |
| 5,527,675 A | 6/1996 | Coull et al. |
| 5,539,082 A | 7/1996 | Nielsen et al. |
| 5,569,193 A | 10/1996 | Hofstetter et al. |
| 5,608,038 A | 3/1997 | Eibl et al. |
| 5,623,049 A | 4/1997 | Lobberding et al. |
| 5,641,870 A | 6/1997 | Rinderknecht et al. |
| 5,698,195 A | 12/1997 | Le et al. |
| 5,698,685 A | 12/1997 | Summerton et al. |
| 5,714,331 A | 2/1998 | Buchardt et al. |
| 5,730,978 A | 3/1998 | Wayner |
| 5,736,137 A | 4/1998 | Anderson et al. |
| 5,736,336 A | 4/1998 | Buchardt et al. |
| 5,773,571 A | 6/1998 | Nielsen et al. |
| 5,779,668 A | 7/1998 | Grabenkort |
| 5,786,571 A | 7/1998 | Bethel et al. |
| 5,819,988 A | 10/1998 | Sawhney et al. |
| 5,819,998 A | 10/1998 | Chehebar |
| 5,821,337 A | 10/1998 | Carter et al. |
| 5,840,299 A | 11/1998 | Bendig et al. |
| 5,871,736 A | 2/1999 | Bruegger et al. |
| 5,962,405 A | 10/1999 | Seelich |
| 6,033,665 A | 3/2000 | Yednock |
| 6,054,297 A | 4/2000 | Carter et al. |
| 6,065,645 A | 5/2000 | Sawhney et al. |
| 6,171,586 B1 | 1/2001 | Lam et al. |
| 6,184,037 B1 | 2/2001 | Rolland et al. |
| 6,217,866 B1 | 4/2001 | Sela et al. |
| 6,235,883 B1 | 5/2001 | Jakobovits et al. |
| 6,252,055 B1 | 6/2001 | Relton |
| 6,267,958 B1 | 7/2001 | Andya et al. |
| 6,394,314 B1 | 5/2002 | Sawhney et al. |
| 6,443,612 B1 | 9/2002 | Keller |
| 6,457,609 B1 | 10/2002 | Keller |
| 6,525,102 B1 | 2/2003 | Chen et al. |
| 6,551,840 B2 | 4/2003 | Ono et al. |
| 6,564,972 B2 | 5/2003 | Sawhney et al. |
| 6,602,503 B1 | 8/2003 | Lobb et al. |
| 6,685,940 B2 | 2/2004 | Andya et al. |
| 6,698,622 B2 | 3/2004 | Sawhney et al. |
| 6,730,328 B2 | 5/2004 | Maskiewicz et al. |
| 6,875,432 B2 | 4/2005 | Liu et al. |
| 6,994,869 B1 * | 2/2006 | Bird ................ A23L 33/40 |
| | | 424/439 |
| 7,030,097 B1 | 4/2006 | Saltzman et al. |
| 7,390,786 B2 | 6/2008 | Warne et al. |
| 7,501,000 B2 | 3/2009 | Rosenflanz et al. |
| 7,666,413 B2 | 2/2010 | Liu et al. |
| 7,740,842 B2 | 6/2010 | Arvinte et al. |
| 7,758,860 B2 | 7/2010 | Warne et al. |
| 8,142,776 B2 | 3/2012 | Liu et al. |
| 8,383,114 B2 | 2/2013 | Sloey et al. |
| 8,476,239 B2 | 7/2013 | Dali et al. |
| 8,500,681 B2 | 8/2013 | Gonnelli et al. |
| 8,703,126 B2 | 4/2014 | Liu et al. |
| 8,715,651 B2 | 5/2014 | Maestro et al. |
| 8,779,094 B2 | 7/2014 | Johnston et al. |
| 8,802,095 B2 | 8/2014 | Houston et al. |
| 8,906,368 B2 | 12/2014 | Bolli et al. |
| 8,936,827 B2 * | 1/2015 | Pacetti |
| 9,072,668 B2 | 7/2015 | Dai et al. |
| 9,084,743 B2 | 7/2015 | Feschner et al. |
| 9,084,777 B2 | 7/2015 | Morichika et al. |
| 9,309,316 B2 | 4/2016 | Dali et al. |
| 9,320,797 B2 | 4/2016 | Sloey et al. |
| 9,457,089 B2 | 10/2016 | Soula |
| 9,605,051 B2 | 3/2017 | Soane et al. |
| 9,669,242 B2 | 6/2017 | Chen et al. |
| 9,677,061 B2 | 6/2017 | Bookbinder et al. |
| 9,771,427 B2 | 9/2017 | Hofer et al. |
| 2002/0169120 A1 | 11/2002 | Blanchat et al. |
| 2002/0190082 A1 | 12/2002 | Keller |
| 2003/0113316 A1 | 6/2003 | Kaisheva et al. |
| 2004/0191243 A1 | 9/2004 | Chen et al. |
| 2004/0197324 A1 | 10/2004 | Liu et al. |
| 2004/0247672 A1 | 12/2004 | Tracy et al. |
| 2005/0019337 A1 * | 1/2005 | Ryall ................. A61K 39/095 |
| | | 424/184.1 |
| 2005/0158303 A1 | 7/2005 | Liu et al. |
| 2006/0142234 A1 | 6/2006 | Chen et al. |
| 2007/0053900 A1 | 3/2007 | Liu et al. |
| 2007/0065373 A1 * | 3/2007 | Morton ................. A61K 9/0073 |
| | | 424/46 |
| 2007/0093462 A1 | 4/2007 | Rogers et al. |
| 2007/0172479 A1 | 7/2007 | Warne et al. |
| 2007/0172497 A1 | 7/2007 | Atassi |
| 2007/0172517 A1 | 7/2007 | Ben-Sasson et al. |
| 2007/0184084 A1 * | 8/2007 | Chen ................... A61K 9/0024 |
| | | 424/422 |
| 2008/0071063 A1 | 3/2008 | Allan et al. |
| 2008/0226689 A1 | 9/2008 | Berry et al. |
| 2008/0248991 A1 | 10/2008 | Dyer et al. |
| 2009/0280129 A1 | 11/2009 | Liu et al. |
| 2010/0061949 A1 | 3/2010 | Schmidt-Jacobsen et al. |
| 2010/0136062 A1 | 6/2010 | Fernandez et al. |
| 2010/0239567 A1 | 9/2010 | Esue |
| 2010/0297106 A1 * | 11/2010 | Sloey et al. |
| 2011/0065675 A1 | 3/2011 | Buchwald et al. |
| 2011/0145940 A1 | 6/2011 | Voytas et al. |
| 2011/0212094 A1 | 9/2011 | Ghayur et al. |
| 2011/0262626 A1 | 10/2011 | Sun et al. |
| 2011/0305734 A1 | 12/2011 | Edelson et al. |
| 2012/0148556 A1 | 6/2012 | Lebowitz et al. |
| 2012/0230982 A1 | 9/2012 | Zhou et al. |
| 2012/0231009 A1 | 9/2012 | Ramani et al. |
| 2012/0263783 A1 | 10/2012 | Messmer |
| 2013/0028907 A1 * | 1/2013 | Parshad ............ A61K 39/39591 |
| | | 424/143.1 |
| 2013/0028920 A1 | 1/2013 | Gumy et al. |
| 2013/0058958 A1 | 3/2013 | Bowen et al. |
| 2013/0171128 A1 | 7/2013 | Huang et al. |
| 2013/0216525 A1 | 8/2013 | Chen |
| 2013/0216556 A1 | 8/2013 | Fowler et al. |
| 2013/0309226 A1 | 11/2013 | Armstrong et al. |
| 2013/0317457 A1 | 11/2013 | Schmitt et al. |
| 2014/0023655 A1 | 1/2014 | Monck et al. |
| 2014/0127227 A1 | 5/2014 | Chang |
| 2014/0127727 A1 | 5/2014 | Morikawa et al. |
| 2014/0277070 A1 * | 9/2014 | Otero et al. |
| 2014/0294859 A1 | 10/2014 | Sloey et al. |
| 2014/0378370 A1 | 12/2014 | Johnston et al. |
| 2014/0378655 A1 | 12/2014 | Anderson |
| 2015/0044198 A1 | 2/2015 | Liu et al. |
| 2015/0071920 A1 | 3/2015 | Larson et al. |
| 2015/0071925 A1 * | 3/2015 | Larson ................. A61K 39/3955 |
| | | 424/134.1 |
| 2015/0150979 A1 | 6/2015 | Yates et al. |
| 2015/0209431 A1 | 7/2015 | Ma et al. |
| 2015/0225485 A1 | 8/2015 | Liu et al. |
| 2015/0284466 A1 | 10/2015 | Morichika et al. |
| 2015/0337303 A1 * | 11/2015 | Crooke ................. C12N 15/113 |
| | | 514/44 A |
| 2016/0002624 A1 * | 1/2016 | Dibble .................. C12N 15/111 |
| | | 514/44 A |
| 2016/0074515 A1 | 3/2016 | Soane et al. |
| 2016/0090419 A1 | 3/2016 | Morichika et al. |
| 2016/0193346 A1 | 7/2016 | Houston et al. |
| 2016/0367675 A1 | 12/2016 | Liu et al. |
| 2017/0049888 A1 | 2/2017 | Liu et al. |

FOREIGN PATENT DOCUMENTS

| | | |
|---|---|---|
| CN | 1798575 | 7/2006 |
| CN | 101061185 | 10/2007 |
| CN | 102573459 A | 7/2012 |
| EP | 1981824 A2 | 10/2008 |
| EP | 2335725 A1 | 6/2011 |
| EP | 2538973 A2 | 1/2013 |
| GB | 750373 | 12/1953 |
| GB | 1231494 | 5/1971 |
| JP | 03-190823 A | 8/1991 |

(56) References Cited

FOREIGN PATENT DOCUMENTS

| | | | |
|---|---|---|---|
| JP | 08-173533 A | 7/1996 | |
| JP | 2003-129666 A | 5/2003 | |
| JP | 2004-002429 A | 1/2004 | |
| JP | 2006-523461 | 10/2006 | |
| JP | 2007-523050 | 8/2007 | |
| JP | 2009-511497 | 3/2009 | |
| JP | 2010-505773 | 2/2010 | |
| JP | 2010-124827 A | 6/2010 | |
| JP | 2013-509189 A | 3/2013 | |
| JP | 2013-525484 | 6/2013 | |
| JP | 2013-528570 | 7/2013 | |
| JP | 2015-508774 A | 3/2015 | |
| RU | 2485133 | 6/2013 | |
| WO | WO 1990014846 | * | 12/1990 |
| WO | WO 199505163 | * | 2/1995 |
| WO | 99/18994 A1 | 4/1999 | |
| WO | WO0244321 A2 | 6/2002 | |
| WO | 2002/092014 A2 | 11/2002 | |
| WO | 2003/101479 | 12/2003 | |
| WO | 2004/092361 A1 | 10/2004 | |
| WO | WO2004089335 A2 | 10/2004 | |
| WO | WO2006071693 A2 | 7/2006 | |
| WO | WO2007088110 A2 | 8/2007 | |
| WO | 2007/138014 A1 | 12/2007 | |
| WO | WO2008092084 A2 | 7/2008 | |
| WO | WO2009015367 A2 | 1/2009 | |
| WO | WO2009026122 A1 | 2/2009 | |
| WO | WO2009043049 A2 | 4/2009 | |
| WO | WO 2009052323 | * | 4/2009 |
| WO | 2009/120684 | 10/2009 | |
| WO | 2009/141397 | 11/2009 | |
| WO | WO 2010056657 | * | 5/2010 |
| WO | WO2010132047 A1 | 11/2010 | |
| WO | WO2011104381 A2 | 1/2011 | |
| WO | WO2011069037 A2 | 6/2011 | |
| WO | WO2011072246 A2 | 6/2011 | |
| WO | WO2011095543 A1 | 8/2011 | |
| WO | 2011/116090 | 9/2011 | |
| WO | WO2011109415 A2 | 9/2011 | |
| WO | WO2011139718 A1 | 11/2011 | |
| WO | WO2012010832 A1 | 1/2012 | |
| WO | WO2012141978 A2 | 10/2012 | |
| WO | WO 2012155035 | * | 11/2012 |
| WO | 2013/063275 | 5/2013 | |
| WO | WO2013096791 A1 | 6/2013 | |
| WO | 2013/112986 A1 | 8/2013 | |
| WO | 2013/123114 A2 | 8/2013 | |
| WO | WO2013176772 A1 | 11/2013 | |
| WO | WO2014018423 A2 | 1/2014 | |
| WO | WO2014023816 A1 | 2/2014 | |
| WO | 2015/038777 | 3/2015 | |
| WO | 2015/038782 | 3/2015 | |
| WO | 2015/038811 | 3/2015 | |
| WO | 2015/038818 | 3/2015 | |

OTHER PUBLICATIONS

Livak-Dahl, E. Droplet- and Bead-Based Microfluidic Technologies for Rheological and Biochemical Analysis, PhD thesis, 2013, pp. 1-133.*
Brookfield Ametek, More Solutions to Sticky Problems, pp. 1-62, downloaded Mar. 2, 2020.*
Papalamprou et al, Effect of medium molecular weight xanthan gum in rheology and stability of oil-in-water emulsion stabilized with legume proteins, J Sci Food Agric 85:1967-1973 (2005).*
Showing Compound Sodium alginate (FDB019541), p. 1-5, downloaded Mar. 2, 2020.*
Kinematic Viscosity, 1 page, downloaded Mar. 2, 2020.*
TA Instruments REhometers, Manual, pp. 1-14, downloaded Mar. 2, 2020.*
Solomon and Vanapalli, Multiplexed microfluidic viscometer for high-throughput complex fluid rheology, Microfluid Nanofluid (2014) 16:677-690.*
Brookfield, More Solutions to Sticky Problems, Jul. 30, 2014, pp. 1-59.*
Adler, M, Challenges in the Development of Pre-filled Syringes for Biologies from a Formulation Scientist's Point of View, American Pharmaceutical Review<b>, 2012, pp. 1-8 </b>.*
Schneider et al., A Study of the Osmolality and pH of Subcutaneous Drug Infusion Solutions, Australian Journal of Hospital Pharmacy, 1997, 29-31.*
SIDS Initial Assessment Report, Glycerol CAS No. 56-81-5, 2002, pp. 1-178.*
Inwood, M.J. (Arch Intern Med, 1993, p. 263; see entire document).*
"Guideline on Non-Clinical and Clinical Development of Similar Biological Medicinal Products Containing Low-Molecular-Weight-Heparins", European Medicines Agency, Nov. 10, 2016, 8 pages.
"Guideline on Similar Biological Medicinal Products Containing Biotechnology-Derived Proteins as Active Substance Duality Issues", European Medicines Agency, Feb. 22, 2006, 8 pages.
Baker et al., "Fluorescence Quenching Immunoassay Performed in an Ionic Liquid" Chem. Commun., 2006, pp. 2851-2853.
Roy et al., "Effect of Hydrotropes on Solution Behaviour of Amphiphiles" Current Science, vol. 85, No. 8, Oct. 25, 2003, pp. 1148-1155.
Bernstein, et al., "Role for a Bidentate Ribonuclease in the Initiation Step of RNA Interference", Nature, Jan. 2001, 109, pp. 363-366.
Braasch, et al., "Locked Nucleic Acid (LNA): Fine-Tuning the Recognition of DNA and RNA" Chem. Biol., Jan. 2001 8(1), pp. 1-7.
Carnes et al., "Plasmid DNA Manufacturing Technology", Recent Patents on Biotechnology, 2007, pp. 1-16.
Cermak et al., "Efficient Design and Assembly of Custom TALEN and other TAL Effector-Based Constructs for DNA Targeting" Nucleic Acids Research Jul. 2011, 15 Pages.
Chattopadhyay, "Aqueous Behaviour of Chitosan", International Journal of Polymer Science, 2010, pp. 1-7.
Arias et al., "Changes in the Flow Properties of Phospholipid Dispersions Induced by Procaine Dydrochloride. Effect of pH and Temperature" II Farmaco, vol. 56, Jul. 1, 2001, pp. 533-539.
Cong, "Multiplex Genome Engineering Using CRISPR/Cas Systems", Science, Feb. 15, 2013, pp. 819-823.
Du et al., "Hdrophobic Salts Markedly Diminish Viscosity of Concentrated Protein Solutions" Biotechonology Bioengineering, Mar. 2011, pp. 632-636.
Earle, "Ionic Liquids. Green Solvents for the Future" Pure Appl. Chem., 2000, 72(7) pp. 1391-1398.
Elbashir, "Duplexes of 21-Nucleotid RNAs Mediate RNA Interference in Cultured Mammalian Cells", Nature, 2001, 411, pp. 494-498.
Elbashir, "RNA Interference is Mediated by 21- and 22-Nucleotide RNAs", Genes Dev., 2001 15, pp. 188-200.
Ernst, "From Carbohydrate Leads to Glycomimetic Drugs", Nature Reviews Drug Discovery, 2009, 8, pp. 661-677
Fire, "Potent and Specific Genetic Interference by Double-Stranded RNA in Caenorhabditis Elegans", Nature, 1998, 391, pp. 806-811.
Guo et al., "Structure-Activity Relationship for Hydrophobic Salts as Viscosity-Lowering Excipients for Concentrated Solutions of Monoclonal Antibodies" Pharm Res, 2012, 29, pp. 3102-3109.
Palek et al., "Effect of Procaine HCLI on ATP: Calcium-Dependent Alterations in Red Cell Shape and Deformability" Blood, Jul. 1977, 50(1), pp. 155-164.
Hammond, "An RNA-Directed Nuclease Mediates Post-Transcriptional Gene Silencing in *Drosophila* Cells", Nature, 2000, 404, pp. 293-296.
Hannon, "RNA Interference" Nature, Jul. 11, 2001, vol. 418, pp. 244-251.
Harada et al., "Chemical Structure of Antithrombin-active Rhamnan Sulfate from Monostrom Nitidum", Bioscience, Biotechnology, and Biochemistry, 1998, 62(9), pp. 1647-1652.
Hawe et al., "Fluorescent Molecular Rotors as Dyes to Characterize Polysorbate-Containing IgG Formulations" Pharmaceutical Research, vol. 27, No. 2, Feb. 2010, pp. 314-326.

(56) References Cited

OTHER PUBLICATIONS

Jacobsen et al., "1,1-Dicyano-2-[6-(Dimethylamino)naphthalen-2-yl]propene(DDNP): A Solvent Polarity and Viscosity Sensitive Fluorophore for Fluorescene Microscopy", J. Am. Chem. Soc., 1996, 118, pp. 5572-5579.
Jezek et al., "Viscosity of Concentrated Therapeutic protein Compositions" Advanced Drug Delivery Reviews, 2011, pp. 1107-1117.
Jinek, et al., "A Programmable Dual-RNA-Guided DNA Endonuclease in Adaptive Bacterial Immunity" Science, Aug. 17, 2012, vol. 337, pp. 816-821.
Kim et al., "Chimeric Restriction Endonuclease", Proc. Natl. Acad. Sci. USA, Feb. 1994, pp. 883-887.
Kim et al., "Insertion and Deletion Mutants of FokI Restriction Endonuclease" J. Biol. Chem. Dec. 16, 1994, pp. 31978-31982.
Larson, "Bulky Polar Additives That Greatly Reduce the Viscosity of Concentrated Solutions of Therapeutic Monoclonal Antibodies", Journal of Pharmaceutical Sciences, 2017 pp. 1211-1217.
Li et al., "Alteration of the Cleavage Distance of Fok I Restriction Endonuclease by Insertion Mutagenesis" Proc. Natl. Acad. Sci. USA, Apr. 1993, pp. 2764-2768.
Li et al., "Functional Domains in Fok I Restriction Endonuclease" Proc., Natl. Acad. Sci. USA, May 1992, pp. 1275-4279.
Mallin, "Properties of Contractile Protein from Bovine Carotid Artery" J. Cell, and Comp. Physiol., Jun. 1965, pp. 355-360.
Martinez et al., "Single-Stranded Antisense siRNAs Guide Target RNA Cleavage in RNAi" Cell, Sep. 6, 2002, pp. 563-574.
Miller et al., "A TALE Nuclease Architecture for Efficient Genome Editing" Nature Biotechnol, Feb. 2011, 8 Pages.
Napoli et al., "Introduction of a Chimeric Chaicone Synthase Gene Into Petunia Results in Reversible Co-Suppression of Homologous Genes in Trans", 1990, Plant Cell, pp. 279-289.
Nykanen et al., "ATP Requirements and Small Interfering RNA Structure in the RNA Interference Pathway" Cell, vol. 107, Nov. 2, 2001, pp. 309-321.
Patel, Therapeutic Importance of Sulfated Polysaccharides From Seaweeds: Updating the Recent Findings. 3 Biotech, 2012, pp. 171-185.
Pathak et al., "Do Clustering Monoclonal Antibody Solutions Really Have a Concentration Dependence of Viscosity?", Biophysical Journal, vol. 104, Feb. 2013, pp. 913-923.
Van Rantwijk et al., "Biocatalysis in Ionic Liquids" Chem. Rev., 2007, 107, pp. 2757-2785.
Remington: "The Science and Practice of Pharmacy", 20th Edition, Alfonso R. Gennaro, Ed., Lippincott Williams & Wilkins, Copyright 2000, 18 Pages.
Riduan et al., "Imidazolium Salts and Their Polymeric Materials for Biological Applications" Chem. Soc. Rev., 2013 42, pp. 9055-9070.
Sheldon et al., "Biocatalysis in Ionic Liquids" Green Chem., 2012, 4, pp. 147-151.
Shire et al., "Challenges in the Development of High Protein Concentration Formulations" Journal of Pharmaceutical Sciences, Jul. 2004, vol. 93, pp. 1390-1402.
Smith et al., "Nucleic Acid Nanostructures for Biomedical Applications", Nanomedicine, 2013, pp. 105-121.
Srinivasan et al., "Non-Aqueous Suspensions of Antibodies are Much Less Viscous Than Equally Concentrated Aqueous Solutions" Pharm Res, 2013, 30, pp. 1749-1757.
Stirchak et al., "Uncharged Stereoregular Nucleic Acid Analogues. 1. Synthesis of a Cytosine-Continaing Oligomer with Carbamate Intemucleoside Linkages" Organic. Cherm., 1987, pp. 4202-4206.
Tzianabos, "Polysaccharide Immunomodulators as Therapeutic Agents: Structural Aspects and Biologic Function" Clinical Microbiology Reviews, Oct. 2000, pp. 523-533.
Ui-Tei et al., "Sensitive Assay of RNA Interference in *Drospohila* and Chinese Hamster Cultured Cells Using Firefly Luciferase Gene as Target", FEBS letters 479, 2000, pp. 79-82.
Vazquez-Rey, Aggregates in Monoclonal "Antibody Manufacturing Processes" Biotechnology and Bioengineering, Jul. 2011, vol. 108, No. 7., pp. 1494-1508.

Wang et al., "Antibody Structure, Instability, and Formulation" Journal of Pharmaceutical Sciences, vol. 96, Jan. 2007, pp. 1-26.
Wasser et al., "Therapeutic Effects of Substances Occurring in Higher Basidiomycetes Mushrooms: A Modern Perspective" Critical Reviews in Immunology, 1999, 19, pp. 65-96.
Kivitz et al., "Clinical Assessment of Pain, Tolerability, and Preference of an Autoinjection Pen Versus a Prefilled Syringe for Patient Self-Administration of the Fully Human, Monoclonal Antibody Adalimumab: The TOUCH Trial" Clinical Therapeutics, Nov. 10, 2006, vol. 28, pp. 1619-1629.
Miller et al., "Low Viscosity Highly Concentrated Injectable Nonaqueous Suspensions of Lysozyme Microparticles", Langmuir, Jan. 19, 2010, pp. 1067-1074.
Wei Du et al.: "Hydrophobic salts markedly diminish viscosity of concenlialed protein solutions", Biotechnology and Bioengineering, vol. 108, No. 3, Nov. 17, 2010 (Nov. 17, 2010), pp. 632-636, XP055154925.
Kyoko Fujita et al: "Solubility and stability of cytochrome c in hydrated ionic liquids: effect of oxo acid residues and kosmotropicity", Biomacromolecules, American Chemical Society, US, vol. 8, Jan. 1, 2007, pp. 2080-2086, XP002667673.
Daugherty Ann L et al.: "Chapter 8: Formulation and delivery issues for monoclonal antibody therapeutics", Jan. 1, 2010 (Jan. 1, 2010), Current Trends in Monoclonal Antibody Development and Manufacturing, Springer, US, pp. 103-129, XP009180430.
Ayala Rosanne S et al: "The addition of injectable lidocaine to adalimumab results in decreased injection site pain and increased acceptance of therapy", Arthritis & Rheumatism, Wiley Interscience, US, vol. 58, No. 9, Suppl. S, Aug. 31, 2008 (Aug. 31, 2008), p. S858, XP009505904.
Zapata et al. , Engineering linear F (ab') 2 fragments for efficient production in *Escherichia coli* and enhanced antiproliferative activity. Protein Engineering, Design and Selection. Oct. 1, 1995;8(10):1057-1062.
Yip et al., Therapeutic value of glycosaminoglycans in cancer, Molecular cancer therapeutics 5.9, Sep. 2006, 2139-2148.
Wang, Monoclonal antibody pharmacokinetics and pharmacodynamics. Clinical Pharmacology & Therapeutics. Nov. 1, 2008;84(5):548-558.
Sutherland, Biotechnology of microbial exopolysaccharides, Cambridge University Press; 1990, pp. 70-88.
Scolnik, mAbs: a business perspective. InMAbs Mar. 1, 2009 (vol. 1, No. 2, pp. 179-184). Taylor & Francis.
Reichmann et al., Reshaping human antibodies for therapy, Nature 332:323-329,1988.
Reichert, Which are the antibodies to watch in 2013?. InMAbs Jan. 1, 2013 (vol. 5, No. 1, pp. 1-4). Taylor & Francis.
Presta, Antibody engineering. Current Opinion in Structural Biology. Aug. 1, 1992;2(4):593-596.
Pearlman, Peptide and Protein Drug Delivery, 247-301, Vincent Lee, Ed., Marcel Dekker, Inc., New York, N.Y. (1991).
Page, Heparin and related drugs: beyond anticoagulant activity, ISRN pharmacology, 2013, 14 pages.
Ober et al., Differences in promiscuity for antibody-FcRn interactions across species: implications for therapeutic antibodies. International immunology Dec. 1, 2001;13(12):1551-1559.
Morrison et al., Chimeric antibody molecules: mouse antigen-binding domains with human constant region domains. Proceedings of the National Academy of Sciences. Nov. 1, 1984;81(21):6851-6855.
Marks et al., By-passing immunization: human antibodies from V-gene libraries displayed on phage. Journal of molecular biology. Dec. 5, 1991;222(3):581-597.
Lee, Changing needs in drug delivery in the era of peptide and protein drugs. Peptide and protein drug delivery. 1991;1:1-56.
Köhler, Continuous cultures of fused cells secreting antibody of predefined specificity. Nature. Aug. 1975;256(5517):495-497.
Kerr, The use of cylexin (CY-1503) in prevention of reperfusion lung injury in patients undergoing pulmonary thromboendarterectomy, American journal of respiratory and critical care medicine, Jul. 1, 2000;162(1): 14-20.

(56) References Cited

OTHER PUBLICATIONS

Jones, Replacing the complementarity-determining regions in a human antibody with those from a mouse. Nature. May 1986;321(6069):522-525.

Jones, Analysis of polypeptides and proteins. Advanced drug delivery reviews. Jan. 1, 1993; 10(1):29-90.

Hoffman, Conjugates of stimuli-responsive polymers and proteins. Progress in Polymer Science. Aug. 1, 2007;32(8-9):922-932.

Federici, Analytical lessons learned from selected therapeutic protein drug comparability studies. Biologicals. May 1, 2013;41(3):131-147.

Daugherty, Formulation and delivery issues for monoclonal antibody therapeutics. Advanced drug delivery reviews. Aug. 7, 2006;58(5-6):686-706.

Clackson et al., Making antibody fragments using phage display libraries. Nature. Aug. 1991; 352, 624-628.

Buss, Monoclonal antibody therapeutics: history and future. Current opinion in pharmacology. Oct. 1, 2012;12(5):615-622.

Beck, Biosimilar, biobetter and next generation therapeutic antibodies. InMAbs Mar. 1, 2011 (vol. 3, No. 2, pp. 107-110). Taylor & Francis.

Baumann, Early development of therapeutic biologics-pharmacokinetics. Current drug metabolism. Jan. 1, 2006;7(1):15-21.

Accessdata FDA, ref. 4407872, p. 1-7.

Costantini et al., Effects of Overdose of High-Dose thiamine treatments, Gerentology and Geriatric Studies, vol. 4, p. 389-390, 2018.

FDA Report, Clinical Pharmacology and Biopharmaceutics Review for Tagamet, p. 1-33, 1998.

Soares, G. A. et a l., "Effect of drying technique on some physical properties of cross-linked high amylose/pectin mixtures", Drug Development and Industrial Pharmacy, 2013, 39(2), pp. 284-289.

* cited by examiner

POLYSACCHARIDE AND NUCLEIC ACID FORMULATIONS CONTAINING VISCOSITY-LOWERING AGENTS

CROSS-REFERENCE TO RELATED APPLICATIONS

This application is the National Stage Application of International Patent Application No. PCT/US2015/053313, filed Sep. 30, 2015, which claims priority to U.S. Provisional Patent Application No. 62/058,122 filed Oct. 1, 2014; U.S. Provisional Patent Application No. 62/058,123 filed Oct. 1, 2014; U.S. Provisional Patent Application No. 62/058,124 filed Oct. 1, 2014; and U.S. Provisional Patent Application No. 62/058,125 filed Oct. 1, 2014, the disclosures of each of which are incorporated herein by reference in their entireties.

FIELD OF THE INVENTION

The invention is generally in the field of injectable low-viscosity pharmaceutical formulations of polysaccharides and nucleic acids, as well as methods of making and using thereof.

BACKGROUND OF THE INVENTION

Polysaccharides and nucleic acids represent a diverse class of biological macromolecules with a wide spectrum of physiological activity. In addition to their essential roles in many foundational biological processes, polysaccharides and nucleic acids have been explored as therapeutic agents. Because of their structural complexity, polysaccharides and nucleic acids can selectively target novel or difficult biologic targets associated with many intractable diseases.

However, the same complexity from which their promising activity is derived also imparts significant challenges to the design, preparation, and delivery of polysaccharides and nucleic acids. Because polysaccharides and nucleic acids are both characterized by a high degree of polar functional groups, solutions of these compounds often exhibit significant intramolecular interactions, resulting in high viscosity. The use of a high-viscosity formulation for the storage and delivery of biological agents is disfavored for many different reasons: viscous formulations are difficult to administer by injection, cause pain at the site of injection, are often imprecise, and/or may have decreased chemical and/or physical stability. Furthermore, highly viscous liquid formulations are difficult to manufacture and draw into a syringe. High-viscosity solutions also require larger diameter needles for injection and produce more pain at the injection site.

These concerns are especially pressing with some polysaccharides and nucleic acids, as these agents may be administered at concentrations exceeding 10 mg/mL, 20 mg/mL, 100 mg/mL, 200 mg/mL or even 500 mg/mL. At higher concentrations, formulations of polysaccharides and nucleic acids become increasingly viscous, exacerbating the difficulties described above.

Polysaccharides and nucleic acids are also under investigation as components of drug delivery systems, such as nanoparticles, which also are subject to inter-particle interactions. Therefore, it is desired to develop technology to reduce the viscosity of such systems and thus enable rapid administration of polysaccharide or nucleic acid-containing solutions.

In addition to concerns associated with high-viscosity pharmaceutical formulations, the tendency of polysaccharides and nucleic acids to form highly-viscous solutions also complicates their manufacture and purification. Many commercially important polysaccharides, such as starch, dextrin, celluloses, pentosans, xylans and beta-glucans, as well as many nucleic acids, such as plasmid DNA vaccines, are produced by fermentation processes. As polysaccharide or nucleic acid levels rise in the fermentation mixture, the viscosity of the mixture rapidly increases. Historically, additional energy (in the form of heat or rapid stirring) has been applied to fermentation media in order to achieve suitable mixing of the individual components. However, many organisms (and nucleic acid products) are not compatible with overly high temperatures, and high levels of shear stress may disrupt the cellular structure of the organisms, decreasing reaction efficiency and complicating the purification of the product. Accordingly, there has been extensive research for solutions to the viscosity-related problems associated with fermentation-based manufacturing methods. See, e.g., A. E. Carnes et al., *Recent Patents on Biotechnology* 2007, 1:000-000 and *Biotechnology of Microbial Exopolysaccharides*, I. W. Sutherland, eds., pp. 82-87, Cambridge University Press, Cambridge, 1990. However, many of the solutions described to date rely on specialized organisms or enzymes, or require elaborate and costly apparatus.

It is, therefore, an object of the present invention to provide concentrated, low-viscosity liquid formulations of pharmaceutically important polysaccharides and nucleic acids, especially high-molecular-weight polysaccharides and nucleic acids.

It is a further object of the present invention to provide concentrated low-viscosity liquid formulations of polysaccharides and nucleic acids, especially high-molecular-weight polysaccharides and nucleic acids, capable of delivering therapeutically effective amounts of these polysaccharides and nucleic acids in volumes useful for SC and IM injections.

It is a further object of the present invention to provide the concentrated liquid formulations of polysaccharides and nucleic acids, especially high-molecular-weight polysaccharides and nucleic acids, with low viscosities that can improve injectability and/or patient compliance, convenience, and/or comfort.

It is also an object of the present invention to provide methods for making and storing concentrated, low-viscosity formulations of polysaccharides and nucleic acids, especially high-molecular-weight polysaccharides and nucleic acids.

It is an additional object of the present invention to provide simple and cost-effective methods for reducing viscosity during the fermentation (i.e., by a microorganism or isolated enzyme) and purification of polysaccharides and nucleic acids.

SUMMARY OF THE INVENTION

Concentrated, low-viscosity, low-volume liquid compositions of polysaccharides and nucleic acids have been developed. The compositions may be pharmaceutical formulations which can be rapidly and conveniently administered by subcutaneous (SC) or intramuscular (IM) injection, rather than by lengthy intravenous infusion. These formulations include low-molecular-weight and/or high-molecular-weight polysaccharides and/or nucleic acids, in combination with one or more viscosity-lowering agents (e.g., viscosity-lowering compounds of formulae A-I, A-II, A-III and variations thereof, ionic liquids, organophosphates, water-soluble organic dyes, and other viscosity-lowering compounds described herein). The compositions may also be prepared during the manufacture and purification of polysaccharides and nucleic acids. The low viscosity of these compositions facilitates operations such as filtration and chromatography.

The concentration of the polysaccharides and nucleic acids is between about 10 mg/mL and about 5,000 mg/mL, more preferably from about 100 mg/mL to about 2,000 mg/mL. In some embodiments, the concentration is between about 5 mg/mL and 1000 mg/mL, preferably between about 100 mg/mL to about 500 mg/mL, more preferably from about 300 mg/mL to about 500 mg/mL. Formulations containing polysaccharides and/or nucleic acids, in combination with viscosity-lowering agents are stable when stored at a temperature of 4° C., for a period of at least one month, preferably at least two months, and most preferably at least three months. The viscosity of the formulation is less than about 75 centipoise (cP), preferably below 50 cP, and most preferably below 20 cP at about 25° C. In some embodiments, the viscosity is less than about 15 cP or even less than or about 10 cP at about 25° C. In certain embodiments, the viscosity of the formulation is about 10 cP. Formulations containing viscosity-lowering agents (e.g., viscosity-lowering compounds of formulae A-I, A-II, A-III and variations thereof, ionic liquids, organophosphates, water-soluble organic dyes, and other viscosity-lowering compounds described herein) and one or more polysaccharides or nucleic acids typically are measured at shear rates from about 0.6 $s^{-1}$ to about 450 $s^{-1}$, and preferably from about 2 $s^{-1}$ to about 400 $s^{-1}$, when measured using a cone and plate viscometer. Formulations containing viscosity-lowering agents and one or more polysaccharides or nucleic acids typically are measured at shear rates from about 3 $s^{-1}$ to about 55,000 $s^{-1}$, and preferably from about 20 $s^{-1}$ to about 2,000 $s^{-1}$, when measured using a microfluidic viscometer.

The viscosity of the polysaccharide or nucleic acid formulation is reduced by the presence of one or more viscosity-lowering agent (e.g., viscosity-lowering compounds of formulae A-I, A-II, A-III and variations thereof, ionic liquids, organophosphates, water-soluble organic dyes, and other viscosity-lowering compounds described herein). Unless specifically stated otherwise, the term "viscosity-lowering agent" includes both single compounds and mixtures of two or more compounds. It is preferred that the viscosity-lowering agent is present in the formulation at a concentration less than about 1.0 M, preferably less than about 0.50 M, more preferably less than about 0.30 M, and most preferably less than about 0.15 M. In some embodiments, the viscosity-lowering agent is present in the formulation in concentrations as low as 0.01 M. The formulations can have a viscosity that is at least about 30% less, preferably at least about 50% less, most preferably at least about 75% less, than the viscosity of the corresponding formulation under the same conditions except for replacement of the viscosity-lowering agent with an appropriate buffer or salt at about the same concentration. In some embodiments, a low-viscosity formulation is provided where the viscosity of the corresponding formulation without the viscosity-lowering agent is greater than about 200 cP, greater than about 500 cP, or even above about 1,000 cP. In a preferred embodiment, the formulation is measured at a shear rate of at least about 0.5 $s^{-1}$ when measured using a cone and plate viscometer or at least about 1.0 $s^{-1}$ when measured using a microfluidic viscometer.

In some embodiments, the viscosity-lowering agent (e.g., viscosity-lowering compounds of formulae A-I, A-II, A-III and variations thereof, ionic liquids, organophosphates, water-soluble organic dyes, and other viscosity-lowering compounds described herein) and one or more polysaccharides or nucleic acids are provided in a lyophilized dosage unit, sized for reconstitution with a sterile aqueous pharmaceutically acceptable vehicle, to yield the concentrated low-viscosity liquid formulations. The presence of the viscosity-lowering agent(s) facilitates and/or accelerates the reconstitution of the lyophilized dosage unit compared to a lyophilized dosage unit not containing a viscosity-lowering agent.

Methods are provided herein for preparing concentrated, low-viscosity liquid formulations of high-molecular-weight polysaccharides or nucleic acids, as well as methods for storing the low-viscosity, high-concentration polysaccharide or nucleic acid formulations, and for administration thereof to patients. In another embodiment, the viscosity-lowering agent (e.g., viscosity-lowering compounds of formulae A-I, A-II, A-III and variations thereof, ionic liquids, organophosphates, water-soluble organic dyes, and other viscosity-lowering compounds described herein) is added to facilitate processing (e.g., pumping, concentration, and/or filtration) by reducing the viscosity of the polysaccharide/nucleic acid solutions.

DETAILED DESCRIPTION OF THE INVENTION

I. Definitions

Figure 1:
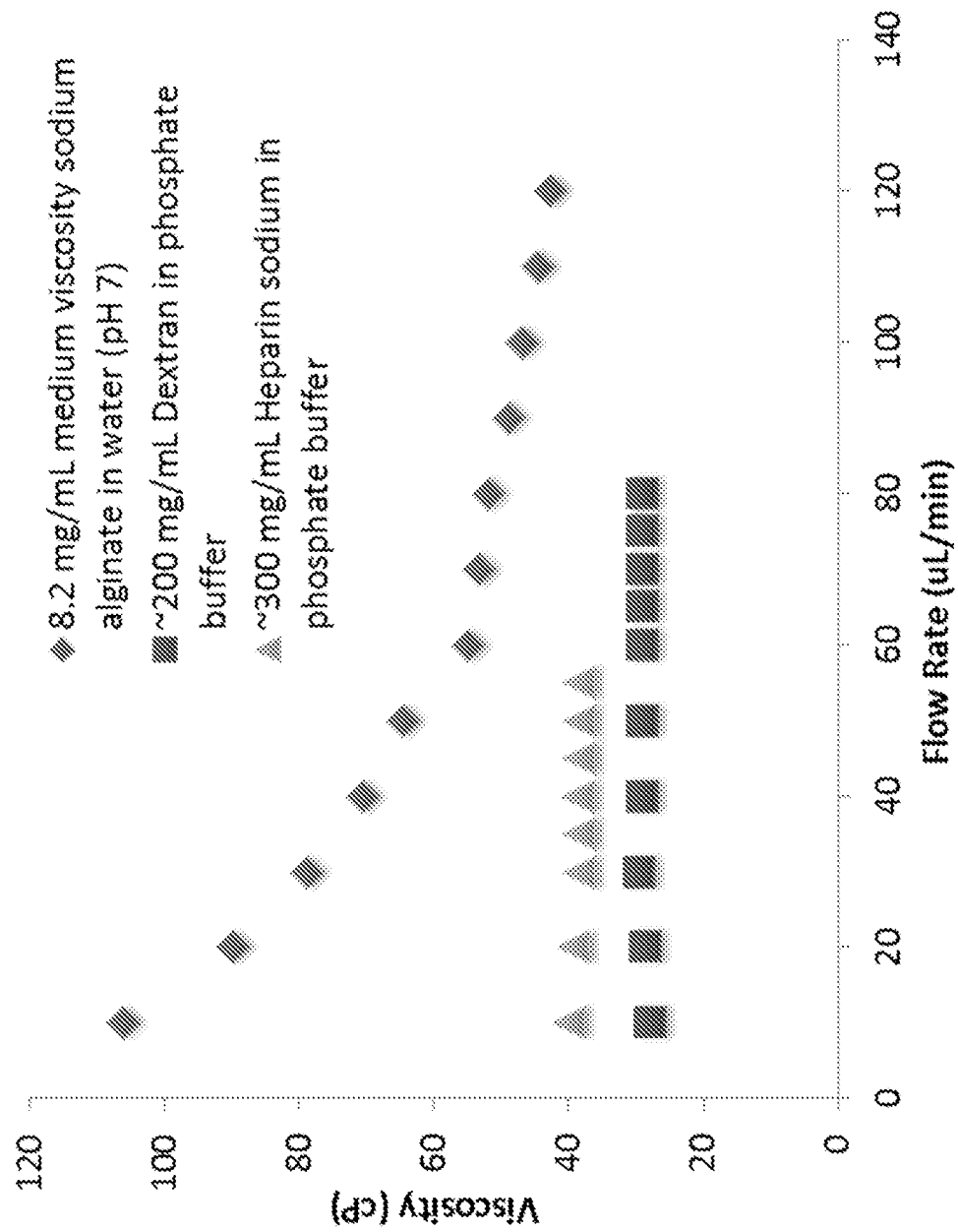
FIG. 1 depicts the viscosity in cP as a function of the flow rate for aqueous solutions of "medium-viscosity" sodium alginate in water (8.2 mg/mL, pH 7.4, diamonds), Dextran in phosphate buffer (approximately 200 mg/mL, squares), and Heparin sodium in phosphate buffer (approximately 300 mg/mL, pH 7.1, triangles).

The term "polysaccharide," as used herein, refers to a compound made from at least two monosaccharide units which are linked via a glycosylic (or glycosidic) bond. Unless otherwise specified, a polysaccharide may contain only sugar components, or may contain non-sugar components as well, such as amino acids and small molecule aglycones. Polysaccharides having a molecular weight (expressed in kDa wherein "Da" stands for "Daltons" and 1 kDa=1,000 Da) greater than about 10,000 Da may be designated "high-molecular-weight polysaccharides," whereas polysaccharides having a molecular weight less than about 10,000 Da may be designated "low-molecular-weight polysaccharides." Polysaccharide molecular weight may be determined using standard methods known to one skilled in the art, including, but not limited to, mass spectrometry (e.g., of digested fragments by ESI or MALDI) or calculation from known carbohydrate sequences. Polysaccharides can be naturally occurring or non-naturally occurring, synthetic, or semi-synthetic.

"Nucleic acid," as used herein, refers to polymers made from at least two nucleotides. Nucleic acids may be single stranded, as in the case of RNA, or double stranded, as in the case of DNA. Nucleic acids may be made from naturally occurring nucleotides, or may contain one or more non-natural nucleotides. The nucleic acid may also include derivatives and analogs of nucleic acids, including peptide nucleic acids (a polyamino acid sequence substituted by purine and pyrimidine bases) and glycol nucleic acids (wherein the cyclic ribose component is replaced by an acyclic di- or triol linked by phosphodiester bonds).

"Essentially pure polysaccharide" (or "essentially pure nucleic acid") and "substantially pure polysaccharide" (or "substantially pure nucleic acid") are used interchangeably herein and refer to a composition comprising at least about 90% by weight pure polysaccharide (or nucleic acid), preferably at least about 95% pure polysaccharide (or nucleic acid) by weight.

"Rheology" refers to the study of the deformation and flow of matter.

"Viscosity" refers to the resistance of a substance (typically a liquid) to flow. Viscosity is related to the concept of shear force; it can be understood as the effect of different layers of the fluid exerting shearing force on each other, or on other surfaces, as they move against each other. There are several measures of viscosity. The units of viscosity are $Ns/m^2$, known as Pascal-seconds (Pa-s). Viscosity can be "kinematic" or "absolute". Kinematic viscosity is a measure of the rate at which momentum is transferred through a fluid. It is measured in Stokes (St). The kinematic viscosity is a measure of the resistive flow of a fluid under the influence of gravity. When two fluids of equal volume and differing viscosity are placed in identical capillary viscometers and allowed to flow by gravity, the more viscous fluid takes longer than the less viscous fluid to flow through the capillary. If, for example, one fluid takes 200 seconds (s) to complete its flow and another fluid takes 400 s, the second fluid is called twice as viscous as the first on a kinematic viscosity scale. The dimension of kinematic viscosity is length/time. Commonly, kinematic viscosity is expressed in centiStokes (cSt). The SI unit of kinematic viscosity is $mm^2/s$, which is equal to 1 cSt. The "absolute viscosity," sometimes called "dynamic viscosity" or "simple viscosity," is the product of kinematic viscosity and fluid density. Absolute viscosity is expressed in units of centipoise (cP). The SI unit of absolute viscosity is the milliPascal-second (mPa-s), where 1 cP=1 mPa-s. Viscosity may be measured by using, for example, a viscometer at a given shear rate or multiple shear rates. An "extrapolated zero-shear" viscosity can be determined by creating a best fit line of the four highest-shear points on a plot of absolute viscosity versus shear rate, and linearly extrapolating viscosity back to zero-shear. Alternatively, for a Newtonian fluid, viscosity can be determined by averaging viscosity values at multiple shear rates. Viscosity can also be measured using a microfluidic viscometer at single or multiple shear rates (also called flow rates), wherein absolute viscosity is derived from a change in pressure as a liquid flows through a channel. Viscosity equals shear stress over shear rate. Viscosities of fluids measured with microfluidic viscometers can, in some embodiments, be directly compared to extrapolated zero-shear viscosities, for example those extrapolated from viscosities measured at multiple shear rates using a cone and plate viscometer.

"Shear rate" refers to the rate of change of velocity at which one layer of fluid passes over an adjacent layer. The velocity gradient is the rate of change of velocity with distance from the plates. This simple case shows the uniform velocity gradient with shear rate $(v_1-v_2)/h$ in units of (cm/sec)/(cm)=1/sec. Hence, shear rate units are reciprocal seconds or, in general, reciprocal time. For a microfluidic viscometer, change in pressure and flow rate are related to shear rate. "Shear rate" is related to the speed with which a material is deformed. Formulations containing viscosity-lowering agents and polysaccharides or nucleic acids are typically measured at shear rates ranging from about 0.5 $s^{-1}$ to about 200 $s^{-1}$ when measured using a cone and plate viscometer and a spindle appropriately chosen by one skilled in the art to accurately measure viscosities in the viscosity range of the sample of interest (i.e., a sample of 20 cP is most accurately measured on a CPE40 spindle affixed to a DV2T viscometer (Brookfield)); or from greater than about 20 $s^{-1}$ to about 3,000 $s^{-1}$ when measured using a microfluidic viscometer.

For classical "Newtonian" fluids, as generally used herein, viscosity is essentially independent of shear rate. For "non-Newtonian fluids," however, viscosity either decreases or increases with increasing shear rate, e.g., the fluids are "shear thinning" or "shear thickening", respectively. In the case of concentrated (i.e., high-concentration) polysaccharide and nucleic acid solutions, this may manifest as pseudoplastic shear-thinning behavior, i.e., a decrease in viscosity with shear rate.

The term "chemical stability," as generally used herein, refers to the ability of the polysaccharide and nucleic acid components in a formulation to resist degradation via chemical pathways, such as oxidation, deamidation, or hydrolysis. A polysaccharide or nucleic acid formulation is typically considered chemically stable if less than about 5% of the components are degraded after 24 months at 4° C.

The term "physical stability," as generally used herein, refers to the ability of a polysaccharide or nucleic acid formulation to resist physical deterioration, such as aggregation. A formulation that is physically stable forms only an acceptable percentage of irreversible aggregates (e.g., dimers, trimers, or other aggregates) of the bioactive polysaccharide or nucleic acid agent. The presence of aggregates may be assessed in a number of ways, including by measuring the average particle size of the polysaccharide or nucleic acid in the formulation by means of dynamic light scattering. A formulation is considered physically stable if less than about 5% irreversible aggregates are formed after 24 months at 4° C. Acceptable levels of aggregated contaminants ideally would be less than about 2%. Levels as low as about 0.2% are achievable, although approximately 1% is more typical.

The term "stable formulation," as generally used herein, means that a formulation is both chemically stable and physically stable. A stable formulation may be one in which more than about 95% of the bioactive polysaccharide or nucleic acid molecules retain bioactivity in a formulation after 24 months of storage at 4° C., or equivalent solution conditions at an elevated temperature, such as one month storage at 40° C. Various analytical techniques for measuring polysaccharide and nucleic acid stability are available in the art. Stability can be measured at a selected temperature for a certain time period. For rapid screening, for example, the formulation may be kept at 40° C., for 2 weeks to one month, at which time residual biological activity is measured and compared to the initial condition to assess stability. When the formulation is to be stored at 2-8° C., generally the formulation should be stable at 30° C. or 40° C. for at least one month and/or stable at 2-8° C. for at least 2 years. When the formulation is to be stored at room temperature, about 25° C., generally the formulation should be stable for at least 2 years at about 25° C. and/or stable at 40° C. for at least about 6 months. The extent of aggregation following lyophilization and storage can be used as an indicator of polysaccharide or nucleic acid stability. In some embodiments, the stability is assessed by measuring the particle size of the polysaccharides or nucleic acids in the formulation. In some embodiments, stability may be assessed by measuring the activity of a formulation using standard biological activity or binding assays well within the abilities of one ordinarily skilled in the art.

The term "concentrated" or "high-concentration", as generally used herein, describes liquid formulations having a final concentration of polysaccharide or nucleic acid greater than about 10 mg/mL, preferably greater than about 50 mg/mL, more preferably greater than about 100 mg/mL, still more preferably greater than about 200 mg/mL, or most preferably greater than about 250 mg/mL.

A "reconstituted formulation," as generally used herein, refers to a formulation which has been prepared by dissolving a dry powder, lyophilized, spray-dried, or solvent-precipitated polysaccharide or nucleic acid in a diluent, such that the polysaccharide or nucleic acid is dissolved or dispersed in aqueous solution for administration.

A "lyoprotectant" is a substance which, when combined with a polysaccharide or nucleic acid, significantly reduces chemical and/or physical instability of the polysaccharide or nucleic acid upon lyophilization and/or subsequent storage. Exemplary lyoprotectants include sugars and their corresponding sugar alcohols, such as sucrose, lactose, trehalose, dextran, erythritol, arabitol, xylitol, sorbitol, and mannitol; amino acids, such as arginine or histidine; lyotropic salts, such as magnesium sulfate; polyols, such as propylene glycol, glycerol, poly(ethylene glycol), or poly(propylene glycol); and combinations thereof. Additional exemplary lyoprotectants include gelatin, dextrins, modified starch, and carboxymethyl cellulose. Preferred sugar alcohols are those compounds obtained by reduction of mono- and di-saccharides, such as lactose, trehalose, maltose, lactulose, and maltulose. Additional examples of sugar alcohols are glucitol, maltitol, lactitol and isomaltulose. The lyoprotectant is generally added to the pre-lyophilized formulation in a "lyoprotecting amount." This means that, following lyophilization of the polysaccharide or nucleic acid in the presence of the lyoprotecting amount of the lyoprotectant, the polysaccharide or nucleic acid essentially retains its physical and chemical stability and integrity.

A "diluent" or "carrier," as generally used herein, is a pharmaceutically acceptable (i.e., safe and non-toxic for administration to a human or another mammal) and useful ingredient for the preparation of a liquid formulation, such as an aqueous formulation reconstituted after lyophilization. Exemplary diluents include sterile water, bacteriostatic water for injection (BWFI), a pH buffered solution (e.g., phosphate-buffered saline), sterile saline solution, Ringer's solution, or dextrose solution, and combinations thereof.

A "preservative" is a compound which can be added to the formulations herein to reduce contamination by and/or action of bacteria, fungi, or another infectious agent. The addition of a preservative may, for example, facilitate the production of a multi-use (multiple-dose) formulation. Examples of potential preservatives include octadecyldimethylbenzylammonium chloride, hexamethonium chloride, benzalkonium chloride (a mixture of alkylbenzyldimethylammonium chlorides in which the alkyl groups are long-chained), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

A "bulking agent," as generally used herein, is a compound which adds mass to a lyophilized mixture and contributes to the physical structure of the lyophilized cake (e.g. facilitates the production of an essentially uniform lyophilized cake which maintains an open pore structure). Exemplary bulking agents include mannitol, glycine, lactose, modified starch, poly(ethylene glycol), and sorbitol.

A "therapeutically effective amount" is the least concentration required to effect a measurable improvement or prevention of any symptom of a particular condition or disorder, to effect a measurable enhancement of life expectancy, or to generally improve patient quality of life. The therapeutically effective amount is dependent upon the specific biologically active molecule and the specific condition or disorder to be treated. The therapeutically effective amounts of polysaccharides and nucleic acids that has not yet been established, or for treating specific disorders with known polysaccharides or nucleic acids to be clinically applied to treat additional disorders, may be determined by standard techniques which are well within the craft of a skilled artisan, such as a physician.

The term "injectability" or "syringeability," as generally used herein, refers to the injection performance of a pharmaceutical formulation through a syringe equipped with an 18-32 gauge needle, optionally thin walled. Injectability depends upon factors such as pressure or force required for injection, evenness of flow, aspiration qualities, and freedom from clogging. Injectability of the liquid pharmaceutical formulations may be assessed by comparing the injection force of a reduced-viscosity formulation to a standard formulation without added viscosity-lowering agents. The reduction in the injection force of the formulation containing a viscosity-lowering agent reflects improved injectability of that formulation. The reduced viscosity formulations have improved injectability when the injection force is reduced by at least 10%, preferably by at least 30%, more preferably by at least 50%, and most preferably by at least 75% when compared to a standard formulation having the same concentration of polysaccharide or nucleic acid under otherwise the same conditions, except for replacement of the viscosity-lowering agent with an appropriate buffer of about the same concentration. Alternatively, injectability of the liquid pharmaceutical formulations may be assessed by comparing the time required to inject the same volume, such as 0.5 mL, or more preferably about 1 mL, of different liquid polysaccharide or nucleic acid formulations when the syringe is depressed with the same force.

The term "injection force," as generally used herein, refers to the force required to push a given liquid formulation through a given syringe equipped with a given needle gauge at a given injection speed. The injection force is typically reported in Newtons. For example, the injection force may be measured as the force required to push a liquid formulation through a 1 mL plastic syringe having a 0.25 inch inside diameter, equipped with a 0.50 inch 27 gauge needle at a 250 mm/min injection speed. Testing equipment can be used to measure the injection force. When measured under the same conditions, a formulation with lower viscosity will generally require an overall lower injection force.

The "viscosity gradient," as used herein, refers to the rate of change of the viscosity of a polysaccharide or nucleic acid solution as polysaccharide or nucleic acid concentration increases. The viscosity gradient can be approximated from a plot of the viscosity as a function of the polysaccharide or nucleic acid concentration for a series of formulations that are otherwise the same but have different polysaccharide or nucleic acid concentrations. The viscosity increases approximately exponentially with increasing polysaccharide or nucleic acid concentration. The viscosity gradient at a specific polysaccharide or nucleic acid concentration can be approximated from the slope of a line tangent to the plot of viscosity as a function of polysaccharide or nucleic acid concentration. The viscosity gradient can be approximated from a linear approximation to the plot of viscosity as a function of any polysaccharide or nucleic acid concentration or over a narrow window of polysaccharide or nucleic acid concentrations. In some embodiments a formulation is said to have a decreased viscosity gradient if, when the viscosity as a function of polysaccharide or nucleic acid concentration is approximated as an exponential function, the exponent of the exponential function is smaller than the exponent obtained for the otherwise same formulation without the viscosity-lowering agent. In a similar manner, a formulation can be said to have a lower/higher viscosity gradient when compared to a second formulation if the exponent for the formulation is lower/higher than the exponent for the second formulation. The viscosity gradient can be numerically approximated from a plot of the viscosity as a function of polysaccharide or nucleic acid concentration by other methods known to the skilled formulation researchers.

The term "reduced-viscosity formulation," as generally used herein, refers to a liquid formulation having a high concentration of a polysaccharide or nucleic acid that is modified by the presence of one or more additives to lower the viscosity, as compared to a corresponding formulation that does not contain the viscosity-lowering additive(s).

The term "osmolarity," as generally used herein, refers to the total number of dissolved components per liter. Osmolarity is similar to molarity but includes the total number of moles of dissolved species in solution. An osmolarity of 1 Osm/L means there is 1 mole of dissolved components per L of solution. Some solutes, such as ionic solutes that dissociate in solution, will contribute more than 1 mole of dissolved components per mole of solute in the solution. For example, NaCl dissociates into $Na^+$ and $Cl^-$ in solution and thus provides 2 moles of dissolved components per 1 mole of dissolved NaCl in solution. Physiological osmolarity is typically in the range of about 280 mOsm/L to about 310 mOsm/L.

The term "tonicity," as generally used herein, refers to the osmotic pressure gradient resulting from the separation of two solutions by a semi-permeable membrane. In particular, tonicity is used to describe the osmotic pressure created across a cell membrane when a cell is exposed to an external solution. Solutes that can cross the cellular membrane do not contribute to the final osmotic pressure gradient. Only those dissolved species that do not cross the cell membrane will contribute to osmotic pressure differences and thus tonicity.

The term "hypertonic," as generally used herein, refers to a solution with a higher concentration of solutes than is present on the inside of the cell. When a cell is immersed into a hypertonic solution, the tendency is for water to flow out of the cell in order to balance the concentration of the solutes.

The term "hypotonic," as generally used herein, refers to a solution with a lower concentration of solutes than is present on the inside of the cell. When a cell is immersed into a hypotonic solution, water flows into the cell in order to balance the concentration of the solutes.

The term "isotonic," as generally used herein, refers to a solution wherein the osmotic pressure gradient across the cell membrane is essentially balanced. An isotonic formulation is one which has essentially the same osmotic pressure as human blood. Isotonic formulations will generally have an osmotic pressure from about 250 mOsm/kg to 350 mOsm/kg.

The term "liquid formulation," as used herein, is a polysaccharide or nucleic acid that is either supplied in an acceptable pharmaceutical diluent or one that is reconstituted in an acceptable pharmaceutical diluent prior to administration to the patient.

The terms "branded" and "reference," when used to refer to a biologic product, are used interchangeably herein to mean the single biological product licensed under section 351(a) of the U.S. Public Health Service Act (42 U.S.C. § 262).

The term "biosimilar," as used herein, is generally used interchangeably with "a generic equivalent" or "follow-on." For example, a "biosimilar polysaccharide" refers to a subsequent version of an innovator's polysaccharide typically made by a different company. "Biosimilar" when used in reference to a branded polysaccharide or branded biologic can refer to a biological product evaluated against the branded polysaccharide or branded biologic and licensed under section 351(k) of the U.S. Public Health Service Act (42 U.S.C. § 262). A biosimilar polysaccharide can be one that satisfies one or more guidelines adopted October 2009 by the Committee for Medicinal Products for Human Use (CHMP) of the European Medicines Agency and published by the European Union as "Guideline on non-clinical and clinical development of similar biological medicinal products containing low-molecular-weight-heparins" (Document Reference EMEA/CHMP/BMWP/118264/2007).

Biosimilars can be produced by microbial cells (prokaryotic, eukaryotic), cell lines of human or animal origin (e.g., mammalian, avian, insect), or tissues derived from animals or plants. The expression construct for a proposed biosimilar product will generally encode the same primary amino acid sequence as its reference product. Minor modifications that will not have an effect on safety, purity, or potency, may be present.

A biosimilar polysaccharide is similar to the reference polysaccharide physiochemically or biologically both in terms of safety and efficacy. The biosimilar polysaccharide can be evaluated against a reference polysaccharide using one or more in vitro studies including assays detailing binding to target proteins. In vitro comparisons may be combined with in vivo data demonstrating similarity of pharmacokinetics, pharmacodynamics, and/or safety. Clinical evaluations of a biosimilar polysaccharide against a reference polysaccharide can include comparisons of pharmacokinetic properties (e.g. $AUC_{0-inf}$, $AUC_{0-t}$, $C_{max}$, $t_{max}$, $C_{trough}$); pharmacodynamic endpoints; or similarity of clinical efficacy (e.g. using randomized, parallel group comparative clinical trials). The quality comparison between a biosimilar polysaccharide and a reference polysaccharide can be evaluated using established procedures, and can include those adapted for the procedures described for proteins in the "Guideline on similar biological medicinal products containing biotechnology-derived proteins as active substance: Quality issues" (EMEA/CHMP/BWP/49348/2005).

The term "viscosity-lowering agent," as used herein, refers to a compound which acts to reduce the viscosity of a solution relative to the viscosity of the solution absent the viscosity-lowering agent. The viscosity-lowering agent may be a single compound, or may be a mixture of one or more compounds. When the viscosity-lowering agent is a mixture of two or more compounds, the listed concentration refers to each individual agent, unless otherwise specified. By way of example, a formulation containing about 0.25 M camphorsulfonic acid arginine as the viscosity-lowering agent is a solution having camphorsulfonic acid at a concentration of 0.25 M, and arginine at a concentration of 0.25 M.

Certain viscosity-lowering agents contain acidic or basic functional groups. Whether or not these functional groups are fully or partially ionized depends on the pH of the formulation they are in. Unless otherwise specified, reference to a formulation containing a viscosity-lowering agent having an ionizable functional group includes both the parent compound and any possible ionized states.

As used herein, the term "hydrogen bond donor" refers to a hydrogen atom connected to a relatively electronegative atom, which creates a partial positive charge on the hydrogen atom.

As used herein, the term "hydrogen bond acceptor" refers to a relatively electronegative atom or functional group capable of interacting with a hydrogen atom bearing a partial positive charge.

As used herein, the term "freely rotating bond" refers to any singly bonded pair of non-hydrogen atoms.

As used herein, the term "molecular polar surface area" refers to the total exposed polar area on the surface of the molecule of interest.

As used herein, the term "molar volume" refers to the total volume that one mole of the molecule of interest occupies in its native state (i.e. solid, liquid).

As used herein, the term "polarizability" refers to the induced dipole moment when the molecule of interest is placed in an electric field of unit strength.

As used herein, the term "pharmaceutically acceptable salts" refers to salts prepared from pharmaceutically acceptable non-toxic acids and bases, including inorganic acids and bases, and organic acids and bases. Suitable non-toxic acids include inorganic and organic acids such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Suitable positively charged counterions include sodium, potassium, lithium, calcium and magnesium.

As used herein, the term "ionic liquid" refers to a crystalline or amorphous salt, zwitterion, or mixture thereof, that is a liquid at or near temperatures where most conventional salts are solids: at less than 200° C., preferably less than 100° C., or more preferably less than 80° C. Some ionic liquids have melting temperatures around room temperature, e.g., between 10° C. and 40° C., or between 15° C. and 35° C. The term "zwitterion" is used herein to describe an overall neutrally charged molecule which carries formal positive and negative charges on different chemical groups in the molecule. Examples of ionic liquids are described in Riduan et al., *Chem. Soc. Rev.*, 42:9055-9070, 2013; Rantwijk et al., *Chem. Rev.*, 107:2757-2785, 2007; Earle et al., *Pure Appl. Chem.*, 72(7):1391-1398, 2000; and Sheldon et al., *Green Chem.*, 4:147-151, 2002.

As used herein, the term "organophosphate" refers to a compound containing one or more phosphoryl groups at least one of which is covalently connected to an organic group through a phosphoester bond.

As used herein, a "water-soluble organic dye", used interchangeably with "water-soluble dye", is an organic molecule having a molar solubility of at least 0.001 M at 25° C. and pH 7, and that absorbs certain wavelengths of light, preferably in the visible-to-infrared portion of the electromagnetic spectrum, while possibly transmitting or reflecting other wavelengths of light.

As used herein, the term "chalcogen" refers to Group 16 elements, including oxygen, sulfur, and selenium, in any oxidation state. For instance, unless specified otherwise, the term "chalcogen" also includes $SO_2$.

As used herein, the term "alkyl group" refers to straight-chain, branched-chain, and cyclic hydrocarbon groups. Unless specified otherwise, the term alkyl group embraces hydrocarbon groups containing one or more double or triple bonds. An alkyl group containing at least one ring system is a "cycloalkyl" group. An alkyl group containing at least one double bond is an "alkenyl group," and an alkyl group containing at least one triple bond is an "alkynyl group."

The term "Aryl" as used herein refers to aromatic carbon ring systems, including fused ring systems. In an "aryl" group, each of the atoms that form the ring is a carbon atom.

The term "Heteroaryl" as used herein refers to aromatic ring systems, including fused ring systems, wherein at least one of the atoms that forms the ring is a heteroatom.

The term "Heterocycle" as used herein refers to ring systems, including fused ring systems, that are not aromatic, wherein at least one of the atoms that forms the ring is a heteroatom.

The term "heteroatom" as used herein is any non-carbon or non-hydrogen atom. Preferred heteroatoms include oxygen, sulfur, and nitrogen. Exemplary heteroaryl and heterocyclyl rings include: benzimidazolyl, benzofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

II. Formulations

Biocompatible, low-viscosity polysaccharide and nucleic acid solutions can be used to deliver therapeutically effective amounts of polysaccharide or nucleic acid in volumes useful for subcutaneous (SC) and intramuscular (IM) injections, typically less than or about 2 mL for SC and less than or about 5 mL for IM, more preferably less than or about 1 mL for SC, and less than or about 3 mL for IM. The polysaccharide and nucleic acid can generally have any molecular weight, although in some embodiments high-molecularweight polysaccharides and nucleic acids are preferred. In other embodiments the polysaccharides and nucleic acids are low-molecular-weight polysaccharides and nucleic acids.

Formulations may have polysaccharides and nucleic acids at concentrations between about 5 mg/mL and about 5,000 mg/mL. The formulations may have a polysaccharide and nucleic acid concentrations greater than 100 mg/mL, preferably greater than 150 mg/mL, more preferably greater than about 175 mg/ml, even more preferably greater than about 200 mg/mL, even more preferably greater than about 225 mg/mL, even more preferably greater than about 250 mg/mL, and most preferably greater than or about 300 mg/mL. In certain embodiments, the formulations may have a concentration between about 5 mg/mL and about 1,000 mg/mL, preferably between about 15 mg/mL and about 500 mg/mL, more preferably between about 50 mg/mL and about 300 mg/mL, and even more preferably between about 100 mg/mL and about 250 mg/mL. In the absence of a viscosity-lowering agent, the viscosity of a polysaccharide or nucleic acid formulation increases exponentially as the concentration is increased. Such formulations, in the absence of a viscosity-lowering agent, may have viscosities greater than 20 cP, greater than 50 cP, greater than 100 cP, greater than 150 cP, greater than 200 cP, greater than 300 cP, greater than 500 cP, or even greater than 1,000 cP, when measured at 25° C. Such formulations are often unsuitable for SC or IM injection. The use of one or more viscosity-lowering agents (e.g., viscosity-lowering compounds of formulae A-I, A-II, A-III and variations thereof, ionic liquids, organophosphates, water-soluble organic dyes, and other viscosity-lowering compounds described herein) permits the preparation of formulations having a viscosity less than or about 100 cP, preferably less than or about 75 cP, more preferably less than or about 50 cP, even more preferably less than or about 30 cP, even more preferably less than or about 20 cP, or most preferably less than or about 10 cP, when measured at 25° C.

Although the viscosity-lowering agent(s) may be used to lower the viscosity of concentrated polysaccharide and nucleic acid formulations, they may be used in less-concentrated formulations as well. In some embodiments, formulations may have polysaccharide or nucleic acid concentrations between about 10 mg/mL and about 100 mg/mL. The formulations may have a polysaccharide or nucleic acid concentration greater than about 20 mg/mL, greater than about 40 mg/mL, or greater than about 80 mg/mL.

For certain polysaccharides and nucleic acids, formulations not having a viscosity-lowering agent may have viscosities greater than about 20 cP, greater than about 50 cP, or greater than about 80 cP. The use of one or more viscosity-lowering agent permits the preparation of formulations having a viscosity less than or about 80 cP, preferably less than or about 50 cP, even more preferably less than about 20 cP, or most preferably less than or about 10 cP, when measured at 25° C.

In some embodiments, the aqueous polysaccharide and nucleic acid formulations have a viscosity that is at least about 30% less than the analogous formulation without the viscosity-lowering agent(s), when measured under the same conditions. In other embodiments, the formulations have a viscosity that is 40% less, 50% less, 60% less, 70% less, 80% less, 90% less, or even more than 90% less than the analogous formulation without the viscosity-lowering agent(s). In a preferred embodiment, the formulation contains a therapeutically effective amount of the one or more polysaccharides or nucleic acids in a volume of less than about 2 mL, preferably less than about 1 mL, or more preferably less than about 0.75 mL.

The reduced-viscosity formulations have improved injectability and require less injection force compared to the analogous formulation without the viscosity-lowering agent (e.g., in phosphate buffer) under otherwise the same conditions. In some embodiments, the force of injection is decreased by more than about 20%, more than about 30%, more than about 40%, more than about 50%, or more than about 2 fold, as compared to standard formulations without the viscosity-lowering agent(s) under otherwise the same injection conditions. In some embodiments, the formulations possess "Newtonian flow characteristics," defined as having viscosity which is substantially independent of shear rate. The polysaccharide and nucleic acid formulations can be readily injected through needles of about 18-32 gauge. Preferred needle gauges for the delivery of the low-viscosity formulations include 27, 29, and 31 gauge, optionally thin walled.

The formulations may contain one or more additional excipients, such as buffers, surfactants, sugars and sugar alcohols, other polyols, preservatives, antioxidants, and chelating agents. The formulations have a pH and osmolarity suitable for administration without causing significant adverse side effects. In some embodiments, the concentrated, low-viscosity formulations have a pH between 5 and 8, between 5.5 and 7.6, between 6.0 and 7.6, between 6.8 and 7.6, or between 5.5 and 6.5.

The low-viscosity polysaccharide and nucleic acid formulations can allow for greater flexibility in formulation development. The low-viscosity formulations can exhibit changes in viscosity that are less dependent upon the polysaccharide or nucleic acid concentration as compared to the otherwise same formulation without the viscosity-lowering agent. The low-viscosity polysaccharide and nucleic acid formulations can allow for increased concentrations and decreased dosage frequencies of the polysaccharide or nucleic acid. In some embodiments the low-viscosity formulations contain 2 or more, 3 or more, or 4 or more different polysaccharides or nucleic acids. For example, combinations of 2 or more polysaccharides can be provided in a single low-viscosity formulation.

Because polysaccharide and nucleic acid formulations may be administered to patients at higher polysaccharide and nucleic acid concentrations than otherwise similar formulations not containing a viscosity-lowering agent, the dosing frequency of the polysaccharide and nucleic acid can be reduced. For instance, polysaccharide and nucleic acid previously requiring once-daily administration may be administered once every two days, every three days, or even less frequently when the polysaccharides and nucleic acids are formulated with viscosity-lowering agents. Polysaccharides and nucleic acids which currently require multiple administrations on the same day (either at the same time or at different times of the day) may be administered in fewer injections per day. In some instances, the frequency may be reduced to a single injection once a day. By increasing the dosage administered per injection multiple-fold the dosing frequency can be decreased, for example from once every 2 weeks to once every 6 weeks.

In some embodiments, the liquid formulations have a physiological osmolarity, for example, between about 280 mOsm/L to about 310 mOsm/L. In some embodiments, the liquid formulations have an osmolarity greater than about 250 mOsm/L, greater than about 300 mOsm/L, greater than about 350 mOsm/L, greater than about 400 mOsm/L, or greater than about 500 mOsm/L. In some embodiments, the formulations have an osmolarity of about 200 mOsm/L to about 2,000 mOsm/L or about 300 mOsm/L to about 1,000 mOsm/L. In some embodiments, the liquid formulations are essentially isotonic to human blood. The liquid formulations can in some cases be hypertonic.

The additives, including the viscosity-lowering agents, can be included in any amount to achieve the desired viscosity levels of the liquid formulation, as long as the amounts are not toxic or otherwise harmful, and do not substantially interfere with the chemical and/or physical stability of the formulation. The viscosity-lowering agent(s) in some embodiments can be independently present in a concentration less than about 1.0 M, preferably less than about 0.50 M, less than or equal to about 0.30 M or less than or equal to 0.15 M. Especially preferred concentrations include about 0.01 M and about 0.10 M. For some embodiments having two or more viscosity-lowering agents, the agents are preferably, but not necessarily, present at the same concentration.

The viscosity-lowering agents permit faster reconstitution of a lyophilized dosage unit. The dosage unit is a lyophilized cake of polysaccharide or nucleic acid, viscosity-lowering agent and other excipients, to which water, saline or another pharmaceutically acceptable fluid is added. In the absence of viscosity-lowering agents, periods of 10 minutes, 20 minutes or even more are often required in order to completely dissolve the lyophilized cake at high polysaccharide or nucleic acid concentrations. When the lyophilized cake contains one or more viscosity-lowering agents, the period required to completely dissolve the cake is often reduced by a factor of two, five or even ten. In certain embodiments, less than five minutes or less than one minute is required to completely dissolve a lyophilized cake containing greater than or about 150, 200, or even 300 mg/mL of a polysaccharide or nucleic acid.

The low-viscosity polysaccharide and nucleic acid formulations allow for greater flexibility in formulation development. The low-viscosity formulations exhibit a viscosity that changes less with increasing polysaccharide or nucleic acid concentrations as compared to the otherwise same formulation without the viscosity-lowering agent(s). The low-viscosity polysaccharide and nucleic acid formulations exhibit a decreased viscosity gradient as compared to the otherwise same formulation without the viscosity-lowering agent.

The viscosity gradient of the polysaccharide and nucleic acid formulation may be 2-fold less, 3-fold less, or even more than 3-fold less than the viscosity gradient of the otherwise same formulation without the viscosity-lowering agent(s). The viscosity gradient of the polysaccharide or nucleic acid formulation may be less than 2.0 cP mL/mg, less than 1.5 cP mL/mg, less than 1.0 cP mL/mg, less than 0.8 cP mL/mg, less than 0.6 cP mL/mg, or less than 0.2 cP mL/mg for a formulation having a polysaccharide or nucleic acid concentration between 10 mg/mL and 2,000 mg/mL. By reducing the viscosity gradient of the formulation, the polysaccharide and nucleic acid concentrations can be increased to a greater degree before an exponential increase in viscosity is observed.

Certain viscosity-lowering agents contain acidic or basic functional groups. Whether or not these functional groups are fully or partially ionized depends on the pH of the formulation they are in. Unless otherwise specified, both the parent compound and any possible ionized states of a viscosity-lowering agent having an ionizable functional group can exist in a formulation.

A. Active Agents

1. Polysaccharides

In certain embodiments, active agents are polysaccharides. The polysaccharide may either be naturally occurring or synthetically derived. The polysaccharide may have molecular weights between about 1-1,000 kDa, between about 1-100 kDa, between about 1-50 kDa, between about 1-20 kDa, between about 3-6 kDa or between about 10-20 kDa. In some embodiments, the polysaccharide may have a molecular weight greater than 500 kDa, greater than 750 kDa, or even greater than 1,000 kDa. Certain polysaccharides may have a molecular weight between about 500-1,000 kDa, or between about 500-750 kDa, or between about 750-1,000 kDa. In other embodiments, the polysaccharide may be small molecule, having a molecular weight less than 1,000 Da, preferably between about 300 and about 1,000 Da. In some embodiments, the polysaccharide is a high molecular weight polysaccharide with a molecular weight of greater than about 10 kDa. In other embodiments the polysaccharide is a low molecular weight polysaccharide with a molecular weight of less than about 10 kDa. In some embodiments, the molecular weight of the polymer is determined by methods known in the art, such as mass spectrometry, and the molecular weight figure is determined using methods known in the art as a number average molecular weight, a weight average molecular weight, or a peak average molecular weight. In some embodiments, the polysaccharide has a molecular weight of about 1-5 kDa, or about 5-10 kDa, or about 5-15 kDa, or about 10-20 kDa.

Polysaccharides may include one or more of the following carbohydrate units: allose, altrose, arabinose, erythrose, erythrulose, fructose, fucitol, fucosamine, fucose, galactosamine, galactosaminitol, galactose, glucosamine, glucosaminitol, glucose, gulose, idose, lyxose, mannosamine, mannose, psicose, quinovose, quinovosamine, rhamnitol, rhamnosamine, rhamnose, ribose, ribulose, sorbose, tagatose, talose, threose, xylose, xylulose, abequose, amicetose, amylose, apiose, arcanose, ascarylose, boivinose, cellobiose, cellotriose, chacotriose, chalcose, cladinose, colitose, cymarose, 2-deoxyribose, 2-deoxyglucose, diginose, digitalose, digitoxose, evalose, evernitrose, gentianose, gentiobiose, hamamelose, inulin, isolevoglucosenone, isomaltose, isomaltotriose, isopanose, kojibiose, lactose, lactosamine, lactosediamine, laminarabiose, levoglucosan, levoglucosenone, maltose, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, umbelliferose, acosamine, bacillosamine, daunosamine, desosamine, forosamine, garosamine, kanosamine, kansosamine, mycaminose, mycosamine, perosamine, pneumosamine, purpurosamine, and rhodosamine.

Glycosaminoglycans (GAGs) may also be formulated with viscosity-lowering agents. Exemplary glycosaminoglycans include, but are not limited to, low molecular weight heparins (LMWH), unfractionated heparin (UFH), chondroitins, keratins, and hyaluronic acids (Yip et al., Molecular Cancer Therapeutics, 2006, 5:2139-2148).

In other embodiments, the polysaccharide may be conjugated to an active agent, such as a vaccine, a protein or a small molecule. Exemplary vaccines that may be conjugated to polysaccharides include haemophilus b, pneumococcal, and meningococcal vaccines. Exemplary proteins that may be conjugated to polysaccharides, include trichosanthin, epidermal growth factor, and the anticancer enzymes asparaginase and carboxypeptidase G2. Exemplary small molecule therapeutics that may be conjugated to polysaccharides include doxorubicin, cisplatin, camptothecin, mitomycin, methotrexate, and paclitaxel. In some embodiments, the liquid pharmaceutical formulation of the invention comprises a polysaccharide that is conjugated to an active agent, such as a vaccine, a protein, or a small molecule. In some embodiments, the liquid pharmaceutical formulation comprises a polysaccharide that is conjugated to a vaccine. In some embodiments, the liquid pharmaceutical formulation comprises a polysaccharide that is conjugated to a small molecule. In some embodiments, the liquid pharmaceutical formulation comprises a polysaccharide that is conjugated to a protein. In some embodiments, the liquid pharmaceutical formulation comprises a polysaccharide that is not conjugated to a protein. In some embodiments, the liquid pharmaceutical formulation of the invention does not comprise a polysaccharide that is conjugated to a protein.

In certain embodiments, the therapeutic polysaccharide may be necuparanib (M402, Momenta Pharmaceuticals, Inc.), heparin sulfate or unfractionated heparin (UFH), a low molecular weight heparin (LMWH) such as enoxaparin (LOVENOX®), dalteparin (FRAGMIN®), nadroparin calcium (FRAXIPARIN®), tinzaparin (INNOHEP®), ardeparin (NORMIFLO®), delingoparin, bemiparin, reviparin, or certoparin, or a non-anticoagulanting heparin such as O-desulfated heparin (ODSH). The polysaccharide may be a glycosaminoglycan (GAGs), including sulfated glycosaminoglycans such as sulodexide. In certain embodiments, the polysaccharides may be curdlan sulfate, acarbose (GLUCOBAY®), fondaparinux (ARIXTRA®), sodium hyaluronate (ORTHOVISC®), cylexin (CY-1503), rivipansel (GMI-1070), GSC-150, Manα (1-2)Man, sialyl Lewis$^a$, sialyl Lewis$^x$ and their mimetics, GQ1bα and its mimetics, and Lewis$^a$ and its mimetics, as well as other compounds described by Ernst et al., *Nature Reviews Drug Discovery*, 2009, 8:661-77.

a. Polysaccharides for Therapeutic Use

Heparin is a highly sulfated glycosaminoglycan that has been used for over eighty years as an anticoagulant. Rather than a single discreet compound, heparin is a collection of different polysaccharide components of 10-100 monosaccharides and having an average molecular weight of about 14,000 to 18,000 Da. Heparin may be fractionated by chemical or enzymatic means into smaller polysaccharide compounds (collectively, "low-molecular weight heparin," or "LMWH"), producing compounds having differing anticoagulative properties.

Many low-molecular weight heparins are about one third the size of heparin, having an average molecular weight from about 4,500 to about 5,000 Da with a distribution of 1,000 to 10,000 Da. Exemplary LMWH compounds include necuparanib, enoxaparin (LOVENOX®), dalteparin (FRAGMIN®), nadroparin calcium (FRAXIPARIN®), tinzaparin (INNOHEP), and ardeparin (NORMIFLO®).

Necuparanib (M402; Momenta Pharmaceuticals), a heparin sulfate mimetic derived from unfractionated heparin, is a novel oncology drug candidate engineered to have a broad range of effects on tumor cells. Unlike conventional heparin and fractionated derivatives, necuparanib has limited anticoagulative properties, thus increasing the maximum dose which may be administered. Necuparanib has been tested in a two part phase-I/II proof-of-concept trial in patients with advanced metastatic pancreatic cancer. Part A is an open label multiple ascending dose escalation study of necuparanib dosed in conjunction with the standard-of-care regimen of abraxane plus gemcitabine. In certain embodiments, the formulation contains between about 5 mg/mL to about 1,000 mg/mL necuparanib, between about 50 mg/mL to about 750 mg/mL necuparanib, between about 100 mg/mL to about 500 mg/mL necuparanib, or between about 250 mg/mL to about 500 mg/mL necuparanib.

Enoxaparin sodium (LOVENOX®) is a low-molecular weight heparin having an average molecular weight is about 4,500 Da. Enoxaparin sodium is administered by either subcutaneous or intravenous injection. It is available in concentrations of 100 mg/mL and 150 mg/mL.

Dalteparin sodium (FRAGMIN®, Eisai, Inc.), is a low-molecular weight heparin having an average molecular weight between about 3,000 to 8,000 Da. Dalteparin sodium is administered by subcutaneous injection. It is available in concentrations of 64 mg/mL and 160 mg/mL, in a total volume of 0.1 mL water for injection.

Nadroparin calcium (FRAXIPARINE®, GlaxoSmithKline, plc), is a low-molecular weight heparin having an average molecular weight is about 4,300 Da. Nadroparin calcium is administered by subcutaneous injection. FRAXIPARINE® prefilled syringes contain nadroparin calcium at a concentration of 9,500 anti-Xa IU/mL. FRAXIPARINE FORTE® prefilled syringes contain nadroparin calcium at a concentration of 19,000 anti-Xa IU/mL.

Tinzaparin sodium (INNOHEP®, Leo Pharmaceuticals, Inc.), is a low-molecular weight heparin having an average molecular weight between about 5,500 and about 7,500 Da. Tinzaparin sodium is administered by subcutaneous injection. Tinzaparin is available in a multiple dose 2 mL vial containing 20,000 IU/mL.

Ardeparin (NORMIFLO®) is a low-molecular weight heparin having an average molecular weight between about 5,500 and 6,500 Da. Ardeparin is available for injection in 5,000 or 10,000 IU/0.5 mL.

2-O, 3-O Desulfated heparin (ODSH) is a heparin derivative in which the 2-O and 3-O sulfate groups of heparin are removed. ODSH has potential anti-inflammatory and antineoplastic activities, but reduced anticoagulative properties. Upon administration, ODSH prevents the interaction of the receptor for advanced glycation end-products (RAGE) to its ligands. In addition, this agent inhibits the enzymes heparanase, cathepsin G, and human leukocyte elastase, which are involved in inflammation and metastasis. ODSH also inhibits selectins, thereby preventing the adhesion of tumor cells to endothelium and platelets. Altogether, this may inhibit tumor cell invasiveness and metastasis. Unlike heparin, this agent does not cause heparin-induced thrombocytopenia (HIT).

Other non-anticoagulant heparins can be obtained either by removing chains containing the antithrombin-binding sequence, or by inactivating critical functional groups or units of this sequence. The non-anticoagulant heparins most extensively studied are regioselectively desulfated heparins and 'glycol-split' heparins. Some modified heparins of both types are potent inhibitors of heparanase. A number of them also attenuate metastasis in experimental models. Non-anticoagulant heparins are preferable for potential clinical use because they can be administered at high doses without triggering an anticoagulant effect. Heparin and non-anticoagulant heparins also inhibit selectin-mediated cell-cell interactions thus preventing extravasation of blood-borne cells.

Sulodexide (SULONEX®, Keryx Biopharmaceuticals) is a mixture of glycosaminoglycans (GAGs) composed of dermatan sulfate (DS) and fast-moving heparin (FMH). The low molecular weight of both sulodexide fractions allows for extensive oral absorption compared to unfractionated heparin. The pharmacological effects of sulodexide differ substantially from other glycosaminoglycans and are mainly characterized by a prolonged half-life and reduced effect on global coagulation and bleeding parameters.

Acarbose (PRECOSE®, Bayer Pharmaceuticals) retards the digestion and absorption of carbohydrates in the small intestine and hence reduces the increase in blood-glucose concentrations after a carbohydrate load. It is given orally to non-insulin dependent diabetes mellitus patients where diet modification or oral hypoglycemic agents do not control their condition.

Fondaparinux sodium (ARIXTRA®, GlaxoSmithKline, plc) is a synthetic pentasaccharide anticoagulant. Fondaparinux administered subcutaneously as a 5 mg/1 mL solution.

The polysaccharides heparin, enoxaparin, dalteparin, nadroparin, tinzaparin, and delingoparin, ODSH, non-anticoagulating heparin, and sulodexide have been tested in clinical trials for efficacy in conditions such as infertility, inhalation injury, inflammation, vulvodynia, ulcerative colitis, diabetic foot ulcers, pregnancy complications, burns, cystic fibrosis, pulmonary conditions, labor, microalbuminuria, and breast, colorectal, lung, prostate, and vasoocclusive cancers, as well as adenocarcinoma of the colon (Page, ISRN Pharmacology, 2013, 2013:1-13).

Cylexin (CY-1503) is an analog of the sialyl-Lewis$^X$ antigen. Cylexin was tested by Cytel Corporation in a clinical trial related to cardiovascular injury. Cylexin was also tested in a double-blind, randomized, placebo-controlled, parallel study involving 53 patients with operable, chronic thromboembolic pulmonary hypertension (CTEPH) (Kerr et al., American Journal of Respiratory and Critical Care Medicine, 2000, 162:14-20).

Rivipansel (GMI-1070) is an antagonist of E-, P-, and L-selectins and has been tested in a phase II clinical trial by GlycoMimetics, Inc., for vaso-occlusive crisis in sickle cell disease.

The polysaccharide GSC-150 is an antagonist of E-, P-, and L-selectins and has been investigated for its anti-metastatic effect by Kanebo, Ltd.

Various glycomimetic compounds have also been explored, including those of the natural polysaccharides manα(1-2)man and Lewis$^x$, which have been studied for their improved affinity to DC-SIGN. These glycomimetics may be used as DC-SIGN antagonists. Glycomimetics of the naturally occurring ganglioside GQ1bα have been studied for improved affinity to myelin-associated glycoprotein (MAG). The GQ1bα glycomimetics may be used as MAG antagonists to promote neuron regeneration and nerve repair. Glycomimetic compounds based on Lewis$^a$ trisaccharide Galβ(13)[Fucα(14)]GlcNAc, which is a high affinity ligand for *Pseudomonas aeruginosa* virulence factor PAIIL, have been developed for use against bacterial infections as high affinity microbial anti-adhesins. These polysaccharides, among others, are described by Ernst et al., *Nature Reviews Drug Discovery* 2009, 8(8):661-77.

b. Polysaccharides for Biomaterials and Drug Delivery

In other embodiments, the reduced-viscosity formulation may contain a polysaccharide used for biomaterials and/or drug delivery. By reducing viscosity of these formulations, they may be more accurately placed in tight junctions, or formulated with other agents at concentrations unattainable without the viscosity-reducing additives.

Chondroitin sulfate (formerly called a mucopolysaccharide) is found in cartilage, bone, blood vessels, and connective tissues. There are two forms: chondroitin sulfate A and chondroitin sulfate C. One or both types accumulate abnormally in several of the mucopolysaccharidosis disorders. Chondroitin sulfate contains N-acetyl galactosamine alternating with glucuronic acid to form the disaccharide repeating unit of polymer. Chondroitin sulfate consists of a chain of about 40 repeating units of N-acetyl chondrosine sulfate with about 80 anionic charges. Chondroitin sulfate is the most prevalent of the glycoaminoglycan in cartilage. Chondroitin sulfate B is called dermatan sulfate.

Dermatan sulfate (formerly called a mucopolysaccharide) is found mostly in skin but also in blood vessels, the heart valves, tendons, and the lungs. Dermatan sulfate accumulates abnormally in several of the mucopolysaccharidosis disorders.

Keratin sulfate is a disaccharide repeating unit consisting of N-acetyl glucosamine alternating with galactose. It has variable chain length and variable degree of sulfonation. Keratin sulfate is present in low levels in fetal & newborn cartilage, but the concentration rises with maturation up to 55% of total glycosaminoglycan content of the tissue. Morquio's Syndrome is a disorder characterized by excessive accumulation of keratin sulfate in the tissues.

Hyaluronic acid (hyaluronan or hyaluronate) is an anionic non-sulfated GAG. The term hyaluronate also refers to the conjugate base of hyaluronic acid. Because the molecule typically exists in vivo in its polyanionic form, it is most commonly referred to as hyaluronan. It is a visco-elastic polymer normally found in the aqueous and vitreous humour. Sodium hyaluronate (ORTHOVISC®) is a viscous solution consisting of a high molecular weight (500-700 kDa) fraction of purified natural sodium hyaluronate in buffered physiological sodium chloride. Hyaluronic acid is a natural complex sugar of the glycosaminoglycan family and is a long-chain polymer containing repeating disaccharide units of Na-glucuronate-N-acetylglucosamine.

Sodium hyaluronate occurs naturally on the corneal endothelium, bound to specific receptors for which it has a high affinity. It is also used to treat knee pain in patients with joint inflammation (osteoarthritis). It is usually used in patients who have not responded to other treatments such as acetaminophen, exercise, or physical therapy. Sodium hyaluronate may also be used in plastic surgery to reduce wrinkles on the face or as a filler in other parts of the body. It may be used in ophthalmology to assist in the extraction of cataracts, the implantation of intraocular lenses, corneal transplants, glaucoma filtration, retinal attachment, and in the treatment of dry eyes. Finally, sodium hyaluronate is also used to coat the bladder lining in treating interstitial cystitis. Hyaluronan is similar to a substance that occurs naturally in the joints. It may work by acting as a lubricant and shock absorber in the joint, helping the knee to move smoothly, thereby lessening pain.

Rhamnan sulfate is a naturally occurring rhamnose-containing sulfated polysaccharide with antioxidant, anticoagulant and antiviral biological activities. It is extracted from marine red, green, and brown seaweeds (Patel, *Therapeutic importance of sulfated polysaccharides from seaweeds: updating the recent findings.* 3 Biotech, 2012, 2:171-185; Harada and Maeda, *Chemical structure of antithrombin-active rhamnan sulfate from Monostrom nitidum.* Bioscience, Biotechnology, and Biochemistry, 1998, 62:1647-1652).

In certain embodiments, active agents for use with viscosity-lowering agents include polysaccharides of plant, fungal or animal origin, such as plant- or fungal-derived pectins, galactomannans/mannoglycans, xyloglucans, and beta-glucans/lentinans. In certain embodiments, polysaccharides also include chitosan, alginate, fucoidan, galactan, carrageenan, kappa-carrageenan, galactofucan, mannoglucoronofucan, arabinogalactans, xylomannan sulfate, xylogalactofucan, dextran and derivatives thereof and ulvan. Other examples include compounds such as those described by Chattopadhyay, *International Journal of Polymer Science,* 2010, 2010:1-7; or Patel, 3 *Biotech,* 2012, 2:171-185).

Mannan from *Candida albicans* exhibits certain immunomodulatory properties. In general, these compounds consist mostly of a polysaccharide component but also include proteins (5% by weight). Mannose-binding lectins present on macrophages can bind mannan and activate the host immune system via a nonself-recognition mechanism (Tzianabos, Clinical Microbiology Reviews, 2000, 523-533).

Xyloglucans are polysaccharides that occur in the primary cell walls of all angiosperms (flowering plants) and medicinal mushrooms. Xyloglycans isolated from medicinal mushrooms exhibit antitumor effects (Wasser et al., Critical Reviews in Immunology, 1999, 19:65-96).

Alginate exhibits high capacity for water absorption and is capable of absorbing 200-300 times its own weight in water. Alginate is a linear copolymer with homopolymeric blocks of mannuronate and guluronate residues. Alginate is used in various pharmaceutical preparations as an inactive ingredient, such as in Gaviscon, Bisodol, and Asilone. Alginate is used extensively as an impression-making material in dentistry, prosthetics, lifecasting and occasionally for creating positives for small-scale casting. Alginate is also used as an additive in dehydrated products for slimming aids, and is used by the weight loss industry as an appetite suppressant.

Chitosan is a nontoxic and biodegradable polymer that has antibacterial, antiviral, and antacid properties. Chitosan can also be used for film or fiber formation, or for forming hydrogels. (Chattopadhyay et al., International Journal of Polymer Science, 2010, 2010:1-7).

Fucoidan has been noted for antioxidant, immunostimulatory, lipid lowering, antibacterial, and antihyperpeisic effects. Fucoidan and ulvan are also used in nanomedicine for wound healing, and for in vitro and in vivo controlled drug release (Patel, 3 Biotech, 2012, 2:171-185).

Galactan, carrageenan, and kappa-carrageenan exhibit antioxidant, immunostimulatory, anti-inflammatory, antinociceptive, anticoagulant, and antiviral effects. Galactofucan and mannoglucoronofucan may have antitumor effects. Arabinogalactans may have anticoagulant and antithrombotic effects. Xylomannan sulfate and xylogalactofucan exhibit antiviral effects, particularly against such viruses as influenza, herpes, and human immunodeficiency virus (Patel, 3 Biotech, 2012, 2:171-185).

Dextran is a branched polysaccharide. Both dextran and many of its naturally-occurring and synthetic derivatives exhibit antithrombic activity.

2. Nucleic Acids

Any nucleic acid for therapeutic, diagnostic, clinical, or drug delivery use (collectively referred to herein as functional nucleic acids) can be used in formulations. Functional nucleic acids to be used in formulations can be divided into the following non-limiting categories: copyDNA (cDNA), DNA aptamers, DNAzymes, RNA aptamers, external guide sequences, RNA interference molecules, such as small interfering RNA, antisense RNA, short hairpin RNA, and micro RNA (miRNA), morpholinos, messenger RNA (mRNA), long non-coding RNA (lincRNA), as well as ribozymes, triplex-forming molecules and nucleic acid containing nanoparticles. Therapeutic nucleic acids are capable of modulating functionality of the genes once they arrive within a cell. Introduction of foreign nucleic acid into a cell can be accomplished by viral transduction and non-viral delivery, such as ultrasound, electroporation, lipid-dependent delivery, polypeptide-dependent delivery, calcium co-precipitation, transfection with a "naked" nucleic acid molecule, self-delivering nucleic acid conjugates, and polymer- or glycopolymer-dependent (i.e., polyethyleneimine) delivery in some cases utilizing nanomaterials to shape nucleic acid-containing nano- and micro-particles.

In some embodiments, the nucleic acid is a high molecular weight nucleic acid with a molecular weight of greater than about 10 kDa. In other embodiments the nucleic acid is a low molecular weight nucleic acid with a molecular weight of less than about 10 kDa. In some embodiments, the molecular weight of the polymer is determined by methods known in the art, such as mass spectrometry, and the molecular weight figure is determined using methods known in the art as a number average molecular weight, a weight average molecular weight, or a peak average molecular weight. In some embodiments, the nucleic acid has a molecular weight of about 1-5 kDa, or about 5-10 kDa, or about 5-15 kDa, or about 10-20 kDa.

a. Functional Nucleic Acids i. Antisense

The functional nucleic acids can be antisense molecules. Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation. Alternatively, the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. It is preferred that antisense molecules bind the target molecule with a dissociation constant ($K_d$) less than or equal to $10^{-6}$, $10^{-8}$, $10^{-10}$, or $10^{-12}$.

ii. Aptamers

The functional nucleic acids can be aptamers. Aptamers are DNA or RNA molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000-fold difference in binding affinities between the target molecule and another molecule that differ at only a single position on the molecule. It is preferred that the aptamer have a $K_d$ with the target molecule at least 10-, 100-, 1,000-, 10,000-, or 100,000-fold lower than the $K_d$ with a background binding molecule.

iii. Ribozymes

The functional nucleic acids can be ribozymes. Ribozymes are RNA molecules that are capable of catalyzing a chemical reaction, either intramolecularly or intermolecularly. It is preferred that the ribozymes catalyze inter-molecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

iv. Triplex Forming Oligonucleotides

The functional nucleic acids can be triplex forming molecules. Triplex forming functional nucleic acid molecules are molecules that can interact with either a double-stranded or single-stranded nucleic acid. When triplex molecules interact with a target region, a structure called a triplex is formed in which three strands of DNA form a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

v. External Guide Sequences

The functional nucleic acids can be external guide sequences. External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

vi. RNA Interference

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contain 2 nucleotide overhangs on the 3' ends (Elbashir, et al. (2001) Genes Dev., 15:188-200; Bernstein, et al. (2001) Nature, 409:363-6; Hammond, et al. (2000) Nature, 404: 293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and the antisense strand remains bound to RISC which directs degradation of the complementary mRNA sequence by a combination of endo and exonucleases (Martinez, et al. (2002) Cell, 110:563-74). However, the effect of RNAi or siRNA or their use is not limited to any type of mechanism.

A Small Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends.

Sequence specific gene silencing can be achieved in mammalian cells using synthetic, short double-stranded RNAs that mimic the siRNAs produced by the enzyme Dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAs (shRNAs). Kits for the production of vectors containing shRNA are available, such as, for example, Imgenex's GENESUPPRESSOR™ Construction Kits and Invitrogen's BLOCK-IT™ inducible RNAi plasmid and lentivirus vectors.

In some embodiments, the functional nucleic acid is siRNA, shRNA, or micro RNA (miRNA). In some embodiments, the composition includes a vector expressing the functional nucleic acid. Methods of making and using vectors for in vivo expression of functional nucleic acids such as antisense oligonucleotides, siRNA, shRNA, miRNA, EGSs, ribozymes, and aptamers are known in the art.

vii. Other Gene Editing Compositions

In some embodiments the functional nucleic acids are gene editing compositions. Gene editing compositions can include nucleic acids that encode an element or elements that induce a single or a double strand break in the target cell's genome, and optionally a polynucleotide.

b. Strand Break Inducing Elements i. CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for gene editing use (silencing, enhancing or changing specific genes) in eukaryotes (see, for example, Cong, Science, 15:339(6121):819-823 (2013) and Jinek, et al., Science, 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, Science, 15:339(6121):819-823 (2013) and Jinek, et al., Science, 337(6096):816-21 (2012). A single fused crRNA-tracrRNA construct can also be referred to as a guide RNA or gRNA (or single-guide RNA (sgRNA)). Within a sgRNA, the crRNA portion can be identified as the 'target sequence' and the tracrRNA is often referred to as the 'scaffold'.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold), as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

ii. Zinc Finger Nucleases

In some embodiments, the nucleic acid construct or constructs encoding zinc finger nucleases (ZFNs). ZFNs are typically fusion proteins that include a DNA-binding domain derived from a zinc-finger protein linked to a cleavage domain.

The most common cleavage domain is the Type IIS enzyme FokI. FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150, and 5,487,994; as well as Li et al. Proc., Natl. Acad. Sci. USA 89 (1992):4275-4279; Li et al. Proc. Natl. Acad. Sci. USA, 90:2764-2768 (1993); Kim et al. Proc. Natl. Acad. Sci. USA. 91:883-887 (1994a); Kim et al. J. Biol. Chem. 269:31, 978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of Cys2His2 zinc fingers, each of which generally recognizes three to four nucleotides in the target DNA sequence. The Cys2His2 domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

iii. Transcription Activator-Like Effector Nucleases

In some embodiments, nucleic acid construct(s) encode a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD recognizes a specific nucleotide, leading to a simple code for DNA recognition: NI for adenine, HD for cytosine, NG for thymine and NH or NN for guanine. Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TALENs also cleave as dimers, have relatively long target sequences (the shortest reported so far binds 13 nucleotides per monomer), and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, Nucl. Acids Res. 1-11 (2011); US Published Application No. 2011/0145940, which discloses TAL effectors and methods of using them to modify DNA. Miller et al. Nature Biotechnol 29: 143 (2011) reported making TALENs for site-specific nuclease architecture by linking TAL truncation variants to the catalytic domain of FokI nuclease. The resulting TALENs were shown to induce gene modification in immortalized human cells. General design principles for TALEN binding domains can be found in, for example, WO 2011/072246.

c. Gene Altering Polynucleotides

The nuclease activity of the genome editing systems cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

d. Oligonucleotide Composition

The functional nucleic acids can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein "modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

i. Locked Nucleic Acids

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

ii. Peptide Nucleic Acids

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers. In some embodiments, the liquid pharmaceutical formulation of the invention comprises an oligonucleotide composed of peptide nucleic acid. In some embodiments, the liquid pharmaceutical formulation comprises oligonucleotides other than peptide nucleic acids. In some embodiments, the liquid pharmaceutical formulation does not comprise a peptide nucleic acid.

Other backbone modifications include peptide and amino acid variations and modifications. Thus, the backbone constituents of oligonucleotides such as PNA may be naturally occurring and non-naturally occurring peptide linkages. Examples of non-naturally occurring peptide linkages include those in which one or more nitrogen atoms is(are) acetylated, or linkages may include amino spacers such as 8-amino-3,6-dioxaoctanoic acid. Amino acids residues such as lysine are particularly useful if positive charges are desired in the PNA. Methods for the chemical assembly of PNAs are well known. See, for example, U.S. Pat. Nos. 5,539,082, 5,527,675, 5,623,049, 5,714,331, 5,736,336, 5,773,571 and 5,786,571.

iii. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl) pyridine (2-aminopyridine), and various pyrrolo- and pyrazolopyrimidine derivatives.

iv. Sugar Modifications

Oligonucleotides can also contain nucleotides with modified sugar moieties or sugar moiety analogs. Sugar moiety modifications include, but are not limited to, 2'-O-aminoethoxy, 2'-O-aminoethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA).

v. Morpholinos

In some embodiments, the functional nucleic acid is a morpholino oligonucleotide. Morpholino oligonucleotides are typically composed of two or more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5'-exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in an oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high melting temperature, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

vi. Internucleotide Linkages

Modifications to the phosphate backbone of a DNA or RNA oligonucleotide may increase the binding affinity or stability of the oligonucleotide, or reduce the susceptibility of oligonucleotides to nuclease digestion. Cationic modifications, including, but not limited to, diethyl-ethylenediamide (DEED) or dimethyl-aminopropylamine (DMAPA) may be especially useful due to decreased electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable to nucleases in vivo.

Examples of modified nucleotides with reduced charge include modified internucleotide linkages such as phosphate analogs having achiral and uncharged intersubunit linkages (e.g., Sterchak, E. P. et al., Organic. Chem., 52:4202, (1987)), and uncharged morpholino-based polymers having achiral intersubunit linkages (see, e.g., U.S. Pat. No. 5,034, 506), as discussed above. Some internucleotide linkage analogs include morpholidate, acetal, and polyamide-linked heterocycles.

vii. Terminal Residues

Oligonucleotides optionally include one or more terminal residues or modifications at either or both termini to increase stability, and/or affinity of the oligonucleotide for its target. Commonly used positively-charged moieties include the amino acids lysine and arginine, although other positively-charged moieties may also be useful. Oligonucleotides may further be modified to be end capped to prevent degradation using a propylamine group. Procedures for 3' or 5' capping oligonucleotides are well known in the art.

In some embodiments, the functional nucleic acid can be single stranded or double stranded.

e. Nucleic Acid Nanoparticles

Nucleic acid nanoparticles contain oligonucleotides, polynucleotides, single nucleic acid molecules, or a combination thereof. The composition of oligonucleotides, polynucleotides or single nucleic acid molecules can be DNA or RNA nucleotides, LNA, PNA, and/or morpholinos. These nucleic acid compositions may further include heterocyclic bases, sugar modifications, modified internucleotide linkages, and modified terminal residues, as was described in above section titled "Oligonucleotide Compositions". Nucleic acid nanoparticles are well known in the art (see, for example, US 2011/0305734 A1, or US 2012/0263783).

In some embodiments, the nanoparticle compositions may include molecules of varying lengths selected from a non-limiting group of: at least about 2 bases, at least about 5 bases, at least about 10 bases, at least about 50 bases, at least about 100 bases, at least about 500 bases, at least about 750 bases, at least about 1000 bases, at least about 1 kilobases (kb), at least about 5 kb, at least about 10 kb, at least about 50 kb, and longer.

In some embodiments, nanoparticle compositions may include tetrahedral or polyhedral structures. In other embodiments, nanoparticle compositions may include single-layer or multi-layer sheet-like structures (see, for example, Smith et al., Nanomedicine, 2013, 8:105-121).

In some embodiments, nanoparticle compositions may include micellar or liposomal structures (e.g., the nanoparticles are micelles or liposomes). In some embodiments, such structures are crosslinked. In other embodiments, such structures are not crosslinked.

In some embodiments, such nanoparticle compositions further include one or more other biologically active agents in addition to nucleic acids. In some embodiments, nanoparticle compositions are formulated with one or more other components, for example in a pharmaceutical or cosmetic preparation. In some embodiments, such a pharmaceutical or cosmetic preparation is formulated to achieve delivery of nucleic acids (and/or one or more other biologically active agents). In some embodiments, such a pharmaceutical or cosmetic preparation is formulated to achieve delivery (in particular, transdermal delivery) of nucleic acids which have been selected for their activity at the site of biological action. In some embodiments, the nucleic acids have been modified to enhance their activity at the site of biological action.

i. Characteristics of Nanoparticles

In some embodiments, nanoparticle compositions are stable. In some embodiments, nanoparticle compositions are uniform.

In some embodiments, a uniform nanoparticle composition comprises a population of particles whose difference between the minimum and maximum diameters does not exceed approximately 600 nm, approximately 550 nm, approximately 500 nm, approximately 450 nm, approximately 400 nm, approximately 350 nm, approximately 300 nm, approximately 250 nm, approximately 200 nm, approximately 150 nm, or approximately 100 nm.

In some embodiments, nanoparticles have diameters that are smaller than about 1000 nm, about 600 nm, about 550 nm, about 500 nm, about 450 nm, about 400 nm, about 350 nm, about 300 nm, about 250 nm, about 200 nm, about 150 nm, about 130 nm, about 120 nm, about 115 nm, about 110 run, about 100 nm, about 90 nm, about 80 nm, about 50 nm, or less.

In some embodiments, nanoparticles have a diameter of 1 nm to 1000 nm, 1 nm to 600 nm, 1 nm to 500 nm, 1 nm to 400 nm, 1 nm to 300 nm, 1 nm to 200 nm, 1 nm to 150 nm, 1 nm to 120 nm, 1 nm to 100 nm, 1 nm to 75 nm, 1 nm to 50 nm, or 1 nm to 25 nm. In some embodiments, nanoparticle compositions have a diameter of 1 nm to 15 nm, 15 nm to 200 nm, 25 nm to 200 nm, 50 nm to 200 nm, or 75 nm to 200 nm.

In some embodiments, the total particle distribution is encompassed within the specified range of particle diameter size. In some embodiments, less than 50%, 25%, 10%, 5%, or 1% of the total particle distribution is outside of the specified range of particle diameter sizes. In some embodiments, less than 1% of the total particle distribution is outside of the specified range of particle diameter sizes. In certain embodiments, the nanoparticle composition is substantially free of particles having a diameter larger than 300 nm, 250 nm, 200 nm, 150 nm, 120 nm, 100 nm, 75 nm, 50 nm, or 25 nm.

In some embodiments, nanoparticles within nanoparticle compositions have an average particle size that is under about 300 nm, about 250 nm, about 200 nm, about 150 nm, about 130 nm, about 120 nm, about 115 nm, about 110 nm, about 100 nm, about 90 nm, or about 50 nm. In some embodiments, the average particle size is within the range of about 10 nm to about 300 nm, about 50 nm to about 250 nm, about 60 nm to about 200 nm, about 65 nm to about 150 nm, or about 70 nm to about 130 nm. In some embodiments, the average particle size is about 80 nm to about 110 nm. In some embodiments, the average particle size is about 90 nm to about 100 nm.

In some embodiments, a majority of the nanoparticles within nanoparticle compositions have diameters below a specified size or within a specified range. In some embodiments, the majority is more than 50%, 60%, 70%, 75%, 80%, 85%, 90%, 95%, 96%, 97%, 98%, 99%, 99.5%, 99.6%, 99.7%, 99.8%, 99.9% or more of the particles in the composition.

In some embodiments, a majority of nanoparticles in a nanoparticle composition have diameters between 10 nm and 120 nm. In some embodiments, a majority of nanoparticles in a nanoparticle composition have diameters between 20 nm and 120 nm. In some embodiments, a majority of nanoparticles in a nanoparticle composition have diameters between 20 nm and 110 nm. In some embodiments, a majority of nanoparticles in a nanoparticle composition have diameters between 20 nm and 100 nm. In some embodiments, a majority of nanoparticles in a nanoparticle composition have diameters between 20 nm and 90 nm. In some embodiments, a majority of nanoparticles in a nanoparticle composition have diameters between 20 nm and 80 nm. In some embodiments, a majority of nanoparticles in a nanoparticle composition have diameters between 20 nm and 70 nm. In some embodiments, a majority of nanoparticles in a nanoparticle composition have diameters between 20 nm and 60 nm. In some embodiments, a majority of nanoparticles in a nanoparticle composition have diameters between 20 nm and 50 nm. In some embodiments, a majority of nanoparticles in a nanoparticle composition have diameters between 20 nm and 40 nm. In some embodiments, a majority of nanoparticles in a nanoparticle composition have diameters between 20 nm and 30 nm.

In certain embodiments, about 50% of nanoparticles in a nanoparticle composition have diameters between 10 nm and 40 nm. In certain embodiments, about 90% of nanoparticles in a nanoparticle composition have diameters between 10 nm and 80 nm. In certain embodiments, about 90% of nanoparticles in a nanoparticle composition have diameters between 10 nm and 90 nm. In certain embodiments, about 95% of nanoparticles in a nanoparticle composition have diameters between 10 nm and 110 nm. In certain embodiments, about 95% of nanoparticles in a nanoparticle composition have diameters between 10 nm and 120 nm.

In certain embodiments, about 50% of the aggregate volume of all nanoparticles in a nanoparticle composition comprises or consists of nanoparticles having diameters between 10 nm and 40 nm. In certain embodiments, about 90% of the aggregate volume of all nanoparticles in a nanoparticle composition comprises or consists of nanoparticles having diameters between 10 nm and 80 nm. In certain embodiments, about 95% of the aggregate volume of all nanoparticles in a nanoparticle composition comprises or consists of nanoparticles having diameters between 10 nm and 110 nm. In certain embodiments, about 95% of the aggregate volume of all nanoparticles in a nanoparticle composition comprises or consists of nanoparticles having diameters between 10 nm and 120 nm.

B. Viscosity-Lowering Agents

The viscosity of liquid polysaccharide and nucleic acid formulations, including low-molecular-weight and/or high-molecular-weight polysaccharide and nucleic acids, is reduced by the addition of one or more viscosity-lowering agents (e.g., viscosity-lowering compounds of formulae A-I, A-II, A-III and variations thereof, ionic liquids, organophosphates, water-soluble organic dyes, and other viscosity-lowering compounds described herein). The pharmaceutical formulations may be converted from non-Newtonian to Newtonian fluids by the addition of an effective amount of one or more viscosity-lowering agents.

When employed in a formulation intended for administration to a human or other mammal, the viscosity-lowering agents, like the formulation itself, must be pharmaceutically acceptable. The viscosity-lowering agents are typically organic compounds containing at least one non-carbon, non-hydrogen atom. Preferably, the viscosity-lowering agents contain hydrogen, carbon, oxygen and at least one other type of atom. In certain embodiments, the viscosity-lowering agents are characterized by at least one of the following:

1) organic compounds having at least four carbon and four hydrogen atoms, and at least one sulfur, oxygen, nitrogen, or phosphorus atom;
2) a molecular weight between about 85 and 1,000 Da;
3) the presence of at least one charged, or other hydrophilic, moiety;
4) the presence of at least one, preferably two, and more preferably three, freely rotating bonds;
5) the presence of at least one substituted ring;

6) a molecular polar surface area of at least 24 Å$^2$, preferably at least 50 Å$^2$, and more preferably at least 80 Å$^2$;
7) a molar volume of at least 75 cm$^3$, preferably at least 85 cm$^3$, more preferably at least 100 cm$^3$, and most preferably at least 120 cm$^3$;
8) a polarizability of at least 10 cm$^3$, preferably at least 15 cm$^3$, more preferably at least 20 cm$^3$, and most preferably at least 25 cm$^3$; and
9) the presence of at least one, preferably two, and more preferably three hydrogen bond donors and/or acceptors.

In certain embodiments, the viscosity-lowering agent is characterized by at least two, three, four, five, six, seven, eight or all nine of the above listed attributes. In certain embodiments, the viscosity-lowering agent is further characterized in that it does not contain an aldehyde or carbon-carbon triple bond functional group.

In other embodiments, the viscosity-lowering agent is a combination of two or more compounds, each of which is characterized by at least two, three, four, five, six, seven, eight or all nine of the above listed attributes.

In some embodiments, the viscosity-lowering agents are listed as GRAS by the U.S. Food and Drug Administration ("the FDA"), as of Sep. 30, 2014. "GRAS" is an acronym for the phrase Generally Recognized As Safe. Under sections 201(s) and 409 of the Federal Food, Drug, and Cosmetic Act (the Act), any substance that is intentionally added to food is a food additive and is subject to premarket review and approval by FDA unless the substance is generally recognized, among qualified experts, as having been adequately shown to be safe under the conditions of its intended use, or unless the use of the substance is otherwise excluded from the definition of a food additive. Another source of compounds is the Inactive Ingredient Guide of the FDA (IIG), and equivalents listed by the International Pharmaceutical Excipients Council (IPEC) and the European Medicines Agency (EMA), as of Sep. 11, 2014. The substances used in formulations must be safe for injection. Preferably, the GRAS-listed viscosity-lowering agent is characterized by at least two, three, four, five, six, seven, eight or all nine of the above listed attributes.

In other embodiments, the viscosity-lowering agent is an FDA- or EMA-approved drug product as of Sep. 30, 2014. Like compounds drawn from the GRAS and IIG lists, the toxicity and safety profiles of FDA- and EMA-approved drug products are well established. In addition to lowering the viscosity of the polysaccharide or nucleic acid solution, the use of an FDA- or EMA-approved drug product provides the opportunity for combination therapies. Preferably a FDA- or EMA-approved drug product viscosity-lowering agent is characterized by at least two, three, four, five, six, seven, eight or all nine of the above listed attributes.

1. Viscosity-Lowering Compounds

In some embodiments, the viscosity-lowering agent includes at least one compound of Formula A-I:

Formula A-I

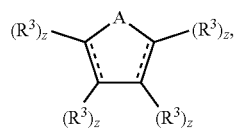

or a pharmaceutically acceptable salt thereof;

wherein each ~~~ independently represents either a single or double bond, A is a selected from O, S, SO$_2$, NR$^3$, C(R$^3$)$_2$, and:

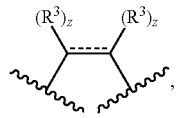

wherein each R$^3$ is independently selected from hydrogen, R$^2$, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^{4a}$, and —N(R$^{4a}$)$_2$;

wherein each R$^2$ is independently selected from C$_{1-12}$alkyl, C$_{3-12}$cycloalkyl, C$_{6-12}$aryl, C$_{1-12}$heteroaryl, and C$_{2-12}$heterocyclyl;

wherein each C$_{1-12}$alkyl may be substituted one or more times with C$_{3-12}$cycloalkyl, C$_{6-12}$aryl, C$_{1-12}$heteroaryl, C$_{2-12}$heterocyclyl, —OH, NH$_2$, (=O), (=NR$^{4a}$), —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each C$_{3-12}$cycloalkyl may be substituted one or more times with C$_{1-12}$alkyl, C$_{6-12}$aryl, C$_{1-12}$heteroaryl, C$_{2-12}$heterocyclyl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each C$_{6-12}$aryl may be substituted one or more times with C$_{1-12}$alkyl, C$_{3-12}$cycloalkyl, C$_{1-12}$heteroaryl, C$_{2-12}$heterocyclyl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each C$_{1-12}$heteroaryl may be substituted one or more times with C$_{1-12}$alkyl, C$_{3-12}$cycloalkyl, C$_{6-12}$aryl, C$_{2-12}$heterocyclyl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each $C_{2-12}$heterocyclyl may be substituted one or more times with $C_{1-12}$alkyl, $C_{3-12}$cycloalkyl, $C_{6-12}$aryl, $C_{1-12}$heteroaryl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)$N(R^{4a})_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)$N(R^{4a})_2$, —$NR^{4a}$C(=O)$N(R^{4a})_2$, —C(=O)$NH_2$, —C(=O)$N(R^{4a})_2$, —$OR^4$, —$SR^4a$, or —$N(R^{4a})_2$;

wherein each $R^4$ is independently selected from $C_{1-12}$alkyl, $C_{3-12}$cycloalkyl, $C_{6-12}$aryl, $C_{1-12}$heteroaryl and $C_{2-12}$heterocyclyl, each of which may be substituted one or more times by —OH, —$NH_2$, —F, —Cl, —Br, —I, —$NO_2$, —CN, —C(=O)OH, —$SO_3H$, —$PO_3H_2$, and —C(=O)$NH_2$;

wherein $R^{4a}$ is $R^4$ or hydrogen;

wherein any two or more of $R^2$, $R^3$, $R^4$, and $R^{4a}$ groups may together form a ring;

wherein when two $R^3$ groups are bonded to the same carbon atom, the two $R^3$ groups may together form an (=O), (=$NR^{4a}$), or (=$C(R^{4a})_2$);

wherein z is in each case independently 1 or 2, provided that when the $(R^3)_z$ substituent is connected to an $sp^2$ hybridized carbon, z is 1, and when the $(R^3)_2$ substituent is connected to an $sp^a$ hybridized carbon, z is 2.

When the substituent is present, it is —$NR^{4a}$C(=$NR^{4a}$)$NR^{4a}$C(=$NR^{4a}$)$N(R^{4a})_2$ is present, it is preferred that $R^{4a}$ is selected so as to give —NHC(=NH)NHC(=NH)$NH_2$.

In certain embodiments, the compound of Formula A-I contains at least one substituent selected from —C(=O)OH, —$SO_3H$, —$SO_2NHC$(=O)$R^4$, and —$PO_3H_2$. In some embodiments, the compound of Formula A-I contains at least one —$SO_3H$ group.

In certain embodiments, one or more of the $R^3$ substituents may be:

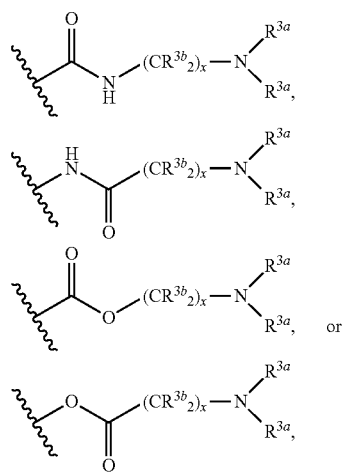

wherein $R^{3a}$ and $R^{3b}$ are independently selected from hydrogen, $C_{1-12}$alkyl, $C_{3-12}$cycloalkyl, $C_{6-12}$ aryl, $C_{1-12}$heteroaryl and $C_{2-12}$heterocyclyl, C(=O)$R^{4a}$, —C(=O)OH, —C(=O)$OR^4$, —$SO_3H$, —$SO_2N(R^{4a})_2$, —$SO_2R^4$, —$SO_2NHC$(=O)$R^4$, C(=O)$NH_2$, —C(=O)$N(R^{4a})_2$, —$OR^4$, —$SR^4$, and —$N(R^{4a})_2$, and when any two $R^{3b}$ are bonded to the same carbon atom, the two $R^{3b}$ groups may together form an (=O), (=$NR^{4a}$), or (=$C(R^{4a})_2$);

wherein each $C_{1-12}$alkyl, $C_{3-12}$cycloalkyl, $C_{6-12}$aryl, $C_{1-12}$heteroaryl and $C_{2-12}$heterocyclyl may be substituted one or more times with —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)$N(R^{4a})_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)$N(R^{4a})_2$, —$NR^{4a}$C(=O)$N(R^{4a})_2$, —C(=O)$NH_2$, —C(=O)$N(R^{4a})_2$, —$OR^4$, —$SR^{4a}$, or —$N(R^{4a})_2$;

wherein $R^4$ and $R^{4a}$ are as defined above;

wherein x is 1, 2, 3, 4, 5, 7, 8, 9 or 10; and wherein any two or more of $R^3$, $R^{3a}$, $R^4$, and $R^{4a}$ groups may together form a ring.

In certain embodiments, the compound of Formula A-I may be represented by either the compound of Formula A-Ia or A-Ib:

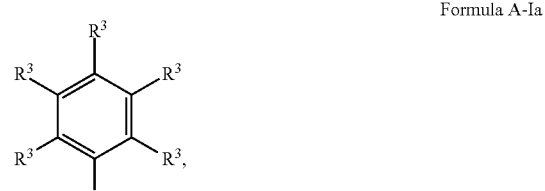

Formula A-Ia

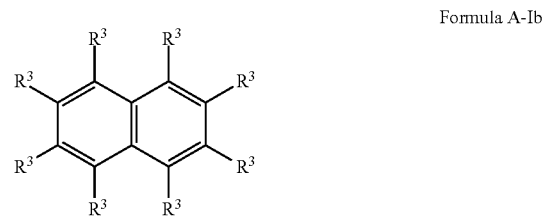

Formula A-Ib wherein each $R^3$ has a meaning given above.

In certain embodiments, the compound of Formula A-Ia may be represented by the compounds of Formulas A-Ia-i to A-Ia-iv:

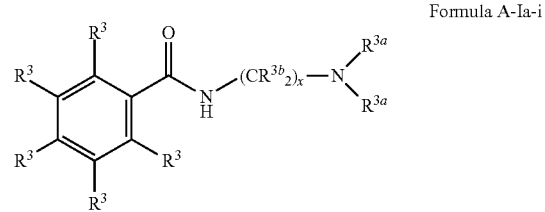

Formula A-Ia-i

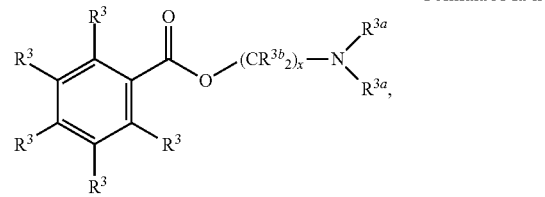

Formula A-Ia-ii

-continued

Formula A-Ia-iii

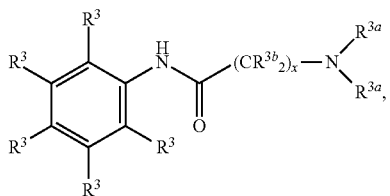

Formula A-Ia-iv

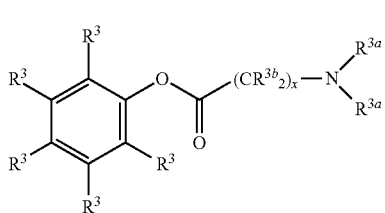

wherein each $R^3$ is independently selected from hydrogen, $NH_2$, $CH_3$, Cl, $OR^4$, and $NHR^4$;
wherein x is 1 or 2;
wherein $R^{3a}$ and $R^{3b}$ are independently selected from hydrogen and $C_{1-12}$ alkyl;
wherein said $C_{1-12}$alkyl may be substituted one or more times by $C_{3-12}$cycloalkyl, $C_{6-12}$aryl, $C_{1-12}$heteroaryl, $C_{2-12}$heterocyclyl, —OH, $NH_2$, —F, —Cl, —Br, —I, —$NO_2$, —CN, —C(=O)$R^{4a}$, —C(=N$R^{4a}$)$R^4$, —C(=O)OH, —C(=O)O$R^4$, —OC(=O)$R^4$, —OC(=O)O$R^4$, —$SO_3H$, —$SO_2$N($R^{4a}$)$_2$, —$SO_2R^4$, —$SO_2$N$R^{4a}$C(=O)$R^4$, —$PO_3H_2$, —$R^{4a}$C(=N$R^{4a}$)N($R^{4a}$)$_2$, —NHC(=N$R^{4a}$)NH—CN, —N$R^{4a}$C(=O)$R^4$, —N$R^{4a}SO_2R^4$, —N$R^{4a}$C(=N$R^{4a}$)N$R^{4a}$C(=N$R^{4a}$)N($R^{4a}$)$_2$, —N$R^{4a}$C(=O)N($R^{4a}$)$_2$, —C(=O)$NH_2$, —C(=O)N($R^{4a}$)$_2$, —$OR^4$, —$SR^{4a}$, or —N($R^{4a}$)$_2$;
$R^4$ and $R^{4a}$ are as defined above; and
wherein any two or more $R^{3a}$, $R^{3b}$, $R^4$, and $R^{4a}$ may together form a ring.

The compound of Formula A-I may be represented by the compound of Formula A-Ia-v, vi, or vii:

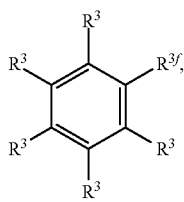

(A-Ia-v)

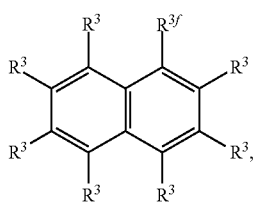

(A-Ia-vi)

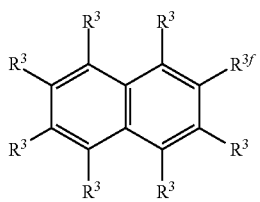

(A-Ia-vii)

wherein $R^{3f}$ is selected from —C(=O)OH, —$SO_3H$, —$SO_2$NHC(=O)$R^4$, and —$PO_3H_2$, and each $R^3$ is independently as defined above. In certain preferred embodiments, each $R^3$ is independently selected from hydrogen, OH, $NH_2$, $C_{1-6}$alkyl, and COOH.

In other embodiments, the compound of Formula A-I may be represented by any of the compounds of Formulae A-Ic, A-Id, A-Ie or A-If:

Formula A-Ic

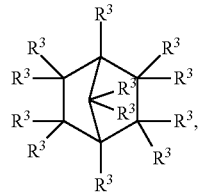

Formula A-Id

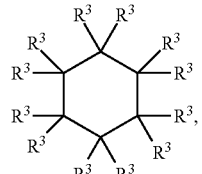

Formula A-Ie

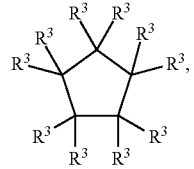

Formula A-If

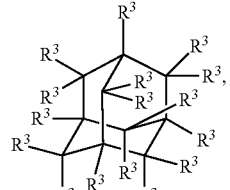

Wherein each $R^3$ has a meaning given above.

In other embodiments, the compound of Formula A-I may be represented by a compound of Formula A-Ig:

Formula A-Ig

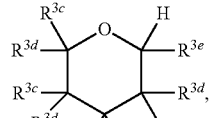

wherein each $R^{3c}$ is independently selected from hydrogen and $R^2$, wherein $R^2$ has a meaning given above;
wherein each $R^{3d}$ is independently selected from hydrogen, OH, $NH_2$, NH($C_{1-6}$alkyl), N($C_{1-6}$alkyl)$_2$, NHC(=O)($C_{1-6}$alkyl), COOH, and $CH_2OH$;
or any two $R^{3c}$ and $R^{3d}$ groups connected to the same carbon may together form an oxo (=O), imino (=N$R^{4a}$), or olefin (=C($R^{4a}$)$_2$), wherein each $R^{4a}$ independently has a meaning given above;
wherein $R^{3e}$ is hydrogen, —OH or $OR^4$; and
wherein each $R^4$ has a meaning given above.

In certain embodiments, the viscosity-lowering agent includes a compound of Formula A-Ig-i:

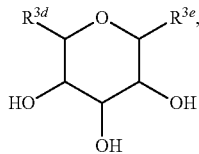

Formula A-Ig-i wherein $R^{3e}$ is selected from OH and —$OC_{1-12}$alkyl, which is further substituted with at least one OH and at least one COOH; and wherein $R^{3d}$ is selected from COOH and $CH_2OH$.

In some embodiments, the viscosity-lowering agent includes a compound of Formula A-II:

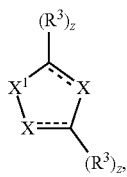

Formula A-II or a pharmaceutically acceptable salt thereof;

wherein each ~~~~ independently represents a single or double bond;

X is independently selected from chalcogen, $N(R^3)_z$, and $C(R^3)_z$;

$X^1$ is absent, or is chalcogen, $N(R^3)_z$, $C(R^3)_z$, or:

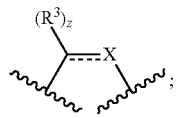

wherein each $R^3$ independently has the meaning given for the compound of Formula A-I;

provided that when the $(R^3)_z$ substituent is connected to an sp$^2$ hybridized nitrogen, z is 0 or 1, when the $(R^3)_z$ substituent is connected to an sp$^2$ hybridized carbon or an sp$^3$ hybridized nitrogen, z is 1, and when the $(R^3)_z$ substituent is connected to an sp$^3$ hybridized carbon, z is 2;

wherein at least one of X or $X^1$ is chalcogen or $N(R^3)_z$.

In certain embodiments, the compound may comprise an aromatic ring. Exemplary compounds comprising aromatic rings include the compounds of Formulas A-IIa-e:

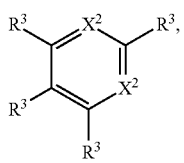

Formula A-IIa

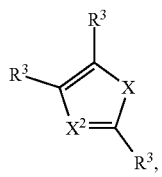

Formula A-IIb

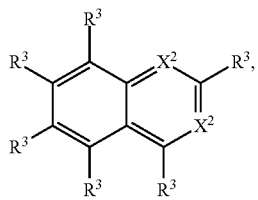

Formula A-IIc

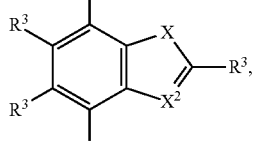

Formula A-IId

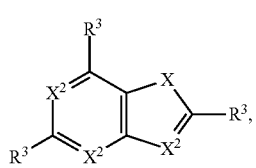

Formula A-IIe

Wherein each $R^3$ and X have a meaning as given for that variable above, and each $X^2$ is independently selected from $N(R^3)_z$ and $C(R^3)_z$.

In certain embodiments, the viscosity-lowering agent is a compound of Formula A-IIa-i:

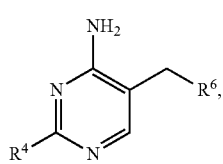

Formula A-IIa-i wherein $R^4$ is as defined above and is preferably hydrogen or $CH_3$;

wherein $R^6$ is $C_{1-12}$heteroaryl, which may be substituted one or more times by $C_{1-6}$ alkyl;

wherein said $C_{1-6}$alkyl may be substituted one or more times by OH, —$NH_2$, —F, —Cl, —Br, —I, —$NO_2$, —CN, —C(=O)$R^4$, —C(=$NR^{4a}$)$R^4$, —C(=O)OH, —C(=O)OR$^4$, —$SO_3H$, —$SO_2NR^4$—, —$SO_2R_4$, —$PO_3H_2$, —NHC(=O)$R^4$, —NHC(=O)N($R^4$)$_2$, —C(=O)$NH_2$, —C(=O)N($R^4$)$_2$, —OR$^{4b}$, —SR$^{4b}$, or —N($R^{4b}$)$_2$, wherein $R^4$ has the meanings given above; or

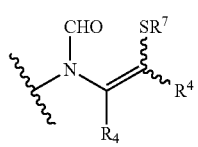

wherein $R^4$ is as defined above, and $R^7$ is selected from $SR^4$ and —C(═O)$R^4$. The double bond in the group above may be in either the E or Z geometry.

In preferred embodiments, $R^6$ is a heterocycle having the structure:

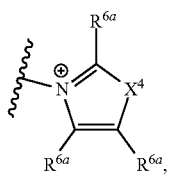

wherein $X^4$ is a chalcogen and $R^{6a}$ is hydrogen or $C_{1-6}$alkyl, wherein the $C_{1-6}$alkyl may be substituted one or more times by —OH, —NH$_2$, —F, —Cl, —Br, —I, —NO$_2$, —CN, or —C(═O)OH. In an even more preferred embodiment, $R^6$ is a heterocycle having the structure:

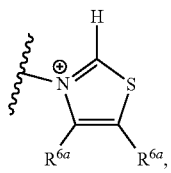

wherein $R^{6a}$ is selected from unsubstituted $C_{1-6}$alkyl and $C_{1-6}$alkyl substituted one or more times with —OH.

The viscosity-lowering agent may be an imidazole of Formula A-IIb-i

Formula A-IIb-i

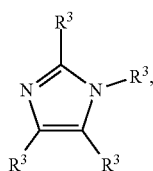

Wherein each $R^3$ is independently as defined above. In certain embodiments, each $R^3$ is independently selected from hydrogen, NO$_2$, and $R^4$. In certain preferred embodiments, the compound of Formula A-IIb-i has the structure:

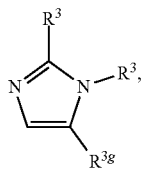

Wherein each $R^3$ is independently selected from $C_{1-6}$ alkyl, which may be unsubstituted or substituted one or more times with a group selected from OH, NH$_2$, $SR^4$, F, Cl, Br and I; and $R^{3g}$ is either hydrogen or NO$_2$.

In other embodiments, the viscosity-lowering agent has the structure of Formula A-IIa-ii or Formula A-IIc-i:

Formula A-IIa-ii

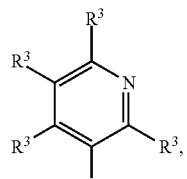

Formula A-IIc-i

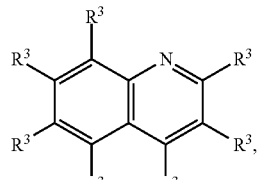

Wherein each $R^3$ is independently selected from OH, Cl, Br, F, I, N($R^{4a}$)$_2$, C(═O)OH, and C(═O)NH$_2$.

In further embodiments, at least one $R^3$ substituent is NHR$^4$, wherein $R^4$ is a $C_{1-6}$alkyl, optionally substituted by one or more groups selected from Cl, Br, F, I, OH, C(═O)OH, NH$_2$, NH($C_{1-6}$alkyl), and N($C_{1-6}$alkyl)$_2$.

In other embodiments, the viscosity-lowering agent is a pyridinium salt of Formula A-IIa-iii:

Formula A-IIa-iii

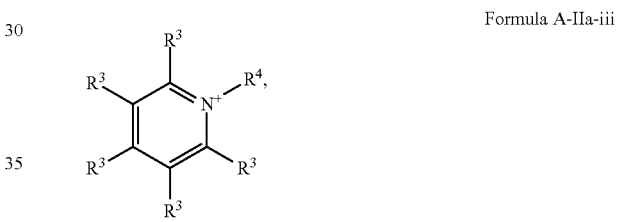

wherein $R^3$ and $R^4$ are as defined above.

In other embodiments, the viscosity-lowering agent comprises a heterocyclic ring that is not a heteroaryl ring. Exemplary non-aromatic rings include the compounds of Formulas A-IIf to A-IIk:

Formula A-IIf

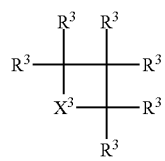

Formula A-IIg

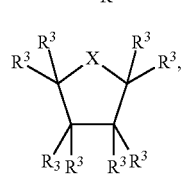

Formula A-IIh

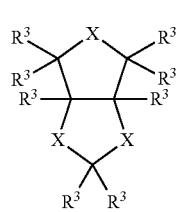

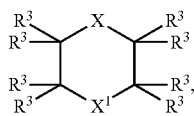
Formula A-IIi

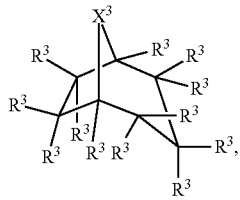
Formula A-IIj

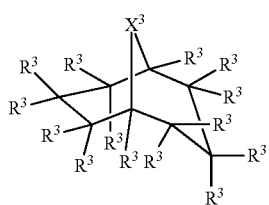
Formula A-IIk wherein each $R^3$, X, and $X^1$ have a meaning described above, and $X^3$ is chalcogen or $N(R^3)_z$, In certain embodiments, the compound of Formula A-IIf is a beta-lactam of Formula A-IIf-i,

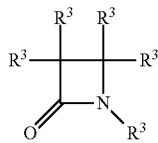
Formula A-IIf-i wherein each $R^3$ is independently as defined herein.

The beta lactam of Formula A-IIf-i includes penicillin-type compounds, as well cephalosporin-type and cephamycin-type compounds of the Formula A-IIf-ii and A-IIf-iii:

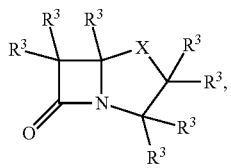
Formula A-IIf-ii

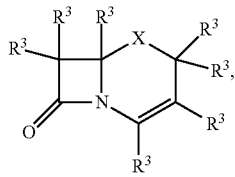
Formula A-IIf-iii wherein X and each $R^3$ are independently as defined above. In preferred embodiments, X is sulfur.

In certain embodiments, the compound of Formula A-IIi is a compound of Formula A-IIi-i:

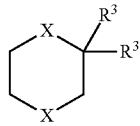
Formula A-IIi-i

Wherein each X and each $R^3$ are independently as defined above. In certain embodiments, X is in both cases $NR^4$, wherein each $R^4$ independently has a meaning given above, and $R^3$ is in both cases hydrogen.

In other embodiments, the compound of Formula A-II is represented by a compound of Formula A-IIi-ii:

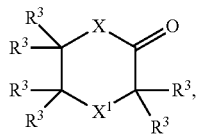
Formula A-IIi-ii wherein X, $X^1$, and each $R^3$ are as defined above.

The compound of Formula A-IIj may be represented by the compound of Formula A-IIj-i:

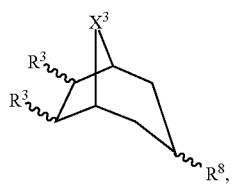
Formula A-IIj-i wherein $X^3$ and each $R^3$ are as defined above, and $R^8$ is selected from $NHC(=O)R^2$ and $OC(=O)R^2$. In preferred embodiments, $X^3$ is $N^+(CH_3)_2$, $R^3$ are both hydrogen, or $R^3$ together form an epoxide or double bond.

The compound of Formula A-IIk may be represented by the compound of Formula A-IIk-i:

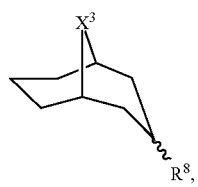
Formula A-IIk-i wherein $X^3$ and $R^8$ are as defined above.

In other embodiments, the viscosity-lowering agent includes a compound of the structure of Formula A-III:

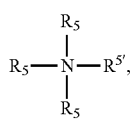
Formula A-III or a pharmaceutically acceptable salt thereof;

wherein $R^5$ is in each case independently selected from hydrogen and $R^2$, $R^5$ is either $R^5$ or absent;

providing that at least one $R^5$ substituent is not hydrogen, and wherein $R^2$ has a meaning given for the compound of Formula A-I.

In certain embodiments, the viscosity-lowering agent is a mixture of two or more compounds selected from compounds of Formula A-I, Formula A-II, Formula A-III and variations thereof described herein.

In preferred embodiments, the viscosity-lowering agent is camphorsulfonic acid (CSA), or a pharmaceutically acceptable salt thereof, such as an alkaline or alkaline earth metal salt. The camphorsulfonic acid or salt thereof is combined with one or more compounds of Formula A-I, A-II, or A-III to give mixtures such as CSA-piperazine, CSA-TRIS, CSA-4-amino pyridine, CSA-1-(o-tolyl)biguanide, CSA-procaine, CSA-Na-aminocyclohexane carboxylic acid, CSA-Na-creatinine, and CSA-Na-ornidazole. Other preferred viscosity-lowering agents include thiamine, procaine, biotin, creatinine, metoclopramide, scopolamine, cimetidine, chloroquine phosphate, mepivacaine, granisetron, sucralose, HEPES-tris, nicotinamide, lactobionic acid-TRIS, glucuronic acid-TRIS, sulfacetamide, CSA-4-aminopyridine, CSA-piperazine, and cefazolin. Any two or more of the viscosity-lowering agents listed above may further be combined in the same formulation.

In other embodiments, the viscosity-lowering agent is an organosulfonic acid. Exemplary organosulfonic acids include, but are not limited to, camphorsulfonic acid, naphthalene-2-sulfonic acid, benzenesulfonic acid, toluenesulfonic acid, cyclohexylsulfonic acid, xylenesulfonic acids (including p-xylene-2-sulfonic acid, m-xylene-2-sulfonic acid, m-xylene-4-sulfonic acid and o-xylene-3-sulfonic acid), methanesulfonic acid, 1,2 ethane disulfonic acid, 4-(2-hydroxyethyl)-1-piperazine ethane sulfonic acid, 2-hydroxyethane-1-sulfonic acid, 3-hydroxypropane-1-sulfonic acid, cymenesulfonic acid, and 4-hydroxybutane-1-sulfonic acid, and pharmaceutically acceptable salts thereof. The organosulfonic acid may be in the form of an alkaline or alkaline earth metal salt, such as lithium, sodium, potassium, magnesium, or calcium salt. The organosulfonic acid (or salt thereof) may be combined with one or more compounds of Formula A-II or Formula A-III.

In certain embodiments, the viscosity-lowering agent contains at least one carboxylic acid. The carboxylic acid may be in the form of an alkaline or alkaline earth metal salt, such as lithium, sodium, potassium, magnesium, or calcium salt. Exemplary carboxylic acid compounds include lactobionic acid, glucuronic acid, 1-aminocyclohexane carboxylic acid, biotin, brocrinat, cyclopentane propionic acid, hydroxynaphthoic acid, phenylpropionic acid, gentisic acid, salicylic acid, camphoric acid, mandelic acid, sulfosalicyclic acid, hydroxybenzoyl benzoic acid, phenyl acetic acid, acetyl salicylic acid, cinnamic acid, t-butyl acetic acid, phthalic acid, trimethylacetic acid, and anthrallic acid, and pharmaceutically acceptable salts thereof. The carboxylic acid (or salt thereof) may be combined with one or more compounds of Formula A-II or Formula A-III.

The following compounds may also be used as viscosity-lowering agents: colistin, articaine, tetracaine, proxymetacaine, metoclopramide, procaine, lidocaine, cyclomethylcaine, piperocaine, chloroprocaine, etidocaine, benzocaine, phenylephrine, bupivacaine, mepivacaine, or cinchocaine, or pharmaceutically acceptable salts thereof, or mixtures thereof.

Other agents which may be employed as viscosity-lowering agents include 1-aminocyclohexane carboxylic acid, 1-(o-tolyl)biguanide, benzethonium chloride, benzoic acid, brocrinat, calcium carrageenan, calcium cyclamate, calcobutrol, caloxetic acid, camphorsulfonic acid, creatinine, dalfampridine, dehydroacetic acid, diazolidinyl urea, dichlorobenzyl alcohol, dimethyl isosorbide, epitetracycline, ethyl maltol, ethyl vanillin, ornidazole, gentisic acid ethanolamide, HEPES (4-(2-hydroxyethyl)-1-piperazine ethane sulfonic acid), gentisic acid, glucuronic acid, iodoxamic acid, menthol, galactose, medronic acid, m-cresol, glutathione, lactobionic acid, maltitol, octisalate, oxyquinoline, pentetic acid, piperazine, propenyl guaethol, propyl gallate, propylene carbonate, propylparaben, protamine sulfate, QUATERNIUM-15, QUATERNIUM-52, satialgine H, sodium 1,2-ethanedisulfonate, sodium cocoyl sarcosinate, sodium lauroyl sarcosinate, sodium polymetaphosphate, sodium pyrophosphate, pyroglutamic acid, sodium trimetaphosphate, sodium tripolyphosphate, sorbitan, tartaric acid, lactic acid, iofetamine, sucralose, 1-(4-pyridyl)pyridinium chloride, aminobenzoic acid, sulfacetamide sodium, naphthalene-2-sulfonic acid, tert-butylhydroquinone, thimerosal, trolamine, tromantadine, vanillin, versetamide, nioxime, niacinamide, methylisothiazolinone, mannose D, maltose, lidofenin, lactose, lactitol, isomalt, imidurea, gluconolactone, methanesulfonic acid, xylenesulfonic acid, and sulfobutylether β-cyclodextrin and pharmaceutically acceptable salts thereof. In some embodiments, the viscosity-lowering agent is sodium trimetaphosphate.

In certain embodiments, the viscosity-lowering agent includes an organic base. Exemplary organic bases include N-methylglucamine, morpholine, piperidine, and primary, secondary, tertiary, and quaternary amines, substituted amines, and cyclic amines. For example, they can be isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, lidocaine, hydrabamine, cholines, betaines, choline, betaine, ethylenediamine, theobromine, purines, piperazine, N-ethylpiperidine, or N-methylpiperidinepolyamine. Particularly preferred organic bases are arginine, histidine, lysine, ethanolamine, thiamine, 2-amino-2-hydroxymethyl-propane-1,3-diol (TRIS), 4-aminopyridine, aminocyclohexane carboxylic acid, 1-o-tolybiguanide, ornidazole, urea, nictoinamide, benzethonium chloride, 5-amino-1-pentanol, 2-(2-aminoethoxy)ethanol, trans-cyclohexane-1,4-diamine, trans-cyclohexane-1R,2R-diamine, ethylenediamine, propane-1,3-diamine, butane-1,4-diamine, pentane-1,5-diamine, hexane-1,6-diamine, octane-1,8-diamine, 5-amino-1-pentanol, 2-(2-aminoethoxy)ethanamine, 2-(2-(2-aminoethoxy)-ethoxy)ethanamine, 3-(4-(3-aminopropoxy)-butoxy)propan-1-amine, 3-(2-(2-(3-aminopropoxy)-ethoxy)-ethoxy)propan-1-amine, N-(2-(2-aminoethylamino)ethyl)ethane-1,2-diamine, N-(2-aminoethyl)ethane-1,2-diamine, N-1-(2-(2-(2-aminoethylamino)ethylamino)-ethyl)ethane-1,2-diamine, N,N-dimethylhexane-1,6-diamine, N,N,N,N-tetramethylbutane-1,4-diamine, phenyltrimethylammonium salts, isopropylamine, diethylamine, ethanolamine, trimethamine, choline, 1-(3-aminopropyl)-2-methyl-1H-imidazole, piperazine, 1-(2-aminoethyl)piperazine, 1-[3-(dimethylamino)propyl]piperazine, 1-(2-aminoethyl)piperidine, or 2-(2-aminoethyl-1-methylpyrrolidine, or a pharmaceutically acceptable salt thereof, or a mixture thereof.

Exemplary beta-lactams include benzylpenicillin (penicillin G), phenoxymethylpenicillin (penicillin V), cloxacillin, dicloxacillin, flucloxacillin, methicillin, nafcillin, oxacillin, temocillin, amoxicillin, ampicillin, mecillinam, carbenicillin, ticarcillin, azlocillin, mezlocillin, piperacillin, cefoxitin, cefazolin, cephalexin, cephalosporin C, cephalothin, cefaclor, cefamandole, cefuroxime, cefotetan, cefixime, cefotaxime, cefpodoxime, ceftazidime, ceftriaxone, cefepime, cefpirome, ceftobiprole, biapenem, doripenem, ertapenem faropenem, imipenem, meropenem, panipenem, razupenem, tebipenem, thienamycin, aztreonam, tigemonam, nocardicin a, tabtoxinine, clavulanic acid, clavulanic acid, tazobactam, or sulbactam, or a pharmaceutically acceptable salt thereof, or a mixture thereof.

Other viscosity-lowering agents include tropane N-heterocycles, such as atropine, hyoscyamine, or scopolamine, or salts thereof, as well as tiotropium and ipratropium salts, thiamine, allithiamine, prosultiamine, fursultiamine, benfotiamine, sulbutiamine, quaternium 15; 1-(3-aminopropyl)-2-methyl-1H-imidazole dihydrochloride; creatinine; biotin, cimetidine, piperocaine, cyclomethylcaine, granisetron, moxifloxacin, chloroquine, mepivacaine, levetriacetam, bupivacaine, cinchocaine, or clindamycin or a pharmaceutically acceptable salt thereof. Thiamine is an especially preferred viscosity-lowering agent.

In certain formulations, the following compounds are not preferred: creatinine, cadaverine, lidocaine, arginine, and lysine, and are excluded from the scope of the foregoing formulas and definitions of useful viscosity-lowering agents.

2. Ionic Liquids

In one aspect, the viscosity-lowering agent is an ionic liquid. In some embodiments, the ionic liquid contains a cationic constituent having a cationic heterocyclic group with one or more alkyl, heteroalkyl, alkenyl, or alkynyl substituents having from 2 to 50 carbon atoms, from 3 to 30 carbon atoms, or from 4 to 12 carbon atoms. Suitable anionic constituents include halide ions, sulfate, sulfonate, sulfite, sulfinate, phosphate, phosphonate, phosphite, phosphonite, carbonate, and carboxylate anions optionally substituted with one or more alkyl, heteroalkyl, alkenyl, alkynyl, carbocyclic, or heterocyclic groups, preferably having from 1 to 20 or from 1 to 12 carbon atoms. Exemplary anionic constituents include chloride, bromide, methylphosphate, methyl-ethyl-phosphate, methylsulfate, methylsulfonate, formate, acetate, butyrate, citrate, carbonate, methyl carbonate, and lactate. The cationic heterocyclic group can be saturated or unsaturated. Saturated cationic heterocyclic groups include pyrrolidinium, oxazolidinium, piperidinium, piperazinium, morpholinium, thiomorpholinium, and azepanium groups, and the like. Unsaturated cationic heterocyclic groups include pyrrolinium, imidazolinium, 1,2,3-triazolium, 1,2,4-triazolium, thiazolium, 1,2,4-dithiazolium, 1,4,2-dithiazolium, tetrazolium, pyrazolinium, oxazolinium, pyridinium, and azepinium groups, and the like. The cationic heterocyclic group can be a fused ring structure having two, three, four, or more fused rings. The cationic heterocyclic group can be a bicyclic cationic heterocycle, such as benzoxazolium, benzothiazolium, benzotriazolium, benzimidazolium, and indolium groups, and the like. The cationic heterocyclic group can be substituted with one or more additional substituents, including hydroxyl and substituted and unsubstituted alkoxy, heteroalkoxy, alkyl, heteroalkyl, alkenyl, and alkynyl groups having from 1 to 30, preferably from 3 to 20 carbon atoms.

The ionic liquid can be 1-butyl-3-methylimidazolium methanesulfonate (BMI Mes) having the structure shown below or a derivative thereof.

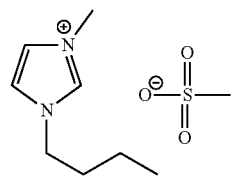

Derivatives of BMI Mes can be obtained, for example, by substituting the methanesulfonate constituent for other anionic constituents, replacing one or more carbons with a heteroatom, replacing the N-butyl or N-methyl group with one or more higher-order N-alkyl groups, attaching additional substituents to one or more carbon atoms, or a combination thereof. Exemplary anionic constituents are described above. Exemplary heteroatoms include N, O, P, and S. Exemplary higher-order N-alkyl groups include substituted and unsubstituted N-alkyl and N-heteroalkyl groups containing from 1 to 30 carbon atoms, preferably from 1 to 12 carbon atoms. Examples of higher-order N-alkyl groups include N-ethyl, N-propyl, N-butyl, N-sec-butyl, and N-tertbutyl. Additional substituents can include hydroxyl and substituted and unsubstituted alkoxy, heteroalkoxy, alkyl, aryl, aralkyl, aryloxy, aralkyloxy, heteroalkyl, alkenyl, and alkynyl groups having from 1 to 30, preferably from 3 to 20 carbon atoms.

The ionic liquid can be 1-butyl-1-methylpyrrolidinium chloride (BMP chloride) having the structure shown below or a derivative thereof.

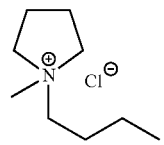

Derivatives of BMP chloride can be obtained, for example, by substituting the chloride constituent for another anionic constituent, replacing one or more ring carbons with a heteroatom, replacing the N,N-butyl-methyl group with one or more higher-order N,N-dialkyl groups, attaching one or more additional substituents to a carbon atom, or a combination thereof. Exemplary anionic constituents include those described above. Exemplary heteroatoms include N, O, P, and S. Exemplary higher-order N,N-dialkyl groups include linear, branched, and cyclic N-alkyl and N-heteroalkyl groups containing from 2 to 30 carbon atoms, preferably from 3 to 12 carbon atoms. Examples of higher-order N,N-dialkyl groups include N-ethyl-N-methyl; N-isopropyl-N-methyl; N-butyl-N-methyl; N,N-diethyl; N-ethyl-N-isopropyl; N,N-diisopropyl groups, and the like. Additional substituents can include hydroxyl, and substituted and unsubstituted alkoxy, heteroalkoxy, alkyl, heteroalkyl, aryl, aryloxy, aralkyl, aralkyloxy, alkenyl, and alkynyl groups having from 1 to 30, preferably from 3 to 20 carbon atoms.

In some embodiments, the ionic liquid contains a cationic constituent having a structure according to Formula B-I where each occurrence of $R^1$ is independently selected from hydrogen and substituted and unsubstituted alkyl, heteroalkyl, aryl, aralkyl, alkenyl, and alkynyl groups having from 1 to 30 carbon atoms, from 3 to 20 carbon atoms, or from 4 to 12 carbon atoms; where each occurrence of $R^2$ is independently selected from hydrogen, halide, hydroxyl, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms, from 3 to 20 carbon atoms, or from 4 to 12 carbon atoms. In some embodiments at least one, at least two, or at least three occurrences of $R^1$ or $R^2$ are not hydrogen.

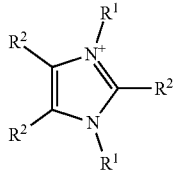

Formula B-I $R^2$ may also be independently selected from hydrogen, $R^1$, —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —$OR^4$, —$SR^4$a, and —N($R^{4a}$)$_2$;

wherein each $R^1$ is independently selected from $C_{1-12}$alkyl, $C_{3-12}$cycloalkyl, $C_{6-12}$aryl, $C_{1-12}$heteroaryl, and $C_{2-12}$heterocyclyl, wherein each $C_{1-12}$alkyl may be substituted one or more times with $C_{3-12}$cycloalkyl, $C_{6-12}$aryl, $C_{1-12}$heteroaryl, $C_{2-12}$heterocyclyl, —OH, $NH_2$, (=O), (=$NR^{4a}$), —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —$OR^4$, —$SR^4$a, or —N($R^{4a}$)$_2$;

wherein each $C_{3-12}$cycloalkyl may be substituted one or more times with $C_{1-12}$alkyl, $C_{6-12}$aryl, $C_{1-12}$heteroaryl, $C_{2-12}$heterocyclyl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —$OR^4$, —$SR^4$a, or —N($R^{4a}$)$_2$;

wherein each $C_{6-12}$aryl may be substituted one or more times with $C_{1-12}$alkyl, $C_{3-12}$cycloalkyl, $C_{1-12}$heteroaryl, $C_{2-12}$heterocyclyl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —$OR^4$, —$SR^4$a, or —N($R^{4a}$)$_2$;

wherein each $C_{1-12}$heteroaryl may be substituted one or more times with $C_{1-12}$alkyl, $C_{3-12}$cycloalkyl, $C_{6-12}$aryl, $C_{2-12}$heterocyclyl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$) NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —$OR^4$, —$SR^4$a, or —N($R^{4a}$)$_2$;

wherein each $C_{2-12}$heterocyclyl may be substituted one or more times with $C_{1-12}$alkyl, $C_{3-12}$cycloalkyl, $C_{6-12}$aryl, $C_{1-12}$heteroaryl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)$OR^4$, —OC(=O)$R^4$, —OC(=O)$OR^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$) $NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —$OR^4$, —$SR^4$a, or —N($R^{4a}$)$_2$;

each $R^4$ is independently selected from $C_{1-12}$alkyl, $C_{3-12}$cycloalkyl, $C_{6-12}$aryl, $C_{1-12}$heteroaryl and $C_{2-12}$heterocyclyl, each of which may be substituted one or more times by —OH, —$NH_2$, —F, —Cl, —Br, —I, —$NO_2$, —CN, —C(=O)OH, —$SO_3H$, —$PO_3H_2$, or —C(=O)$NH_2$;

each $R^{4a}$ is independently $R^4$ or hydrogen;

wherein any two or more of $R^2$, $R^3$, $R^4$ and $R^{4a}$ groups may together form a ring.

In some embodiments, the ionic liquid contains a cationic constituent having a structure according to Formula B-II:

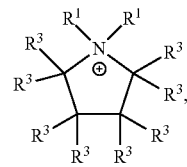

Formula B-II wherein $R^1$ as defined above and each $R^3$ is either $R^2$ as defined above, or two $R^3$ substituents on the same carbon atom may together form a (=O), (=$NR^{4a}$) or (=$CR^2_2$). The ionic liquid may also contain a cationic constituent having the structure according to Formula B-III:

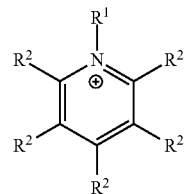

Formula B-III wherein $R^1$ and $R^2$ are as defined above.

In some embodiments, the ionic liquid contains a cationic constituent having a structure according to Formula B-IV:

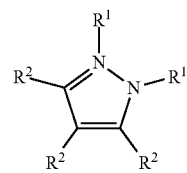

Formula B-IV wherein $R^1$ and $R^2$ are as defined above.

In some embodiments, the ionic liquid contains a cationic constituent having a structure according to any one of Formulas B-V-IX, where each occurrence of A is independently selected from C, N, O, S, and P; where each dashed line (- - -) is independently a single, double, or triple bond; and where each $R^{10}$ and $R^{10'}$, when taken separately, is independently absent or selected from H, hydroxyl, halide, and substituted and unsubstituted alkoxy, heteroalkoxy, alkyl, aryl, heteroalkyl, alkenyl, and alkynyl groups having from 1 to 30 carbon atoms, from 2 to 20 carbon atoms, or from 3 to 12 carbon atoms or, when attached to the same atom and taken together, each $R^{10}$ and $R^{'}$ is =O or together with the atom to which they are attached form a carbocycle or heterocycle having from 2 to 30, preferably from 3 to 12 carbon atoms; so long as at least one occurrence of A has a formal positive charge. In preferred embodiments, at least one occurrence of $R^{10}$ or $R^{'}$ has at least two, at least three, at least four, or at least five carbon atoms. Exemplary alkyl groups include ethyl, propyl, isopropyl, butyl, tert-butyl, hexyl, octyl, and decyl groups. Exemplary heteroalkyl groups include cyanoethyl, cyanobutyl, and cyanopropyl groups. Exemplary alkoxy groups include methoxy, ethoxy, and butoxy groups.

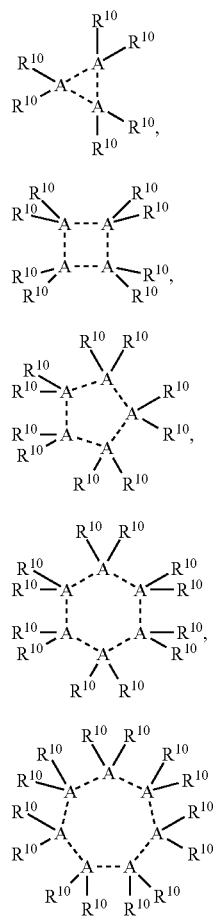

Formula B-V

Formula B-VI

Formula B-VII

Formula B-VIII

Formula B-IX

In some embodiments, the ionic liquid contains a cationic constituent having a structure according to any one of Formulas B-V-IX where at least one occurrence of A is a nitrogen atom having a formal positive charge with the remaining A each independently selected from C, N, O, S, and P; each dashed line (- - -) is independently a single or double bond; and where each $R^{10}$ and $R^{'}$, when taken separately, is independently absent or selected from H, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms, from 2 to 20 carbon atoms, or from 3 to 12 carbon atoms or, when attached to the same atom and taken together, each $R^{10}$ and $R^{'}$ is =O or together with the atom to which they are attached form a carbocycle or heterocycle having from 1 to 30, preferably from 3 to 12 carbon atoms. In preferred embodiments at least one occurrence of $R^{10}$ or $R^{'}$ has at least two, at least three, at least four, or at least five carbon atoms. Exemplary alkyl groups include ethyl, propyl, butyl, hexyl, octyl, and decyl groups, as well as isomers thereof. Exemplary heteroalkyl groups include cyanobutyl and cyanopropyl groups. Exemplary alkoxy groups include methoxy, ethoxy, and butoxy groups.

The ionic liquid can be an ammonium salt of Formula B-X:

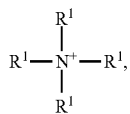

Formula B-X wherein $R^1$ is as defined above.

In some embodiments, the ionic liquid contains a cationic constituent having a structure according to Formula B-XI where Ar is a substituted or unsubstituted aryl group; $R^{12}$ is either absent or is an alkyl, heteroalkyl, aryl, aralkyl, alkenyl, or alkynyl group having from 1 to 30 carbon atoms, from 3 to 20 carbon atoms, or from 4 to 12 carbon atoms; and each occurrence of $R^1$ is independently selected from hydrogen and substituted and unsubstituted alkyl, heteroalkyl, aryl, aralkyl, alkenyl, and alkynyl groups having from 1 to 30 carbon atoms, from 3 to 20 carbon atoms, or from 4 to 12 carbon atoms. In some embodiments, the ionic liquid contains a cationic constituent having a structure according to Formula B-XI where Ar is a substituted or unsubstituted benzyl group; where $R^{12}$ is a substituted or unsubstituted $C_1$-$C_{12}$ alkyl group, or both. In some embodiments, the compound of Formula B-XI is characterized by the presence of at least one group selected from —COOH, —SO$_3$H, and —PO$_3$H$_2$.

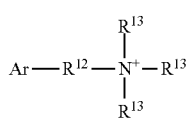

Formula B-XI

The ionic liquid can be a phosphonium salt. In some embodiments, the ionic liquid contains a cationic constituent having a structure according to Formula B-XII where each occurrence of $R^{14}$ is independently selected from hydrogen and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms, from 3 to 20 carbon atoms, or from 4 to 12 carbon atoms; wherein at least one, at least two, or at least three occurrences of $R^{14}$ are not hydrogen. In some embodiments, at least one occurrence of $R^{14}$ is an aryl, aralkyl, or aralkoxy group having from 2 to 30 carbon atoms or from 4 to 12 carbon atoms. In some embodiments, the compound of Formula B-XII is characterized by the presence of at least one group selected from —COOH, —$SO_3H$, and —$PO_3H_2$.

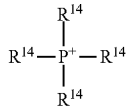

Formula B-XII

In some embodiments, the ionic liquid contains a cationic constituent having a structure according to Formula B-XIII where Ar is a substituted or unsubstituted aryl group; $R^{15}$ is either absent or is an alkoxy, heteroalkoxy, alkyl, heteroalkyl, aryl, aryloxy, aralkyl, aralkyloxy, alkenyl, or alkynyl group having from 2 to 30 carbon atoms, from 3 to 20 carbon atoms, or from 4 to 12 carbon atoms; and each occurrence of $R^{16}$ is independently selected from hydrogen and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms, from 3 to 20 carbon atoms, or from 4 to 12 carbon atoms. In some embodiments, the ionic liquid contains a cationic constituent having a structure according to Formula B-XIII where Ar is a substituted or unsubstituted benzyl group; where $R^{15}$ is a substituted or unsubstituted $C_1$-$C_{12}$ alkyl group, or both. In some embodiments, the compound of Formula B-XIII is characterized by the presence of at least one group selected from —COOH, —$SO_3H$, and —$PO_3H_2$.

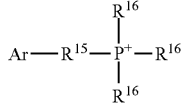

Formula B-XIII

The ionic liquid can be a guanidinium salt having a structure according to Formula B-XIV:

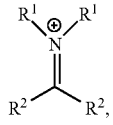

Formula B-XIV wherein $R^1$ and $R^2$ are as defined above.

The ionic liquid can be a salt having a structure according to Formula B-XV:

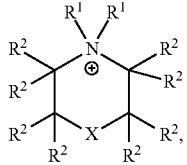

Formula B-XV wherein $R^1$ and $R^2$ are as defined above, and X may be O, S, $SO_2$, $NR^1$ or $C(R^2)_2$.

The ionic liquid can be an imidazolium salt such as 1-allyl-3-methylimidazolium bis(trifluoromethylsulfonyl); 1-allyl-3-methylimidazolium bromide; 1-allyl-3-methylimidazolium chloride; 1-allyl-3-methylimidazolium dicyanamide; 1-allyl-3-methylimidazolium iodide; 1-benzyl-3-methylimidazolium chloride; 1-benzyl-3-methylimidazolium hexafluorophosphate; 1-benzyl-3-methylimidazolium tetrafluoroborate; 1,3-bis(cyanomethyl)imidazolium bis(trifluoromethylsulfonyl)imide; 1,3-bis(cyanomethyl)imidazolium chloride; 1-butyl-2,3-dimethylimidazolium chloride; 1-butyl-2,3-dimethylimidazolium hexafluorophosphate; 1-butyl-2,3-dimethylimidazolium tetrafluoroborate; 1-butyl-3-methylimidazolium acetate; 1-butyl-3-methylimidazolium bis(trifluoromethylsulfonyl)imide; 1-butyl-3-methylimidazolium bromide; 1-butyl-3-methylimidazolium chloride; 1-butyl-3-methylimidazolium dibutyl phosphate; 1-butyl-3-methylimidazolium dicyanamide; 1-butyl-3-methylimidazolium hexafluoroantimonate; 1-butyl-3-methylimidazolium hexafluorophosphate; 1-butyl-3-methylimidazolium hydrogen sulfate; 1-butyl-3-methylimidazolium iodide; 1-butyl-3-methylimidazolium methanesulfonate; 1-butyl-3-methyl-imidazolium methyl carbonate; 1-butyl-3-methyl-imidazolium methyl sulfate; 1-butyl-3-methylimidazolium nitrate; 1-butyl-3-methylimidazolium octyl sulfate; 1-butyl-3-methylimidazolium tetrachloroaluminate; 1-butyl-3-methylimidazolium tetrafluoroborate; 1-butyl-3-methylimidazolium thiocyanate; 1-butyl-3-methylimidazolium tosylate; 1-butyl-3-methylimidazolium trifluoromethanesulfonate; 1-(3-cyanopropyl)-3-methylimidazolium bis(trifluoromethylsulfonyl)amide; 1-(3-cyanopropyl)-3-methylimidazolium chloride; 1-(3-cyanopropyl)-3-methylimidazolium dicyanamide; 1-decyl-3-methylimidazolium; 1-decyl-3-methylimidazolium tetrafluoroborate; 1,3-diethoxyimidazolium bis(trifluoromethylsulfonyl)imide; 1,3-diethoxyimidazolium hexafluorophosphate; 1,3-dihydroxyimidazolium bis(trifluoromethylsulfonyl)imide; 1,3-dihydroxy-2-methylimidazolium bis(trifluoromethylsulfonyl)imide; 1,3-dimethoxyimidazolium bis(trifluoromethylsulfonyl)imide; 1,3-dimethoxyimidazolium hexafluorophosphate; 1,3-dimethoxy-2-methylimidazolium bis(trifluoromethylsulfonyl)imide; 1,3-dimethoxy-2-methylimidazolium hexafluorophosphate; 1,3-dimethylimidazolium dimethyl phosphate; 1,3-dimethylimidazolium methanesulfonate; 1,3-dimethylimidazolium methyl sulfate; 1,2-dimethyl-3-propylimidazolium bis(trifluoromethylsulfonyl)imide; 1-dodecyl-3-methylimidazolium iodide; 1-ethyl-2,3-dimethylimidazolium tetrafluoroborate; 1-ethyl-2,3-dimethylimidazolium chloride; 1-ethyl-2,3-dimethylimidazolium ethyl sulfate; 1-ethyl-2,3-dimethylimidazolium hexafluorophosphate; 1-ethyl-3-methylimidazolium acetate; 1-ethyl-3-methylimidazolium aminoacetate; 1-ethyl-3-methylimidazolium (S)-2-aminopropionate; 1-ethyl-3-methylimidazolium bis(pentafluoroethylsulfonyl)imide; 1-ethyl-3-methylimidazolium bromide; 1-ethyl-3-methylimidazolium chloride; 1-ethyl-3-methylimidazolium dibutyl phosphate; 1-ethyl-3-methylimidazolium dicyanamide; 1-ethyl-3-methylimidazolium diethyl phosphate; 1-ethyl-3-methylimidazolium ethyl sulfate; 1-ethyl-3-methylimidazolium hexafluorophosphate; 1-ethyl-3-methylimidazolium hydrogen carbonate; 1-ethyl-3-methylimidazolium hydrogen sulfate; 1-ethyl-3-methylimidazolium hydroxide; 1-ethyl-3-methylimidazolium iodide; 1-ethyl-3-methylimidazolium L-(+)-lactate; 1-ethyl-3-methylimidazolium methanesulfonate; 1-ethyl-3-methylimidazolium methyl sulfate; 1-ethyl-3-methylimidazolium nitrate; 1-ethyl-3-methylimidazolium tetrachloroaluminate; 1-ethyl-3-methylimidazolium tetrachloroaluminate; 1-ethyl-3-methylimidazolium tetrafluoroborate; 1-ethyl-3-methylimidazolium 1,1,2,2-tetrafluoroethanesulfonate; 1-ethyl-3-methylimidazolium thiocyanate; 1-ethyl-3-methylimidazolium tosylate; 1-ethyl-3-methylimidazolium trifluoromethanesulfonate; 1-hexyl-3-methylimidazolium bis(trifluormethylsulfonyl)imide; 1-hexyl-3-methylimidazolium chloride; 1-hexyl-3-methylimidazolium hexafluorophosphate; 1-hexyl-3-methylimidazolium iodide; 1-hexyl-3-methylimidazolium tetrafluoroborate; 1-hexyl-3-methylimidazolium trifluoromethansulfonate; 1-(2-hydroxyethyl)-3-methylimidazolium dicyanamide; 1-methylimidazolium chloride; 1-methylimidazolium hydrogen sulfate; 1-methyl-3-octylimidazolium chloride; 1-methyl-3-octylimidazolium hexafluorophosphate; 1-methyl-3-octylimidazolium tetrafluoroborate; 1-methyl-3-octylimidazolium trifluoromethanesulfonate; 1-methyl-3-propylimidazolium iodide; 1-methyl-3-propylimidazolium methyl carbonate; 1,2,3-trimethylimidazolium methyl sulfate; derivatives thereof and combinations thereof. Derivatives can include substituting the anionic constituent for other anionic constituents, replacing one or more carbons with a heteroatom, replacing an N-alkyl group with one or more higher-order N-alkyl groups, or a combination thereof. Exemplary anionic constituents and heteroatoms are described above. Exemplary higher-order N-alkyl groups can include linear and branched N-alkyl and N-heteroalkyl groups containing from 1 to 30 carbon atoms, preferably from 2 to 12 carbon atoms. Examples of higher-order N-alkyl groups include N-ethyl, N-propyl, N-isopropyl, N-butyl, N-sec-butyl, and N-tert-butyl.

The ionic liquid can be a pyrrolidinium salt such as 1-butyl-1-methylpyrrolidinium bis(trifluoromethylsulfonyl)imide; 1-butyl-1-methylpyrrolidinium bromide; 1-butyl-1-methylpyrrolidinium chloride; 1-butyl-1-methylpyrrolidinium dicyanamide; 1-butyl-1-methylpyrrolidinium hexafluorophosphate; 1-butyl-1-methylpyrrolidinium iodide; 1-butyl-1-methylpyrrolidinium methyl carbonate; 1-butyl-1-methylpyrrolidinium tetrafluoroborate; 1-butyl-1-methylpyrrolidinium trifluoromethanesulfonate; 1-ethyl-1-methylpyrrolidinium bis(trifluoromethylsulfonyl)imide; 1-ethyl-1-methylpyrrolidinium bromide; 1-ethyl-1-methylpyrrolidinium hexafluorophosphate; 1-ethyl-1-methylpyrrolidinium tetrafluoroborate; derivatives thereof and combinations thereof. Derivatives can include substituting the anionic constituent for other anionic constituents, replacing one or more carbons with a heteroatom, replacing an N-alkyl or N-methyl group with one or more higher-order N-alkyl groups, or a combination thereof. Exemplary anionic constituents, heteroatoms, and higher-order N-alkyl groups are described above.

Zwitterionic Liquids

The ionic liquid can be a zwitterion (i.e., an internal salt), for example, 4-(3-butyl-1-imidazolio)-1-butane sulfonate; 3-(1-methyl-3-imidazolio)propanesulfonate; 4-(3-methyl-1-imidazolio)-1-butanesulfonate; or 3-(triphenylphosphonio)propane-1-sulfonate.

The zwitterionic liquid can be 4-(3-butyl-1-imidazolio)-1-butane sulfonate (BIM) having the structure shown below or a derivative thereof.

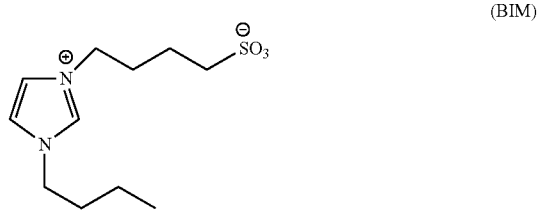

(BIM)

Derivatives of BIM can include substituting the sulfonate group for a different anionic substituent, replacing one or more carbons with a heteroatom, replacing the N-butyl group with one or more lower-order or higher-order N-alkyl groups, attaching additional substituents to one or more carbon atoms, or a combination thereof. Exemplary anionic substituents include sulfate [—OSO$_3^-$], sulfonate [—SO$_3^-$], sulfite [—OSO$_2^-$], sulfinate [—SO$_2^-$], phosphate [—OP(OH)O$_2^-$], alkylphosphate [—OP(OR$^2$)O$_2^-$], phosphonate [—P(OH)O$_2^-$], alkylphosphonate [—P(OR$^2$)O$_2^-$], phosphite [—OP(OH)O$^-$], alkylphosphite [—OP(OR$^2$)O$^-$], phosphonite [—P(OH)O$^-$], alkylphosphonite [—P(OR$^2$)O$^-$], carbonate [—OCO$_2^-$], and carboxylate [—CO$_2^-$], where R$^2$ is as defined above. Exemplary heteroatoms and higher-order N-alkyl groups are described above. Additional substituents can include hydroxyl, and substituted and unsubstituted alkoxy, heteroalkoxy, alkyl, heteroalkyl, aryl, aryloxy, aralkyl, aralkyloxy, alkenyl, and alkynyl groups having from 1 to 30, preferably from 3 to 12 carbon atoms.

In some embodiments, the ionic liquid is a zwitterion containing a cationic heterocyclic substituent and an anionic substituent connected by a substituted or unsubstituted alkyl, heteroalkyl, aryl, aralkyl, alkenyl, or alkynyl group having from 2 to 50 carbon atoms, from 3 to 30 carbon atoms, or from 4 to 12 carbon atoms. The cationic heterocyclic substituent can be saturated or unsaturated. Examples include pyrrolidinium, imidazolinium, oxazolidinium, piperidinium, piperazinium, morpholinium, thiomorpholinium, azepanium, pyrrolinium, 1,2,3-triazolium, 1,2,4-triazolium, thiazolium, 1,2,4-dithiazolium, 1,4,2-dithiazolium, tetrazolium, pyrazolinium, oxazolinium, pyridinium, and azepinium groups. The cationic heterocyclic substituent can be a fused ring structure having two or more fused rings. The cationic heterocyclic substituent can be a bicyclic cationic heterocycle, such as benzoxazolium, benzothiazolium, benzotriazolium, benzimidazolium, and indolium. The cationic heterocyclic substituent can additionally be substituted with one or more additional substituents. Exemplary anionic substituents include sulfate [—OSO$_3^-$], sulfonate [—SO$_3^-$], sulfite [—OSO$_2^-$], sulfinate [—SO$_2^-$], phosphate [—OP(OH)O$_2^-$], alkylphosphate [—OP(OR$^2$)O$_2^-$], phosphonate [—P(OH)O$_2^-$], alkylphosphonate [—P(OR$^2$)O$_2^-$], phosphite [—OP(OH)O$^-$], alkylphosphite [—OP(OR$^2$)O$^-$], phosphonite [—P(OH)O$^-$ ], alkylphosphonite [—P(OR$^2$)O$^-$], carbonate [—OCO$_2^-$], and carboxylate [—CO$_2^-$], where R$^2$ is as described above.

In some embodiments, the ionic liquid is a zwitterion having a structure according to Formula B-XVI, B-XVII, B-XVIII or B-XIV:

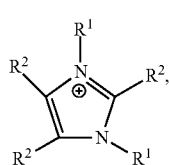

Formula B-XVI

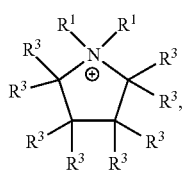
Formula B-XVII

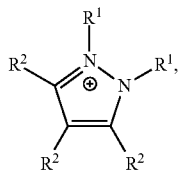
Formula B-XVIII

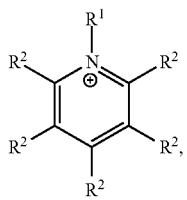
Formula B-XVIV

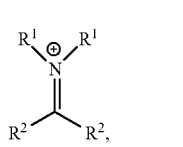
Formula B-XX

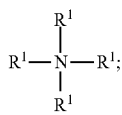
Formula B-XXI wherein $R^1$, $R^2$ and $R^3$ are as defined above, provided that the compounds of Formula B-XVI, B-XVII, B-XVIII, B-XVIV, B-XX and B-XXI each contain at least one —COOH, —SO$_3$H, or —PO$_3$H$_2$ substituent.

3. Organophosphates

In one aspect, the viscosity-lowering agent is an organophosphate. The viscosity of liquid polysaccharide and nucleic acid formulations, including low-molecular-weight and/or high-molecular-weight polysaccharide and nucleic acids, is reduced by the addition of one or more organophosphates. The pharmaceutical formulations are in some cases converted from non-Newtonian to Newtonian fluids by the addition of an effective amount of one or more organophosphates. An "organophosphate" herein is a compound containing one or more phosphoryl groups at least one of which is covalently connected to an organic group through a phosphoester bond. The organophosphate can be a monoester of a phosphoric acid or polyphosphoric acid. The organophosphate can be a diester of a phosphoric acid or polyphosphoric acid. The organophosphate can be a salt or a zwitterion. The term "zwitterion" is used herein to describe an overall neutrally charged chemical molecule which carries formal positive and negative charges on different chemical groups in the molecule.

The organophosphate can be a salt or a zwitterion. The term "zwitterion" is used herein to describe an overall neutrally charged chemical molecule which carries formal positive and negative charges on different chemical groups in the molecule.

When the organophosphate is in the form of a salt, the counter ion may be an alkaline or alkaline earth metal, such as sodium, calcium, lithium, potassium and the like. In other embodiments, the counter ion may be a nitrogen-containing compound, including nitrogen containing compounds having sequential methylene and/or methine groups, benzene, naphthalene, camphor, adamantane, toluene, quinone, anthracene, phenanthrene, pyridine, pyrazine, piperazine, pyrrolidine, piperidine, imidazole, pyrazole, oxazole, thiophene, benzimidazole, or substituted analogs thereof. Exemplary nitrogen-containing compounds include, but are not limited to, L-lysine, L-arginine, L-histidine, pentane-1,5- and hexane-1,6-diamine, adamantylamine, 1-(3-aminopropyl)-2-methyl-1H-imidazole, aminomethylethyl pyrrolidine, dimethylaminopropylpiperazine, aminoethylpiperidine, aminoethylpiperazine, and ethanolamine. For example, the organophosphate can be a salt of thiamine pyrophosphate and 1-(3-aminopropyl)-2-methyl-1H-imidazole, referred to as TPP-APMI.

Although generally any organophosphate may lower the viscosity of a polysaccharide or nucleic acid formulation, in some embodiments the viscosity-reducing organophosphate is a nucleotide or nucleotide derivative or contains a nucleotide or nucleotide derivative. The viscosity-reducing organophosphate can be a nucleotide monophosphate, a nucleotide diphosphate, a nucleotide triphosphate, or a derivative thereof. The viscosity-reducing organophosphate can be a nucleoside monophosphate, a nucleoside diphosphate, a nucleoside triphosphate, or a derivative thereof. The viscosity-reducing organophosphate can contain a nucleobase or a derivative thereof. In some embodiments the viscosity-reducing organophosphate is a conjugate of a nucleobase and a phosphoryl group; a conjugate of a sugar and a phosphoryl group; or a conjugate of a nucleobase, a sugar, and a phosphoryl group. The sugar can be a 5-carbon sugar, a 6-carbon sugar, or a 7-carbon sugar, optionally having one or more substituents. The nucleobase can be purine, adenine, guanine, hypoxanthine, xanthine, 7-methylguanine, pyrimidine, thymine, cytosine, uracil, 5, 6-dihydrouracil, 5-methylcytosine, 5-hydroxymethylcytosine, or a derivative thereof. The nucleoside can be adenosine, guanosine, 5-methyluridine, uridine, cytidine, deoxyadenosine, deoxyguanosine, thymidine, deoxyuridine, deoxycytidine, or a derivative thereof. The nucleotide can be a monophosphate, diphosphate, or triphosphate of any of the nucleosides described above.

The viscosity-reducing organophosphate can have a structure according to Formula C-I wherein X is a phosphate, preferably a diphosphate or triphosphate; Y is absent or a sugar, preferably ribose, deoxyribose, or a derivative thereof; and Z is a nucleobase, preferably one of those described above or a derivative thereof.

Formula C-I

The viscosity-reducing organophosphate can have a structure according to Formula C-II wherein n is an integer from 1 to 20, from 1 to 10, from 2 to 10, or from 2 to 6; wherein $R^1$ is an organic group having from 3 to 50 carbon atoms, from 5 to 30 carbon atoms, or from 7 to 20 carbon atoms, preferably $R^1$ is a nucleobase, a nucleoside, or a derivative thereof; and wherein each occurrence of $R^2$ is independently absent or selected from the group consisting of hydrogen, monovalent cationic groups, and organic groups having from 1 to 50 carbon atoms, from 1 to 30 carbon atoms, from 3 to 30 carbon atoms, or from 7 to 20 carbon atoms. Monovalent cationic groups include potassium, sodium, lithium, ammonium, and alkyl ammonium groups. $R^1$ and $R^2$, whenever $R^2$ is an organic group, can be a substituted or unsubstituted carbocycle or heterocycle having from 3 to 50 carbon atoms, from 5 to 30 carbon atoms, or from 7 to 20 carbon atoms. $R^1$ can be a nucleoside such as one of those described above or a derivative thereof.

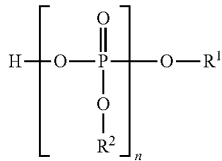

Formula C-II

The viscosity-reducing organophosphate can have a structure according to Formula C-III wherein n is an integer from 1 to 20, from 1 to 10, from 2 to 10, or from 2 to 6; wherein $R^3$ is absent or is a sugar, preferably a monosaccharide or disaccharide, having from 1 to 30 carbon atoms, from 1 to 20 carbon atoms, or from 4 to 20 carbon atoms; wherein $R^4$ is a bulky cyclic group that can be substituted or unsubstituted, preferably a substituted or unsubstituted carbocycle or heterocycle having from 3 to 50 carbon atoms, from 5 to 30 carbon atoms, or from 7 to 20 carbon atoms; and wherein each occurrence of $R^5$ is independently absent or selected from the group consisting of hydrogen, monovalent cationic groups, and organic groups having from 1 to 50 carbon atoms, from 1 to 30 carbon atoms, from 3 to 30 carbon atoms, or from 7 to 20 carbon atoms. $R^3$ can be deoxyribose, fructose, galactose, gentiobiulose, gentiobiose, glucose, kestose, isomaltose, isomaltotriose, kojibiose, laminaribiose, maltose, maltulose, maltotriose, maltotriulose, mannobiose, mannose, melibiose, melibiulose, nigerose, nigerotriose, raffinose, ribose, rutinose, rutinulose, sophorose, trehalose, β,β-trehalose, α,β-trehalose, or turanose, optionally containing one or more substituents. In certain embodiments, the substituents $R^3$ and $R^5$ may together form a ring, for instance as found in cyclic adenosine monophosphate.

$R^4$ can be a nitrogen-containing heterocycle. Nitrogen-containing heterocycles can be saturated or unsaturated. Nitrogen-containing heterocycles can include substituted and unsubstituted pyrrolidine, pyrrole, imidazolidine, pyrazolidine, imidazole, pyrazole, oxazolidine, isoxazolidine, oxazole, isoxazole, piperidine, tetrahydropyridine, dihydropyridine, pyridine, pyrimidine, piperazine, polycyclic and fused ring structures thereof, and derivatives thereof. $R^4$ can be a bulky cyclic group. Suitable bulky cyclic groups can include 5-membered carbocycles and heterocycles such as cyclopentane, cyclopentene, cyclopentadiene, pyrrolidine, pyrrole, imidazolidine, pyrazolidine, imidazole, pyrazole, oxazolidine, isoxazolidine, oxazole, isoxazole, tetrahydrofuran, furan, dioxolane, thiolane, thiophene, dithiolane, thiazole, isothiazole, phosphole, silole, triazole, oxadiazole, and derivatives thereof. Suitable bulky cyclic groups can include 6-membered carbocycles and heterocycles such as cyclohexane, cyclohexene, cyclohexa-1,3-diene, cyclohexa-1,4-diene, benzene, piperidine, tetrahydropyridine, dihydropyridine, pyridine, oxane, pyran, piperazine, pyrazine, pyrimidine, pyridazine, morpholine, 1,3,5-triazine, and derivatives thereof. Suitable bulky cyclic groups can include 7-membered carbocycles and heterocycles such as cycloheptane, cycloheptene, azepane, azepine, thiepine, diazepine, thiazepine, and derivatives thereof. Suitable bulky cyclic groups can include polycyclic compounds such as polycyclic and fused ring structures of any of the above carbocycles and heterocycles such as naphthalene, anthracene, tetracene, acridine, dibenzothiophene, carbazole, dibenzofuran, decalin, bridged carbocycles and heterocycles such as norbornane, adamantane, and spirocyclic compounds such as spiro[2.2]pentane.

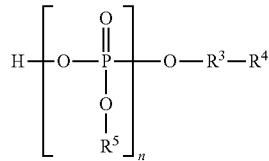

Formula C-III

The viscosity-reducing organophosphate can be a dinucleotide phosphate. The viscosity-reducing organophosphate can have a structure according to Formula C-IV wherein n is an integer from 1 to 20, from 1 to 10, from 2 to 10, or from 2 to 6; wherein each occurrence of $R^6$ is independently absent or selected from a sugar, preferably a monosaccharide or disaccharide, having from 1 to 30 carbon atoms, from 1 to 20 carbon atoms, or from 4 to 20 carbon atoms; wherein each occurrence of $R^7$ is independently a bulky cyclic group that can be substituted or unsubstituted, preferably a substituted or unsubstituted carbocycle or heterocycle having from 3 to 50 carbon atoms, from 5 to 30 carbon atoms, or from 7 to 20 carbon atoms; and wherein each occurrence of $R^8$ is independently absent or selected from the group consisting of hydrogen, monovalent cationic groups, and organic groups having from 1 to 50 carbon atoms, from 1 to 30 carbon atoms, from 3 to 30 carbon atoms, or from 7 to 20 carbon atoms. Each $R^6$ can independently be deoxyribose, fructose, galactose, gentiobiulose, gentiobiose. glucose, kestose, isomaltose, isomaltotriose, kojibiose, laminaribiose, maltose, maltulose, maltotriose, maltotriulose, mannobiose, mannose, melibiose, melibiulose, nigerose, nigerotriose, raffinose, ribose, rutinose, rutinulose, sophorose, trehalose, β,β-trehalose, α,β-trehalose, or turanose, optionally containing one or more substituents. Each $R^7$ can independently be a nitrogen-containing heterocycle. Nitrogen-containing heterocycles can be saturated or unsaturated. Nitrogen-containing heterocycles can include substituted and unsubstituted pyrrolidine, pyrrole, imidazolidine, pyrazolidine, imidazole, pyrazole, oxazolidine, isoxazolidine, oxazole, isoxazole, piperidine, tetrahydropyridine, dihydropyridine, pyridine, pyrimidine, piperazine, polycyclic and fused ring structures thereof, and derivatives thereof. Each $R^7$ can independently be a bulky cyclic group. Suitable bulky cyclic groups can include 5-membered carbocycles and heterocycles such as cyclopentane, cyclopentene, cyclopentadiene, pyrrolidine, pyrrole, imidazolidine, pyrazolidine, imidazole, pyrazole, oxazolidine, isoxazolidine, oxazole, isoxazole, tetrahydrofuran, furan, dioxolane, thiolane, thiophene, dithiolane, thiazole, isothiazole, phosphole, silole, triazole, oxadiazole, and derivatives thereof. Suitable bulky cyclic groups can include 6-membered carbocycles and heterocycles such as cyclohexane, cyclohexene, cyclohexa-1,3-diene, cyclohexa-1,4-diene, benzene, piperidine, tetrahydropyridine, dihydropyridine, pyridine, oxane, pyran, piperazine, pyrazine, pyrimidine, pyridazine, morpholine, 1,3,5-triazine, and derivatives thereof. Suitable bulky cyclic groups can include 7-membered carbocycles and heterocycles such as cycloheptane, cycloheptene, azepane, azepine, thiepine, diazepine, thiazepine, and derivatives thereof. Suitable bulky cyclic groups can include polycyclic compounds such as polycyclic and fused ring structures of any of the above carbocycles and heterocycles such as naphthalene, anthracene, tetracene, acridine, dibenzothiophene, carbazole, dibenzofuran, decalin; bridged carbocycles and heterocycles such as norbornane, adamantane, and spirocyclic compounds such as spiro[2.2]pentane.

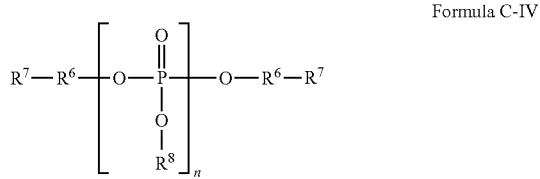

Formula C-IV

The viscosity-reducing organophosphate can be thiamine pyrophosphate (TPP), the structure of which is shown below as a chloride salt, or a derivative thereof. Derivatives of TPP can include replacing the diphosphate with a different phosphate such as monophosphate to triphosphate; replacing the chloride anion with other anionic constituents; replacing one or more methyl substituents with higher-order alkyl or N-alkyl substituents; replacing one or more amino substituents with substituted or unsubstituted alkyl, aminoalkyl, heterocyclyl, aryl, or heteroaryl groups having from 1 to 30 carbon atoms; replacing one or more hydroxyl groups with O-acyl or O-alkyl groups; or a combination thereof. Suitable anionic constituents include halide ions, sulfate, sulfonate, sulfite, sulfinate, phosphate, phosphonate, phosphite, phosphonite, carbonate, and carboxylate anions optionally substituted with one or more alkyl, heteroalkyl, alkenyl, alkynyl, carbocyclic, or heterocyclic groups, preferably having from 1 to 20 or from 1 to 12 carbon atoms. Exemplary anionic constituents include chloride, bromide, methylphosphate, methyl-ethyl-phosphate, methylsulfate, methylsulfonate, formate, acetate, butyrate, citrate, and lactate and bulky hydrophobic anions such as camphor sulfonic acid (CSA), benzenesulfonic acid (BSA), toluenesulfonic acid (TSA), 1-(3-aminopropyl)-2-methyl-1H-imidazole (APMI), or methanesulfonic acid (MSA). Derivatives can include base addition salts of TPP using common inorganic bases such as NaOH or exemplary hydrophobic bases described above.

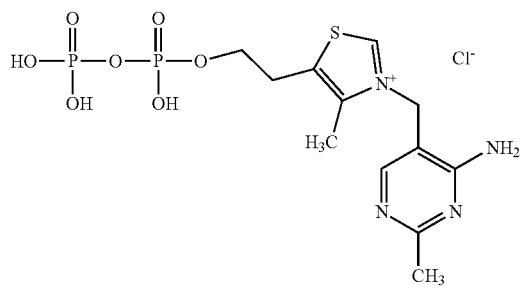 [SMILES: Cc1ncc(C[n+]2csc(CCOP(=O)(O)OP(=O)(O)O)c2C)c(N)n1 ; [Cl-]]

In other embodiments, the viscosity-reducing organophosphate may be benfotiamine or the corresponding diphosphate or triphosphate analog. The viscosity-reducing organophosphate may fursultiamine monophosphate, prosultiamine monophosphate, or allithiamine monophosphate, as well as the corresponding diphosphate or triphosphate of any of the above.

The viscosity-reducing organophosphate can be adenosine triphosphate (ATP), the structure of which is shown below as a sodium salt, or a derivative thereof. Derivatives of ATP can include replacing the triphosphate with a different phosphate such as monophosphate or diphosphate; replacing the amino substituent with substituted or unsubstituted alkyl, aminoalkyl, aryl, heterocyclyl or heteroaryl groups having from 1 to 30 carbon atoms; replacing one or more hydroxyl groups with O-acyl or O-alkyl groups; or a combination thereof.

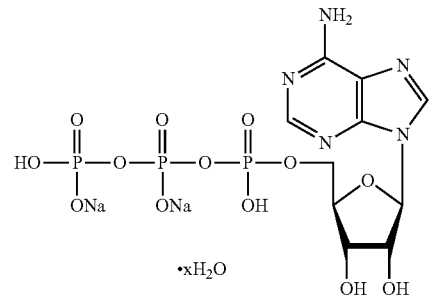

The viscosity-reducing organophosphate can be deoxyadenosine triphosphate (dATP), the structure of which is shown below, or a derivative thereof. Derivatives of dATP can include replacing the triphosphate with a different phosphate such as monophosphate or diphosphate; replacing the amino substituent with substituted or unsubstituted alkyl, aminoalkyl, aryl, heterocyclyl, or heteroaryl groups having from 1 to 30 carbon atoms; replacing one or more hydroxyl groups with O-acyl or O-alkyl groups; or a combination thereof.

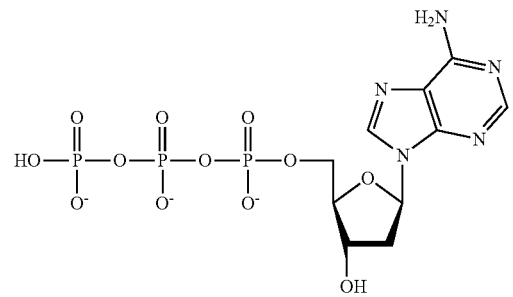 [SMILES: Nc1ncnc2c1ncn2[C@H]1C[C@@H](O)[C@@H](COP(=O)([O-])OP(=O)([O-])OP(=O)([O-])O)O1]

The viscosity-reducing organophosphate can be deoxyguanosine triphosphate (dGTP), the structure of which is shown below, or a derivative thereof. Derivatives of dGTP can include replacing the triphosphate with a different phosphate such as monophosphate or diphosphate; replacing the amino substituent with substituted or unsubstituted alkyl, aminoalkyl, heterocyclyl, aryl, or heteroaryl groups having from 1 to 30 carbon atoms; replacing one or more hydroxyl groups with O-acyl or O-alkyl groups; or a combination thereof.

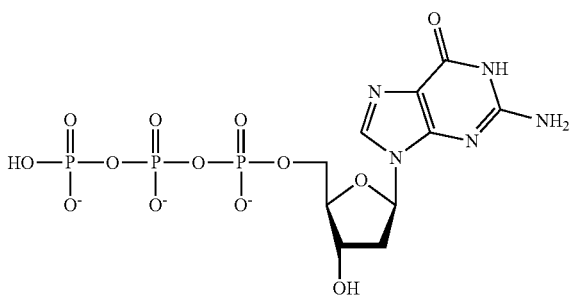 [SMILES: Nc1nc2c(ncn2[C@H]2C[C@@H](O)[C@@H](COP(=O)([O-])OP(=O)([O-])OP(=O)([O-])O)O2)c(=O)[nH]1]

The viscosity-reducing organophosphate can be deoxythymidine triphosphate (dTTP), the structure of which is shown below, or a derivative thereof. Derivatives of dTTP can include replacing the triphosphate with a different phosphate such as monophosphate or diphosphate; replacing the methyl substituent with higher-order alkyl or N-alkyl substituents; replacing one or more amino substituents with substituted or unsubstituted alkyl, aminoalkyl, heterocyclyl, aryl, or heteroaryl groups having from 1 to 30 carbon atoms; replacing one or more hydroxyl groups with O-acyl or O-alkyl groups; or a combination thereof.

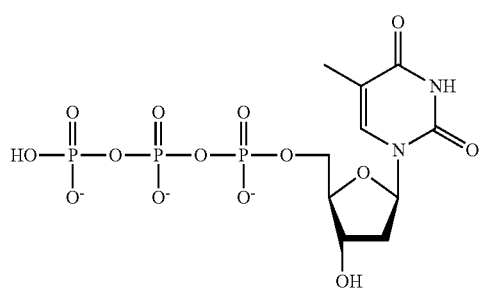 [SMILES: Cc1cn([C@H]2C[C@@H](O)[C@@H](COP(=O)([O-])OP(=O)([O-])OP(=O)([O-])O)O2)c(=O)[nH]c1=O]

The viscosity-reducing organophosphate can be deoxycytidine triphosphate (dCTP), the structure of which is shown below, or a derivative thereof. Derivatives of dCTP can include replacing the triphosphate with a different phosphate such as monophosphate or diphosphate; replacing the amino substituent with substituted or unsubstituted alkyl, aminoalkyl, aryl, heterocyclyl, or heteroaryl groups having from 1 to 30 carbon atoms; replacing one or more hydroxyl groups with O-acyl or O-alkyl groups; or a combination thereof.

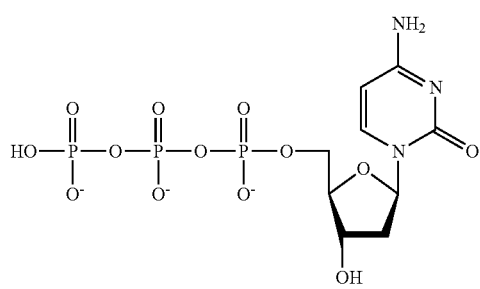 [SMILES: Nc1ccn([C@H]2C[C@@H](O)[C@@H](COP(=O)([O-])OP(=O)([O-])OP(=O)([O-])O)O2)c(=O)n1]

The viscosity-reducing organophosphate can be cyclic adenosine monophosphate (cAMP), the structure of which is shown below, or a derivative thereof. Derivatives of cAMP can include replacing the monophosphate with a different phosphate such as diphosphate or triphosphate; replacing the amino substituent with substituted or unsubstituted alkyl, aminoalkyl, aryl, heterocyclyl, or heteroaryl groups having from 1 to 30 carbon atoms; replacing the hydroxyl group with O-acyl or O-alkyl groups; or a combination thereof.

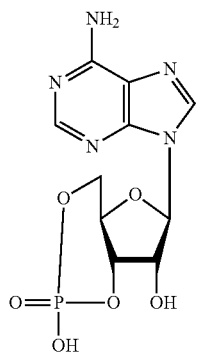

The viscosity-reducing organophosphate can be cyclic guanosine monophosphate (cGMP), the structure of which is shown below, or a derivative thereof. Derivatives of cGMP can include replacing the monophosphonate with a different phosphate such as diphosphate or triphosphate; replacing the amino substituent with substituted or unsubstituted alkyl, aminoalkyl, aryl, heterocyclyl, or heteroaryl groups having from 1 to 30 carbon atoms; replacing one or more hydroxyl groups with O-acyl or O-alkyl groups; or a combination thereof.

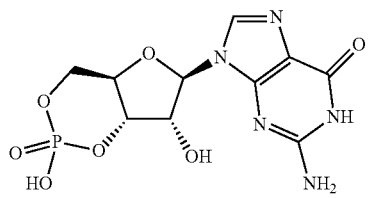

The viscosity-reducing organophosphate can be cyclic thymidine monophosphate (cTMP), the structure of which is shown below, or a derivative thereof. Derivatives of cTMP can include replacing the monophosphonate with a different phosphate such as diphosphate or triphosphate; replacing the methyl substituent with higher-order alkyl or N-alkyl substituents; replacing one or more amino substituents with substituted or unsubstituted alkyl, aminoalkyl, aryl, heterocyclyl, or heteroaryl groups having from 1 to 30 carbon atoms; replacing one or more hydroxyl groups with O-acyl or O-alkyl groups; or a combination thereof.

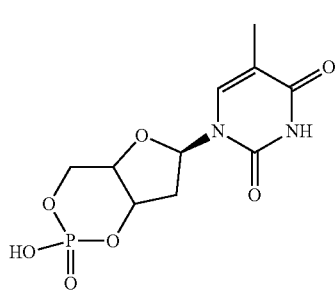 [SMILES: Cc1cn([C@H]2CC3OP(=O)(O)OCC3O2)c(=O)[nH]c1=O]

The viscosity-reducing organophosphate can be cyclic cytidine monophosphate (cCMP), the structure of which is shown below, or a derivative thereof. Derivatives of cCMP can include replacing the monophosphonate with a different phosphate such as diphosphate or triphosphate; replacing the amino substituent with substituted or unsubstituted alkyl, aminoalkyl, aryl, heterocyclyl, or heteroaryl groups having from 1 to 30 carbon atoms; replacing one or more hydroxyl groups with O-acyl or O-alkyl groups; or a combination thereof.

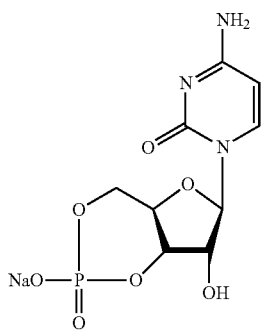

The viscosity-reducing organophosphate can be nicotinamide adenine dinucleotide phosphate (NADP), the structure of which is shown below as a sodium salt, or a derivative thereof. Derivatives of NADP can include replacing the diphosphate with a different phosphate such as monophosphate or triphosphate; replacing the diphosphonate with a different phosphate; replacing one or more amino substituents with substituted or unsubstituted alkyl, aminoalkyl, heterocyclyl, aryl, or heteroaryl groups having from 1 to 30 carbon atoms; replacing one or more hydroxyl groups with O-acyl or O-alkyl groups; or a combination thereof.

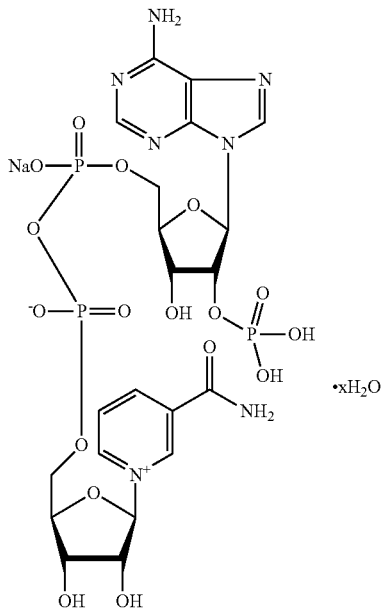

The viscosity-reducing organophosphate can be pyridoxal phosphate, the structure of which is shown below, or a derivative thereof. Derivatives of pyridoxal phosphate can include replacing the monophosphate with a different phosphate such as diphosphate or triphosphate; replacing the methyl substituent with higher-order alkyl or N-alkyl substituents; replacing one or more hydroxyl groups with O-acyl or O-alkyl groups; or a combination thereof.

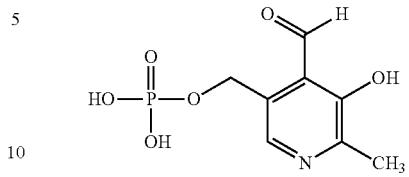

The viscosity-reducing organophosphate can be riboflavin-5h as diphosphate or triphosphate; replacing the methyl substitutive thereof. Derivatives of riboflavin-5'-phosphate can include replacing the phosphate with a different phosphate such as a diphosphate or triphosphate; replacing the sodium counter ion with other cationic constituents; replacing one or more methyl substituents with higher-order alkyl or N-alkyl substituents; replacing one or more hydroxyl groups with O-acyl or O-alkyl groups; or combinations thereof.

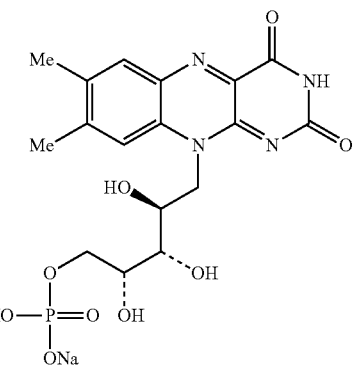

4. Pharmaceutically Acceptable Water-Soluble Organic Dyes

In one aspect, the viscosity-lowering agent is a water-soluble organic dye. The viscosity of liquid polysaccharide and nucleic acid formulations, including low-molecular-weight and/or high-molecular-weight polysaccharides and nucleic acids, is reduced by the addition of one or more water-soluble organic dyes. The pharmaceutical formulations may be converted from non-Newtonian to Newtonian fluids by the addition of an effective amount of one or more water-soluble organic dyes. A "water-soluble organic dye" is an organic molecule having a molar solubility in water of at least 0.001 M at 25° C. and pH 7, and that absorbs certain wavelengths of light, preferably in the visible to infrared portion of the electromagnetic spectrum, while possibly transmitting or reflecting other wavelengths of light. The water-soluble organic dye may be an acridine dye, anthraquinone dye, diaryl methane dye, triaryl methane dye, azo dye, diazonium dye, nitrophenyl dye, nitroso phenyl dye, phthalocyanine dye, quinone dye, thiazole dye, xanthene dye, or a combination thereof. The organic dye can be a salt or a zwitterion.

Although generally any water-soluble organic dye may lower the viscosity of a polysaccharide or nucleic acid formulation, in some embodiments the organic dyes have a molar extinction coefficient in the visible to infrared portion of the electromagnetic spectrum that is greater than 500 $M^{-1}$ cm$^{-1}$, greater than 1,000 M$^{-1}$ cm$^{-1}$, greater than 10,000 M$^{-1}$ cm$^{-1}$, greater than 20,000 M$^{-1}$ cm$^{-1}$, or greater than 50,000 M$^{-1}$ cm$^{-1}$.

The organic dye can have a fused-ring structure according to Formula D-I, wherein X is a carbon atom or a heteroatom, optionally having one or more substituents; and each A is independently a substituted or unsubstituted aryl group having from 3 to 50 carbon atoms, from 3 to 30 carbon atoms, or from or from 6 to 25 carbon atoms. It is understood that X may have one or more hydrogen atoms or other substituents that satisfy the valence, for example when X is carbon X may be a CH group, a CH$_2$ group, a CHR group, a CR group, or a CR$_2$ group where each R is independently any organic grouping having any number of carbon atoms.

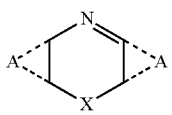

Formula D-I

In some embodiments the organic dye has a structure according to Formula D-I wherein X is C, N, O, or S; or wherein A is a substituted or unsubstituted phenyl or naphthyl group, or both. An example of such a compound is acridine, where X is a CH group and each A is an unsubstituted phenyl group.

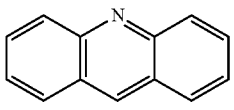

Acridine

The organic dye can be an acridine dye. The organic dye can have a structure according to Formula D-II:

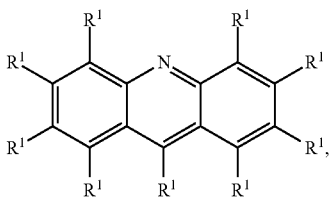

Formula D-II wherein each R$^1$ is independently selected from hydrogen, R$^2$, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, and —N(R$^{4a}$)$_2$;

wherein R$^2$ is independently selected from C$_{1-12}$alkyl, C$_{3-12}$cycloalkyl, C$_{6-12}$aryl, C$_{1-12}$heteroaryl, and C$_{2-12}$heterocyclyl, wherein each C$_{1-12}$alkyl may be substituted one or more times with C$_{3-12}$cycloalkyl, C$_{6-12}$aryl, C$_{1-12}$heteroaryl, C$_{2-12}$heterocyclyl, —OH, NH$_2$, (=O), (=NR$^{4a}$), —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —OR$^4$, —SR$^4$a, or —N(R$^{4a}$)$_2$;

wherein each C$_{3-12}$cycloalkyl may be substituted one or more times with C$_{1-12}$alkyl, C$_{6-12}$aryl, C$_{1-12}$heteroaryl, C$_{2-12}$heterocyclyl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each C$_{6-12}$aryl may be substituted one or more times with C$_{1-12}$alkyl, C$_{3-12}$cycloalkyl, C$_{1-12}$heteroaryl, C$_{2-12}$heterocyclyl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each C$_{1-12}$heteroaryl may be substituted one or more times with C$_{1-12}$alkyl, C$_{3-12}$cycloalkyl, C$_{6-12}$aryl, C$_{2-12}$heterocyclyl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

wherein each C$_{2-12}$heterocyclyl may be substituted one or more times with C$_{1-12}$alkyl, C$_{3-12}$cycloalkyl, C$_{6-12}$aryl, C$_{1-12}$heteroaryl, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$) NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^4$a, or —N(R$^{4a}$)$_2$;

each R$^4$ is independently selected from C$_{1-12}$alkyl, C$_{3-12}$cycloalkyl, C$_{6-12}$aryl, C$_{1-12}$heteroaryl and C$_{2-12}$heterocyclyl, each of which may be substituted one or more times by —OH, —NH$_2$, —F, —Cl, —Br, —I, —NO$_2$, —CN, —C(=O)OH, —SO$_3$H, —PO$_3$H$_2$, or —C(=O)NH$_2$;

each R$^{4a}$ independently may be R$^4$ or hydrogen;

wherein any two or more of R$^2$, R$^3$, R$^4$, and R$^{4a}$ groups may together form a ring In some embodiments at least one, at least two, or at least three occurrences of R$^1$ are not hydrogen. In some embodiments at least one, at least two, at least three, or at least four occurrences of R$^1$ are amine groups such as dimethylamine or other dialkylamines. Other preferred R$^1$ groups include NO$_2$, SO$_3$H, and CO$_2$H The water-soluble organic dye may also be an anthraquinone dye,

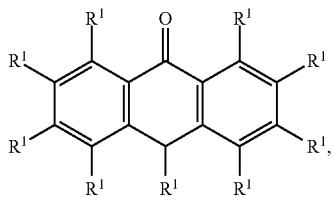

a diaryl methane dye,

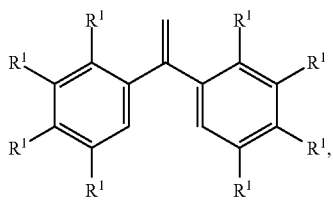

or
a triaryl methane dye,

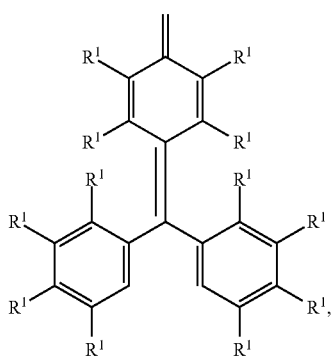

wherein each $R^1$ has a meaning given above. In other embodiments, the water-soluble organic dye may be an azo dye represented by the formula:

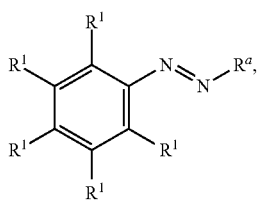

wherein each $R^1$ is as defined above, and $R^a$ is an aryl or heteroaryl ring. Exemplary ring systems include:

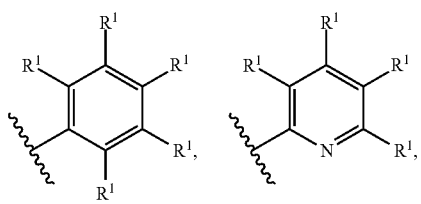

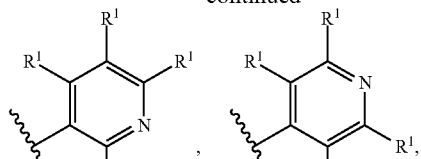

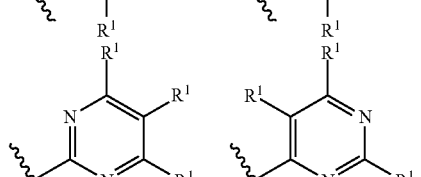

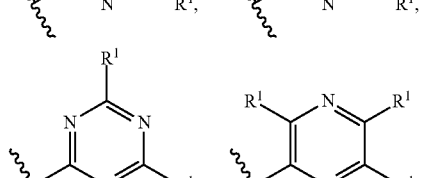

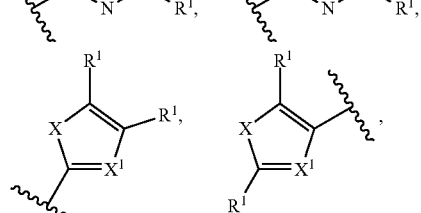

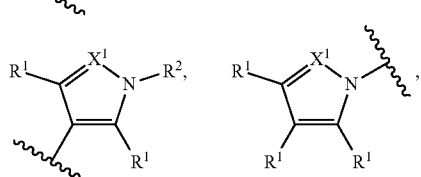

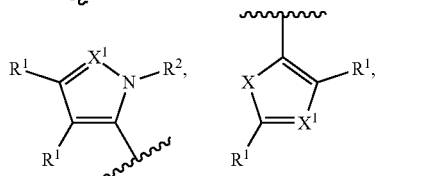

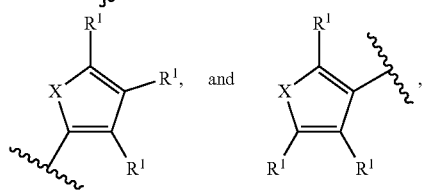

wherein X is O, S, $SO_2$ or $NR^2$, $X^1$ may be a nitrogen atom or $CR^1$ and $R^1$ and $R^2$ are each as defined above.

The water-soluble organic dye may also be a nitrophenyl dye, nitroso phenyl dye, phthalocyanine dye, quinone dye, thiazole dye or xanthene dye.

Exemplary dyes include, but are not limited to, Yellow 5, Orange G, Quinolone Yellow, Betanin, Red 40, carmosin, Azure C, Congo Red, amaranth, Ponceau S, erythrosine, patent blue, brilliant black BN, acid fuchsine, napthol yellow S, quinoline yellow, indigo carmine, fast green FCF, Orange 2, Natural Red, Xylene Cyanol FF, Cresyl violet acetate, Light Green SF Yellowish, Thiaozle Yellow G, crystal violet, Nile blue A, and Cardiogreen.

In the polysaccharide and nucleic acid formulations of the present invention, one or more viscosity-lowering agents described herein (e.g., viscosity-lowering compounds of formulae A-I, A-II, A-III and variations thereof, ionic liquids, organophosphates, water-soluble organic dyes, and other viscosity-lowering compounds described herein) can be combined with each other, or combined with other types of viscosity-lowering agents known in the art. For example, a viscosity-lowering compound of formula A-I, A-II, A-III, or a variation thereof described herein, can be combined with a viscosity-lowering ionic liquid, and/or a viscosity-lowering organophosphate, and/or viscosity-lowering water-soluble organic dye, and/or another viscosity-lowering compound described herein (e.g., organosulfonic acids, carboxylic acids, organic bases, and the like).

Other viscosity-lowering agents may also be used in the polysaccharide and nucleic acid formulations of the present invention, for example, the typically bulky polarized organic compounds, such as hydrophobic compounds, many of the GRAS (US Food and Drug Administration List of compounds Generally Regarded As Safe) and inactive injectable ingredients and FDA approved therapeutics, the water soluble organic dyes described in PCT Application PCT/US14/55203, entitled "LIQUID PROTEIN FORMULATIONS CONTAINING WATER-SOLUBLE ORGANIC DYES" by Arsia Therapeutics; and the organophosphate viscosity-lowering agents described in PCT Application PCT/US14/55210, entitled "LIQUID PROTEIN FORMULATIONS CONTAINING ORGANOPHOSPHATES" by Arsia Therapeutics; the ionic liquid viscosity-lowering agents described in PCT Application PCT/US14/055245, entitled "LIQUID PROTEIN FORMULATIONS CONTAINING IONIC LIQUIDS" by Arsia Therapeutics; and the viscosity-lowering agents described in PCT Application PCT/US14/55254, entitled "LIQUID PROTEIN FORMULATIONS CONTAINING VISCOSITY-LOWERING AGENTS" by Arsia Therapeutics.

C. Excipients

A wide variety of pharmaceutical excipients useful for liquid polysaccharide and nucleic acid formulations are known to those skilled in the art. They include one or more additives, such as liquid solvents or co-solvents; sugars or sugar alcohols such as mannitol, trehalose, sucrose, sorbitol, fructose, maltose, lactose, or dextrans; surfactants such as TWEEN® 20, 60, or 80 (polysorbate 20, 60, or 80); buffering agents; preservatives such as benzalkonium chloride, benzethonium chloride, tertiary ammonium salts, and chlorhexidinediacetate; carriers such as poly(ethylene glycol) (PEG); antioxidants such as ascorbic acid, sodium metabisulfite, and methionine; chelating agents such as EDTA or citric acid; or biodegradable polymers such as water-soluble polyesters; cryoprotectants; lyoprotectants; bulking agents; and stabilizing agents.

Other pharmaceutically acceptable carriers, excipients, or stabilizers, such as those described in Remington: "The Science and Practice of Pharmacy", 20th edition, Alfonso R. Gennaro, Ed., Lippincott Williams & Wilkins (2000) may also be included in the formulations described herein, provided that they do not adversely affect the desired characteristics of the formulation.

III. Methods of Making

Fermentation methods for the production of polysaccharides and nucleic acids are known to those of skill in the art, and are described, for instance in *Fermentation and Biochemical Engineering Handbook*, $3^{rd}$ ed. H. C. Vogel and C. M. Todaro, eds. Elsevier, Waltham, 2014. Inclusion of viscosity-lowering agents (e.g., viscosity-lowering compounds of formulae A-I, A-II, A-III and variations thereof, ionic liquids, organophosphates, water-soluble organic dyes, and other viscosity-lowering compounds described herein) at viscosity-reducing concentrations such as 0.010 M to 1.0 M, preferably 0.050 M to 0.50 M, most preferably 0.01 M to 0.10 M, allows a solution of the pharmaceutically active polysaccharide or nucleic acid to be prepared, purified and/or concentrated at higher concentrations than otherwise permitted without the viscosity-lowering agents, using common methods known to those skilled in the art, including but not limited to chromatography (i.e. size exclusion), ion exchange, tangential flow filtration, centrifugal concentration, and dialysis. The viscosity-lowering agent may be added at the beginning of the fermentation process, over the course of the fermentation process, or upon the conclusion of the fermentation process.

Heparin and other heparin like-compounds (fractionated heparins, unfractionated heparins, de-sulfated heparins and the like) are generally obtained by extraction from animal tissue. After proteolysis the crude hydrolysate is filtered and semi-purified using an anion exchange resin, which selectively binds the highly anionic heparin molecules. The heparin is then released from the resin by treatment with acid and further purified using combinations of precipitation, filtration and chromatography. Many LMWH compounds are prepared by chemical modification of the purified heparin. A viscosity-lowering agent can be added to the heparin at any stage of the above sequence to facilitate processing and allow for more highly concentrated solutions.

In some embodiments, lyophilized formulations of polysaccharides and nucleic acids are provided and/or are used in the preparation and manufacture of the low-viscosity, concentrated formulations. In some embodiments, the pre-lyophilized polysaccharide or nucleic acid in a powder form is reconstituted by dissolution in an aqueous solution. In this embodiment, the liquid formulation is filled into a specific dosage unit container such as a vial or pre-filled mixing syringe, lyophilized, optionally with lyoprotectants, preservatives, antioxidants, and other typical pharmaceutically acceptable excipients, then stored under sterile storage conditions until shortly before use, at which time it is reconstituted with a defined volume of diluent, to bring the liquid to the desired concentration and viscosity.

The formulations described herein may be stored by any suitable method known to one skilled in the art. Non-limiting examples of methods for preparing the polysaccharide and nucleic acid formulations for storage include freezing, lyophilizing, and spray drying the liquid formulation. In some cases, the lyophilized formulation is frozen for storage at subzero temperatures, such as at about −80° C. or in liquid nitrogen. In some cases, a lyophilized or aqueous formulation is stored at 2-8° C.

Non-limiting examples of diluents useful for reconstituting a lyophilized formulation prior to injection include sterile water, bacteriostatic water for injection (BWFI), a pH buffered solution (e.g., phosphate-buffered saline), sterile saline solution, Ringer's solution, dextrose solution, or aqueous solutions of salts and/or buffers. In some cases, the formulation is spray-dried and then stored.

IV. Administration to an Individual in Need Thereof

The polysaccharide and nucleic acid formulations, including, but not limited to, reconstituted formulations, are administered to a person in need thereof by intramuscular, intraperitoneal (i.e., into a body cavity), intracerebrospinal, or subcutaneous injection using an 18-32 gauge needle (optionally a thin-walled needle), in a volume of less than about 5 mL, less that about 3 mL, preferably less than about 2 mL, more preferably less than about 1 mL.

The appropriate dosage ("therapeutically effective amount") of the polysaccharide or nucleic acid will depend on the condition to be treated, the severity and course of the disease or condition, whether the agent is administered for preventive or therapeutic purposes, previous therapy, the patient's clinical history and response to the polysaccharide or nucleic acid, the type of polysaccharide or nucleic acid used, and the discretion of the attending physician. The polysaccharide or nucleic acid is suitably administered at one time in single or multiple injections, or over a series of treatments, as the sole treatment, or in conjunction with other drugs or therapies.

Dosage formulations are designed so that the injections cause no significant signs of irritation at the site of injection, for example, wherein the primary irritation index is less than 3 when evaluated using a Draize scoring system. In an alternative embodiment, the injections cause macroscopically similar levels of irritation when compared to injections of equivalent volumes of saline solution. In another embodiment, the bioavailability of the polysaccharide or nucleic acid is higher when compared to the otherwise same formulation without the viscosity-lowering agent(s) administered in the same way. In another embodiment, the formulation is at least approximately as effective pharmaceutically as about the same dose of the polysaccharide or nucleic acid administered by intravenous infusion.

In a preferred embodiment, the formulation is injected to yield increased levels of the therapeutic polysaccharide or nucleic acid. For example, the AUC value may be at least 10%, preferably at least 20%, larger than the same value computed for the otherwise same formulation without the viscosity-lowering agent(s) administered in the same way.

The viscosity-lowering agent(s) may also affect bioavailability. For example, the percent bioavailability of the polysaccharide or nucleic acid may be at least 1.1 times, preferably at least 1.2 times the percent bioavailability of the otherwise same formulation without the viscosity-lowering agent(s) administered in the same way.

The viscosity-lowering agent(s) may also affect the pharmacokinetics. For example, the $C_{MAX}$ after SC or IM injection may be at least 10%, preferably at least 20%, less than the $C_{MAX}$ of an approximately equivalent pharmaceutically effective intravenously administered dose.

In some embodiments, the polysaccharides and nucleic acids are administered at a higher dosage and a lower frequency than the otherwise same formulations without the viscosity-lowering agent(s).

The lower viscosity formulations require less injection force. For example, the injection force may be at least 10%, preferably at least 20%, less than the injection force for the otherwise same formulation without the viscosity-lowering agent(s) administered in the same way. In one embodiment, the injection is administered with a 27 gauge needle and the injection force is less than 30 N. The formulations can be administered in most cases using a very small gauge needle, for example, between 27 and 31 gauge, typically 27, 29 or 31 gauge.

The viscosity-lowering agent(s) may be used to prepare a dosage unit formulation suitable for reconstitution to make a liquid pharmaceutical formulation for subcutaneous or intramuscular injection. The dosage unit may contain a dry powder of one or more polysaccharides or nucleic acids; one or more viscosity-lowering agents; and other excipients. The polysaccharides and nucleic acids are present in the dosage unit such that after reconstitution in a pharmaceutically acceptable solvent, the resulting formulation has a polysaccharide or nucleic acid concentration from about 100 mg to about 2,000 mg per 1 mL (mg/mL). Such reconstituted formulations may have an absolute viscosity of from about 1 cP to about 50 cP at 25° C.

The low viscosity formulation can be provided as a solution or in a dosage unit form where the polysaccharide or nucleic acid is lyophilized in one vial, with or without the viscosity-lowering agent(s) and the other excipients, and the solvent, with or without the viscosity-lowering agent(s) and other excipients, is provided in a second vial. In this embodiment, the solvent is added to the polysaccharide or nucleic acids shortly before or at the time of injection to ensure uniform mixing and dissolution.

The viscosity-lowering agent(s) are present in the formulations at concentrations that cause no significant signs of toxicity and/or no irreversible signs of toxicity when administered via subcutaneous, intramuscular, or other types of injection. As used herein, "significant signs of toxicity" include intoxication, lethargy, behavioral modifications such as those that occur with damage to the central nervous system, infertility, signs of serious cardiotoxicity such as cardiac arrhythmia, cardiomyopathy, myocardial infarctions, and cardiac or congestive heart failure, kidney failure, liver failure, difficulty breathing, and death.

In preferred embodiments the formulations cause no significant irritation when administered not more than twice daily, once daily, twice weekly, once weekly, or once monthly. The formulations can be administered causing no significant signs of irritation at the site of injection, as measured by a primary irritation index of less than 3, less than 2, or less than 1 when evaluated using a Draize scoring system. As used herein, "significant signs of irritation" include erythema, redness, and/or swelling at the site of injection having a diameter of greater than 10 cm, greater than 5 cm, or greater than 2.5 cm, necrosis at the site of injection, exfoliative dermatitis at the site of injection, and severe pain that prevents daily activity and/or requires medical attention or hospitalization. In some embodiments, injections of the polysaccharide and nucleic acid formulations cause macroscopically similar levels of irritation when compared to injections of equivalent volumes of saline solution.

The polysaccharide and nucleic acid formulations can exhibit increased bioavailability compared to the otherwise same formulation without the viscosity-lowering agent(s) when administered via subcutaneous or intramuscular injection. "Bioavailability" refers to the extent and rate at which the bioactive species reaches circulation or the site of action. The overall bioavailability can be increased for SC or IM injections as compared to the otherwise same formulations without the viscosity-lowering agent(s). "Percent bioavailability" refers to the fraction of the administered dose of the bioactive species which enters circulation, as determined with respect to an intravenously administered dose. One way of measuring the bioavailability is by comparing the "area under the curve" (AUC) in a plot of the plasma concentration as a function of time. The AUC can be calculated, for example, using the linear trapezoidal rule. "$AUC_\infty$", as used herein, refers to the area under the plasma concentration curve from time zero to a time where the plasma concentration returns to baseline levels. "$AUC_{0-t}$", as used herein, refers to the area under the plasma concentration curve from time zero to a time, t, later, for example to the time of reaching baseline. The time will typically be measured in days, although hours can also be used as will be apparent by context. For example, the AUC can be increased by more than 10%, 20%, 30%, 40%, or 50% as compared to the otherwise same formulation without the viscosity-lowering agent(s) and administered in the same way.

As used herein, "$t_{max}$" refers to the time after administration at which the plasma concentration reaches a maximum.

As used herein, "$C_{max}$" refers to the maximum plasma concentration after dose administration, and before administration of a subsequent dose.

As used herein, "$C_{min}$" or "$C_{trough}$" refers to the minimum plasma concentration after dose administration, and before administration of a subsequent dose.

The $C_{max}$ after SC or IM injection may be less, for example, at least 10%, more preferably at least 20%, less than the $C_{max}$ of an intravenously administered dose. This reduction in $C_{max}$ may also result in decreased toxicity.

The pharmacokinetic and pharmacodynamic parameters may be approximated across species using approaches that are known to the skilled artisan. The pharmacokinetics and pharmacodynamics of polysaccharide and nucleic acid therapeutics can differ markedly based upon the formulation.

The low-viscosity polysaccharide and nucleic acid formulations can allow for greater flexibility in dosing and decreased dosing frequencies compared to those formulations without the viscosity-lowering agent(s). For example, by increasing the dosage administered per injection multiple-fold, the dosing frequency can in some embodiments be decreased from once every 2 weeks to once every 6 weeks.

The polysaccharide and nucleic acid formulations, including, but not limited to, reconstituted formulations, can be administered using a heated and/or self-mixing syringe or autoinjector. The polysaccharide and nucleic acid formulations can also be pre-heated in a separate warming unit prior to filling the syringe.

i. Heated Syringes

The heated syringe can be a standard syringe that is pre-heated using a syringe warmer. The syringe warmer will generally have one or more openings each capable of receiving a syringe containing the polysaccharide or nucleic acid formulation and a means for heating and maintaining the syringe at a specific (typically above the ambient) temperature prior to use. This will be referred to herein as a pre-heated syringe. Suitable heated syringe warmers include those available from Vista Dental Products and Inter-Med. The warmers are capable of accommodating various sized syringes and heating, typically to within 1° C., to any temperature up to about 130° C. In some embodiments the syringe is pre-heated in a heating bath such as a water bather maintained at the desired temperature.

The heated syringe can be a self-heating syringe, i.e., capable of heating and maintaining the liquid formulation inside the syringe at a specific temperature. The self-heating syringe can also be a standard medical syringe having attached thereto a heating device. Suitable heating devices capable of being attached to a syringe include syringe heaters or syringe heater tape available from Watlow Electric Manufacturing Co. of St. Louis, Mo., and syringe heater blocks, stage heaters, and in-line perfusion heaters available from Warner Instruments of Hamden, Conn., such as the SW-61 model syringe warmer. The heater may be controlled through a central controller, e.g. the TC-324B or TC-344B model heater controllers available from Warner Instruments.

The heated syringe maintains the liquid formulation at a specified temperature or to within 1° C., within 2° C., or within 5° C. of a specified temperature. The heated syringe can maintain the formulation at any temperature from room temperature up to about 80° C., up to about 60° C., up to about 50° C., or up to about 45° C. as long as the polysaccharide or nucleic acid formulation is sufficiently stable at that temperature. The heated syringe can maintain the formulation at a temperature between 20° C. and 60° C., between 21° C. and 45° C., between 22° C. and 40° C., between 25° C. and 40° C., or between 25° C. and 37° C. By maintaining the polysaccharide and nucleic acid formulations at an elevated temperature during injection, the viscosity of the liquid formulation is decreased, the solubility of the polysaccharide and nucleic acid in the formulation is increased, or both.

ii. Self-Mixing Syringes

The syringe can be self-mixing or can have a mixer attached. The mixer can be a static mixer or a dynamic mixer. Examples of static mixers include those disclosed in U.S. Pat. Nos. 5,819,988, 6,065,645, 6,394,314, 6,564,972, and 6,698,622. Examples of some dynamic mixers can include those disclosed in U.S. Pat. Nos. 6,443,612 and 6,457,609, as well as U.S. Patent Application Publication No. US 2002/0190082. The syringe can include multiple barrels for mixing the components of the liquid polysaccharide or nucleic acid formulation. U.S. Pat. No. 5,819,998 describes syringes with two barrels and a mixing tip for mixing two-component viscous substances.

iii. Autoinjectors and Pre filled Syringes of Polysaccharide and Nucleic Acid Formulations The liquid polysaccharide and nucleic acid formulation can be administered using a pre-filled syringe autoinjector or a needleless injection device. Autoinjectors include a handheld, often pen-like, cartridge holder for holding replaceable pre-filled cartridges and a spring based or analogous mechanism for subcutaneous or intramuscular injections of liquid drug dosages from a pre-filled cartridge. Autoinjectors are typically designed for self-administration or administration by untrained personnel. Autoinjectors are available to dispense either single dosages or multiple dosages from a pre-filled cartridge. Autoinjectors enable different user settings including, inter alia, injection depth, injection speed, and the like. Other injection systems can include those described in U.S. Pat. No. 8,500,681.

The lyophilized polysaccharide and nucleic acid formulations can be provided in pre-filled or unit-dose syringes. U.S. Pat. Nos. 3,682,174; 4,171,698; and 5,569,193 describe sterile syringes containing two-chambers that can be pre-filled with a dry formulation and a liquid that can be mixed immediately prior to injection. U.S. Pat. No. 5,779,668 describes a syringe system for lyophilization, reconstitution, and administration of a pharmaceutical composition. In some embodiments the polysaccharide or nucleic acid formulation is provided in lyophilized form in a pre-filled or unit-dose syringe, reconstituted in the syringe prior to administration, and administered as a single subcutaneous or intramuscular injection. Autoinjectors for delivery of unit-dose lyophilized drugs are described in WO 2012/010,832. Auto injectors such as the Safe Click Lyo™ (marketed by Future Injection Technologies, Ltd., Oxford, U.K.) can be used to administer a unit-dose formulation where the formulation is stored in lyophilized form and reconstituted just prior to administration. In some embodiments the polysaccharide or nucleic acid formulation is provided in unit-dose cartridges for lyophilized drugs (sometimes referred to as Vetter cartridges). Examples of suitable cartridges can include those described in U.S. Pat. Nos. 5,334,162 and 5,454,786.

V. Methods of Purification and Concentration

The viscosity-lowering agents can also be used to assist in polysaccharide and nucleic acid purification and concentration. The viscosity-lowering agent(s) and excipients are added to the polysaccharide or nucleic acid in an effective amount to reduce the viscosity of the polysaccharide or nucleic acid solution. For example, the viscosity-lowering agent is added to a concentration of between about 0.01 M and about 1.0 M, preferably between about 0.01 M and about 0.50 M, more preferably between about 0.01 M and about 0.25 M, and most preferably between about 0.01 M and about 0.10 M.

The viscosity-lowering agent solution containing a polysaccharide or nucleic acid is then purified or concentrated using a method selected from the group consisting of ultrafiltration/diafiltration, tangential flow filtration, centrifugal concentration, and dialysis.

EXAMPLES

The foregoing will be further understood by the following non-limiting examples.

All viscosities of well-mixed aqueous macromolecule solutions were measured using either a mVROC microfluidic viscometer (RheoSense) or a DV2T cone and plate viscometer (Brookfield; "C & P") after a 5 minute equilibration at 25° C. (unless otherwise indicated). The mVROC viscometer was equipped with an "A" or "B" chip, each manufactured with a 50 μm channel. Typically, 0.10 mL to 0.50 mL of polysaccharide (or nucleic acid) solution was back-loaded into a gastight microlab instrument syringe (Hamilton; 100 μL or 500 μL, as appropriate), affixed to the chip, and measured at multiple flow rates. Specifically, samples were measured starting at a shear rate that gave at least 20% maximum chip pressure, and continuing until the % maximum reached approximately 100%. For example, a sample of approximately 70 cP would be measured at around 10, 20, 30, 40, 50, 60, 70, 80, 90, 100, 110, and 120 μL/min (approximately 180.2, 360.5, 540.7, 721.0, 901.2, 1081.4, 1261.7, 1441.9, 1622.2, 1802.4, 1982.6, 2162.9 $s^{-1}$, respectively, on a typical "B" chip) until viscosity stabilized, typically after at least 30 seconds. An extrapolated zero-shear viscosity was then determined from a plot of dynamic viscosity versus flow rate for the samples measured on the mVROC microfluidic viscometer for non-Newtonian shear thinning, solutions. For Newtonian solutions, the viscosity is an average of at least three measurements at three different flow rates. The C & P viscometer was equipped with a CPE40 or CPE52 spindle (cone angle of 0.8° and 3.0°, respectively) and 0.50 mL samples were measured at multiple shear rates between 2 and 400 $s^{-1}$. Specifically, samples were measured for 30 seconds each at 22.58, 24.38, 26.25, 28.13, 30, 31.88, 45, 67.5, 90, 112.5, 135, 157.5, 180, 202.5, 247, 270, 292.5, 315, 337.5, 360, 382, 400 $s^{-1}$, starting at a shear rate that gave at least 10% torque, and continuing until instrument torque reached 100%. An extrapolated zero-shear viscosity was then determined from a plot of dynamic viscosity versus shear rate for the samples measured on a DV2T cone and plate viscometer. The extrapolated zero-shear viscosities reported are the average and standard deviation of at least three measurements.

Example 1: Low-Concentration Aqueous Solutions of the Polysaccharide Sodium Alginate Exhibit Non-Newtonian Flow while Aqueous Solutions of Heparin and Dextran Exhibit Newtonian Flow Materials and Methods Commercially-obtained sodium alginate of "low-viscosity" and "medium-viscosity" (Sigma Aldrich #A1112 and #A2033, respectively) were dissolved in MilliQ water with vigorous stirring (1100 RPM) and overnight mixing on a rocking plate shaker to the concentrations indicated below. The pH of the solutions was adjusted to 7.4 with aqueous HCl and/or NaOH. The reported extrapolated zero-shear viscosities were measured on a "B" chip using the mVROC microfluidic viscometer.

Heparin sodium salt, from porcine intestinal mucosa (Alfa Aesar #A16198), and Dextran (Avg molecular weight 150,000, Sigma Aldrich) were similarly prepared in aqueous phosphate buffer (0.18 M) without pH adjustment.

Results

The data in Table 1 demonstrate that the viscosity of a solution of sodium alginate in water increases with increasing polysaccharide concentration. The data in Table 2 demonstrate that, as in the case of sodium alginate, the viscosity of solutions containing Heparin sodium increase with increasing polysaccharide concentration. The representative data in FIG. 1 demonstrate that sodium alginate solutions exhibit markedly non-Newtonian flow while high-concentration Heparin sodium and Dextran solutions (at approximately 300 mg/mL and 200 mg/mL, respectively) exhibit Newtonian flow (the data points incorporate standard deviations which, however, are often smaller than the symbols).

TABLE 1

Viscosities of aqueous solutions of sodium alginate at pH 7.4 and 25° C.

| Polysaccharide | [Sodium alginate] (mg/mL) | Viscosity (cP) |
|---|---|---|
| "Low-viscosity" | 88 | 429 ± 0 |
| sodium alginate | 70 | 193 ± 0 |
| "Medium-viscosity" | 10 | 130 ± 13 |
| sodium alginate | 8.2 | 67.2* |

*Viscosity is result of a single measurement.

TABLE 2

Viscosities of aqueous solutions of Heparin Sodium at 25° C.

| Polysaccharide | [Heparin Sodium] (mg/mL) | Viscosity (cP) |
|---|---|---|
| Heparin Sodium | 740 | 3080 ± 15 |
| | 370 | 112 ± 3 |
| | 244 | 28.3 ± 2.6 |

Example 2: Aqueous Solutions of Heparin Sodium and Dextran Exhibit Reduced Viscosity in the Presence of Viscosity-Lowering Agents Materials and Methods Heparin sodium salt, Dextran, and DEAE-Dextran (diethylaminoethyl dextran) (approximate MW 500,000 Da) were prepared as described in Example 1 above, unless otherwise specified. After homogenous solutions were obtained, the solutions were aliquoted into 80 μL portions. 20 μL of aqueous concentrated viscosity-lowering agent (pH 7, 0.05-1.25 M) was added to each aliquot to afford final concentrations of 0.01-0.25 M agent. Phosphate buffer (pH 7) was used as a control, non-viscosity-lowering excipient. The aliquots were mixed by a positive displacement pipet and placed on a shaker plate for at least 30 minutes. The final concentrations of polysaccharides were about 200 mg/mL and 400 mg/mL (Table 3 and FIG. 2, respectively) for Dextran solutions and about 340 mg/mL for DEAE-dextran solutions (FIG. 3) (EMMC=4-ethyl-4-methylmorpholinium methylcarbonate). To prepare 300 mg/mL Heparin samples (Table 4), the polysaccharide was weighed into 150 mg aliquots and 500 µL of 0.25 M viscosity lowering agent was added with mixing.

Results

Tables 3 and 4 demonstrate the viscosity reducing effect of viscosity-lowering excipients, including a viscosity-lowering agent, with a 200 mg/mL solution of Dextran (Table 3) and a 300 mg/mL solution of Heparin sodium at pH 7 (Table 4). Ammonium sulfate, creatinine and 4-aminpyridine reduce the viscosity of aqueous Dextran solutions by up to 10%. Similarly, Ammonium sulfate and 4-aminopyridine reduce the viscosity of aqueous Heparin sodium solutions by up to 15%. Yellow 5 reduces the viscosity by approximately 10% for solutions of both Dextran and Heparin sodium.

TABLE 3

Viscosity of Aqueous Dextran Solutions Containing Viscosity-lowering Excipients

| Excipient | [Excipient], M | Viscosity, cP |
|---|---|---|
| Phosphate Buffer (control) | 0.18 | 28.9 ± 0.4 |
| Ammonium Sulfate | 0.25 | 27.2 ± 0.1 |
| Creatinine | 0.16 | 26.9 ± 0.1 |
| Yellow 5 | 0.01 | 25.9 ± 0.1 |
| 4-Aminopyridine | 0.13 | 26.0 ± 0.1 |
| Arginine HCl | 0.25 | 29.8 ± 0.4 |
| Sodium Trimetaphosphate | 0.14 | 29.0 ± 0.3 |

TABLE 4

Viscosity of Aqueous Heparin Solutions Containing Viscosity-lowering Excipients

| Excipient | [Excipient], M | Viscosity (cP) |
|---|---|---|
| Phosphate Buffer (control) | 0.25 | 38.6 ± 0.7 |
| Ammonium Sulfate | 0.25 | 34.7 ± 0.2 |
| BMP-Cl * | 0.25 | 37.7 ± 0.2 |
| Yellow 5 | 0.05 | 36.4 ± 0.1 |
| 4-Aminopyridine | 0.25 | 32.6 ± 2.4 |
| Arginine HCl | 0.25 | 42.5 ± 2.2 |

* BMP-Cl = 1-butyl-1-methylpyrrolidinium chloride

Figure 2:
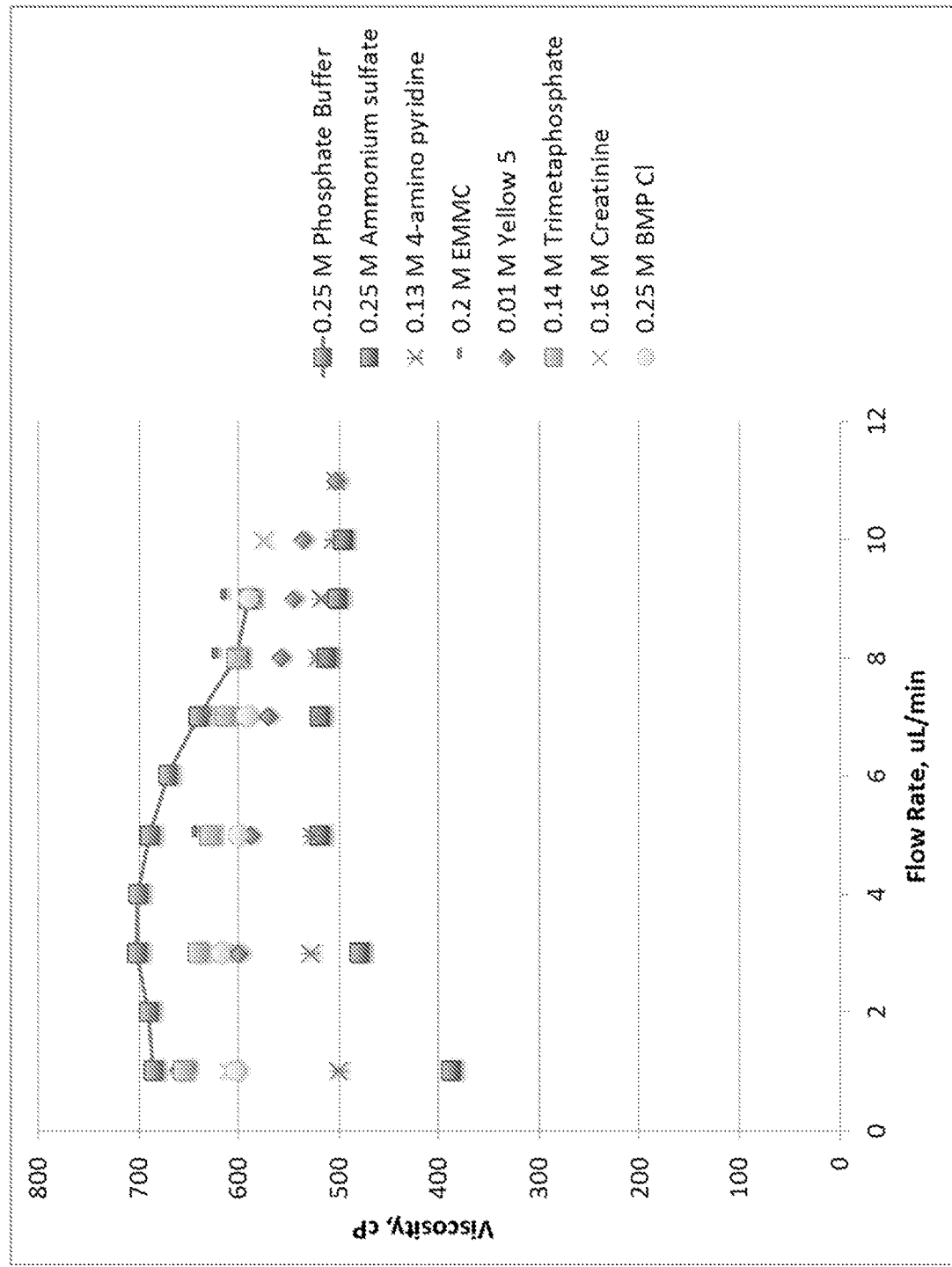
FIG. 2 depicts the viscosity in cP as a function of flow rate for aqueous solutions of Dextran (400 mg/mL) in the presence of various viscosity-lowering excipients.
Figure 3:
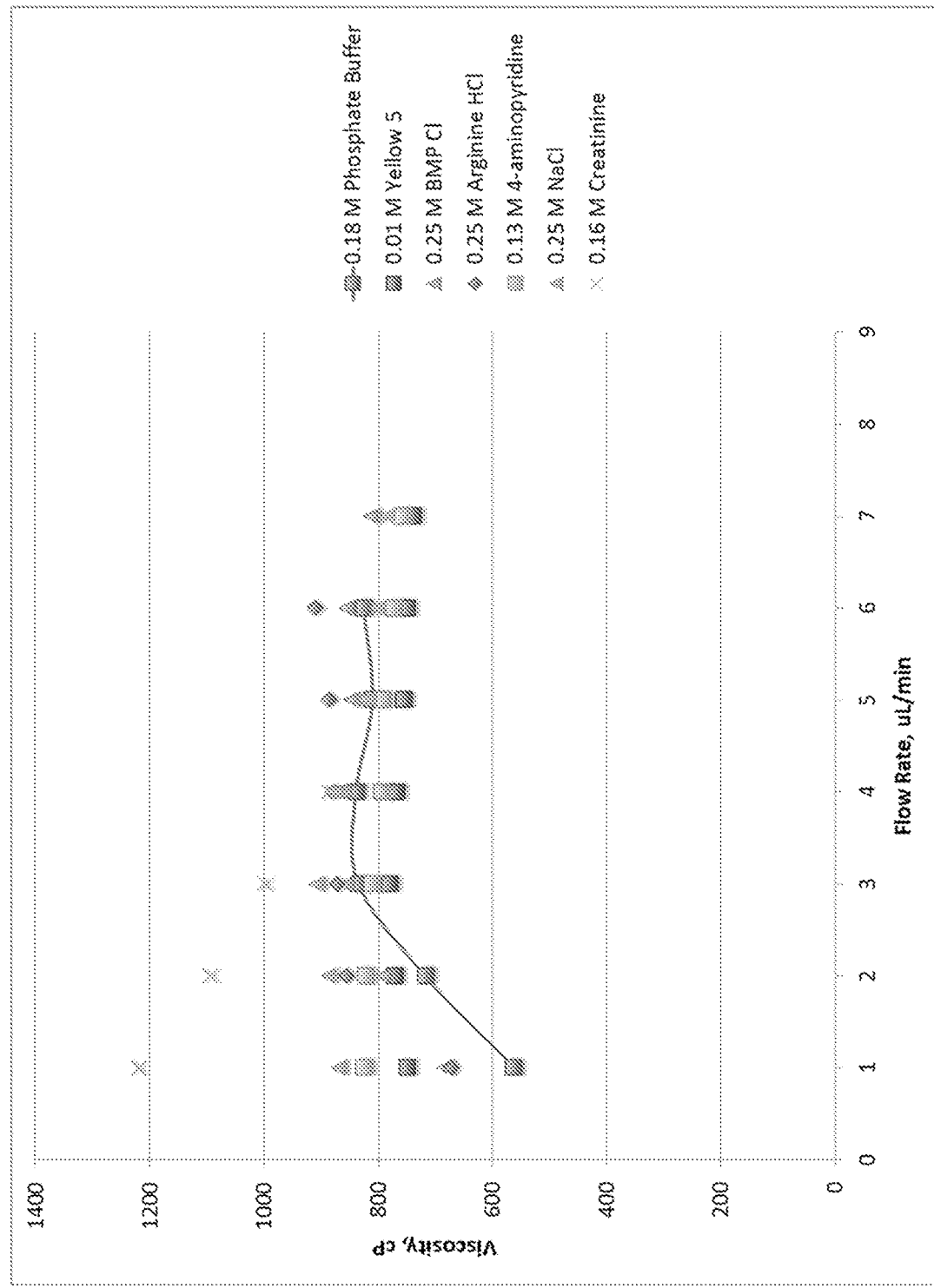
FIG. 3 depicts the viscosity in cP as a function of flow rate for aqueous solutions of DEAE-Dextran (340 mg/mL) in the presence of various viscosity-lowering excipients.

FIGS. 2 and 3 show the viscosity dependence on flow rate for various viscosity-lowering agents tested with the polysaccharides Dextran and DEAE-Dextran, respectively. Some of the samples exhibit shear-thinning behavior, where increased flow rate (i.e. the shear rate) results in decreased fluid viscosity. For both polysaccharides at the highest measured flow rates, solutions containing 4-aminopyridine have viscosity approximately 10% lower than the phosphate buffer control. For Dextran, ammonium sulfate also affords an approximate 10% reduction in viscosity. For Dextran solutions measured at intermediate flow rates, solutions containing EMMC and BMP-Cl had a lower viscosity than the phosphate buffer control; the magnitude of viscosity reduction is about 15% for BMP-Cl and about 10% for EMMC. At intermediate shear rates, solutions containing Dextran and the organophosphate sodium trimetaphosphate have an approximate 10% reduction in viscosity when compared to the phosphate buffer control. Solutions containing yellow 5 also have a lower viscosity than the phosphate buffer control; for Dextran the viscosity is reduced by about 15% and for DEAE-Dextran by about 10%.

EXEMPLARY EMBODIMENTS

The invention is further described by the following embodiments. The features of each of the embodiments are combinable with any of the other embodiments where appropriate and practical.

Embodiment 1

In one embodiment, the invention provides a liquid pharmaceutical formulation for injection comprising:
 (i) one or more polysaccharides and/or nucleic acids;
 (ii) one or more viscosity-lowering agents; and
 (iii) a pharmaceutically acceptable solvent;
wherein when the polysaccharides and/or nucleic acids are combined with the solvent and one or more viscosity-lowering agents in a volume suitable for injection, the formulation has an absolute viscosity from about 1 cP to about 50 cP at 25° C., as measured, for example, using a cone and plate viscometer; and the absolute viscosity of the formulation is lower than the absolute viscosity of an otherwise substantially the same formulation but without the viscosity-lowering agent; and
wherein the absolute viscosity in each case is an extrapolated zero-shear viscosity.

Embodiment 2

The formulation of embodiment 1, wherein the polysaccharide has a molecular weight of between about 0.5 kDa and about 2,000 kDa, and the nucleic acid has a molecular weight of between about 1 kDa and about 5,000 kDa.

Embodiment 3

The formulation of any one of embodiments 1 and 2, wherein the polysaccharide has a molecular weight from about 1 kDa and about 1,000 kDa, preferably from about 2 kDa and about 500 kDa.

Embodiment 4

The formulation of any of embodiments 1-3 wherein the polysaccharide is selected from the group consisting of heparins of different molecular weights and their derivatives, polysaccharide vaccines, hyaluronic acids, dermatan sulfate, chondroitin-4-sulfate, chondroitin-6-sulfate, keratan sulfate, heparan sulfate, curdlan sulfate, cyclodextrins, alginate, chitosan; and the nucleic acid is selected from the group consisting of linear and circular DNA, single-stranded and double-stranded DNA, DNA aptamers, DNAzymes, RNA, RNAi, siRNA, shRNA, miRNA, mRNA, lincRNA, ribozymes, morpholinos, and combinations thereof.

Embodiment 5

The formulation of any one of embodiments 1-4, wherein the polysaccharides or nucleic acids are present in a combined amount from about 100 mg to about 2,000 mg per 1 mL (mg/mL); optionally greater than about 150 mg/mL.

Embodiment 6

The formulation of any one of embodiments 1-5, wherein the formulation comprises at least two different polysaccharides, preferably wherein both of the polysaccharides have a molecular weight of at least about 50 kDa.

Embodiment 7

The formulation of any one of embodiments 1-6, wherein the initial absolute viscosity at the same polysaccharide or nucleic acid concentration prior to adding a viscosity-lowering agent exceeds about 60 cP, exceeds about 80 cP, or exceeds about 100 cP.

Embodiment 8

The formulation of any one of embodiments 1-7, wherein the liquid formulation is aqueous having a pH between about 4.0 and about 8.0.

Embodiment 9

The formulation of any one of embodiments 1-8, wherein the viscosity-lowering agent is present at a concentration from about 0.01 M to about 1.0 M.

Embodiment 10

The formulation of any one of embodiments 1-9, wherein the viscosity-lowering agent is present at a concentration of less than about 0.15 M or less than about 0.10 M.

Embodiment 11

The formulation of any one of embodiments 1-10 comprising one or more pharmaceutically acceptable excipients for subcutaneous (SC) or intramuscular (IM) injection selected from the group consisting of sugars or sugar alcohols, buffering agents, preservatives, carriers, antioxidants, chelating agents, natural or synthetic polymers, cryoprotectants, lyoprotectants, surfactants, bulking agents, and stabilizing agents.

Embodiment 12

The formulation of embodiment 11, wherein the one or more excipients are selected from the group consisting of polysorbates, poloxamer 188, sodium lauryl sulfate, polyol selected from the group consisting of sugar alcohols such as mannitol and sorbitol, poly(ethylene glycols), glycerol, propylene glycols, and poly(vinyl alcohols).

Embodiment 13

The formulation of embodiment 11, wherein the surfactant is present in a concentration less than about 10 mg/mL.

Embodiment 14

The formulation of embodiment 12, comprising a polyol present in a concentration from about 2 mg/mL to about 900 mg/mL.

Embodiment 15

The formulation of any one of embodiments 1-14, wherein the absolute viscosity is from about 5 cP to about 50 cP at 25° C.

Embodiment 16

The formulation of any one of embodiments 1-15, wherein the absolute viscosity is at least about 30% lower than the absolute viscosity of a formulation without the viscosity-lowering agent when measured under the same conditions except for replacement of the viscosity-lowering agent with an appropriate buffer at about the same concentration.

Embodiment 17

The formulation of any one of embodiments 1-16, wherein the absolute viscosity is at least about 2-fold or about 4-fold less than the absolute viscosity of a formulation without the viscosity-lowering agent when measured under the same conditions except for replacement of the viscosity-lowering agent with an appropriate buffer at about the same concentration.

Embodiment 18

The formulation of any one of embodiments 1-17 in a unit-dose vial, container, or pre-filled syringe.

Embodiment 19

The formulation of embodiment 18 wherein the polysaccharide or nucleic acid, the viscosity-lowering agent and/or excipients are in dry form, preferably lyophilized.

Embodiment 20

The formulation of any of embodiments 1-19, wherein the volume of the formulation when the viscosity-lowering agent, polysaccharide or nucleic acid, and solvent are combined is less than about 1.5 mL for SC injections, and less than about 3 mL for IM injections.

Embodiment 21

The formulation of any one of embodiments 1-20, wherein the formulation is isotonic to human blood serum.

Embodiment 22

The formulation of any one of embodiments 1-21 which behaves rheologically essentially as a Newtonian liquid at conditions under which it would be administered to a person in need thereof.

Embodiment 23

The formulation of any one of embodiments 1-22 achieving a therapeutically effective dosage as compared to the same dose of the polysaccharide or nucleic acid administered by intravenous infusion.

Embodiment 24

The formulation of any one of embodiments 1-23 wherein the viscosity-lowering agent is present at a concentration that causes no significant signs of toxicity or injection site irritation when administered via SC or IM injection.

Embodiment 25

The formulation of any of embodiments 1-24, wherein the absolute viscosity of the formulation is measured at a shear rate at least about $0.5$ $s^{-1}$, when measured using a cone and plate viscometer.

Embodiment 26

The formulation of any of embodiments 1-24, wherein the absolute viscosity of the formulation is measured at a shear rate at least about 1.0 s$^{-1}$, when measured using a microfluidic viscometer.

Embodiment 27

In one embodiment, the invention provides a method of administering a therapeutically effective amount of a polysaccharide or nucleic acid comprising SC or IM injections of the formulation of any one of embodiments 1-26.

Embodiment 28

The method of embodiment 27, wherein the SC or IM injections are performed with a syringe selected from the group consisting of heated syringes, self-mixing syringes, auto-injectors, pre-filled syringes, and combinations thereof.

Embodiment 29

The method of embodiment 28, wherein the syringe is a heated syringe and the formulation is administered at a temperature between 25° C. and 40° C.

Embodiment 30

The method of any one of embodiments 27-29, wherein the formulation produces a primary irritation index of less than 3 when evaluated using a Draize scoring system.

Embodiment 31

The method of any one of embodiments 27-30, wherein the injection force is at least 10% or 20% less than the injection force for the otherwise same formulation without the viscosity-lowering agent administered in the same way.

Embodiment 32

The method of any one of embodiments 27-31, wherein the injection is administered with a needle between 27 and 31 gauge in diameter and the injection force is less than 30 N with the 27 gauge needle.

Embodiment 33

In one embodiment, the invention provides a method of preparing a pharmaceutical formulation comprising the step of combining the polysaccharide and/or nucleic acid, the solvent, and the viscosity-lowering agent of any of embodiments 1-26.

Embodiment 34

The method of embodiment 33, wherein the formulation is in a pre-filled syringe or cartridge.

Embodiment 35

In one embodiment, the invention provides a method of facilitating purification of a polysaccharide or nucleic acid comprising adding to a polysaccharide and/or nucleic acid solution an effective amount of the viscosity-lowering agent of any of embodiments 1 or 7-10 to reduce the viscosity of the polysaccharide and/or nucleic acid solution.

Embodiment 36

The method of embodiment 35 wherein the polysaccharide and/or nucleic acid-viscosity-lowering agent solution is purified or concentrated using a method selected from the group consisting of ultrafiltration/diafiltration, tangential flow filtration, centrifugal concentration, and dialysis.

Embodiment 37

In one embodiment, the invention provides a method of preparing a polysaccharide or nucleic acid, comprising fermenting an appropriate organism in the presence of the viscosity-lowering agent of any of embodiments 1 or 7-10 in an amount sufficient to maintain a low viscosity of the fermentation mixture.

All references throughout, such as publications, patents, patent applications, and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

Unless expressly defined otherwise above, all technical and scientific terms used herein have the same meanings as commonly understood by one of skill in the art. Those skilled in the art will recognize, or will be able to ascertain using no more than routine experimentation, many equivalents to the specific embodiments of the invention described herein. Such equivalents are intended to be encompassed by the following claims.

We claim:

1. A liquid pharmaceutical formulation for subcutaneous or intramuscular injection comprising
    (i) heparin or dextran;
    (ii) a viscosity-lowering agent, wherein the viscosity-lowering agent comprises:
        Yellow 5 or a pharmaceutically acceptable salt thereof,
        4-aminopyridine or a pharmaceutically acceptable salt thereof,
        1-butyl-1-methylpyrrolidinium chloride (BMP-Cl) or a pharmaceutically acceptable salt thereof, or
        any combination thereof; and
    (iii) a pharmaceutically acceptable solvent;
    wherein the liquid pharmaceutical formulation, when in a volume suitable for subcutaneous or intramuscular injection, has an absolute viscosity of from about 1 cP to about 50 cP at 25° C., as measured using a cone and plate viscometer or a microfluidic viscometer;
    wherein the absolute viscosity is an extrapolated zero-shear viscosity.

2. The liquid pharmaceutical formulation of claim 1, wherein the liquid formulation is aqueous.

3. The liquid pharmaceutical formulation of claim 1, wherein the viscosity-lowering agent is present at a concentration of from about 0.01 M to about 1.0 M.

4. The liquid pharmaceutical formulation of claim 1, further comprising one or more pharmaceutically acceptable excipients comprising a sugar, a sugar alcohol, a buffering agent, a preservative, a carrier, an antioxidant, a chelating agent, a natural polymer, a synthetic polymer, a cryoprotectant, a lyoprotectant, a surfactant, a bulking agent, a stabilizing agent, or any combination thereof.

5. The liquid pharmaceutical formulation of claim 4, wherein the one or more pharmaceutically acceptable excipients is a polysorbate, a poloxamer 188, a sodium lauryl sulfate, a polyol, a poly(ethylene glycol), a glycerol, a propylene glycol, and/or a poly(vinyl alcohol).

6. The liquid pharmaceutical formulation of claim 4, wherein the sugar alcohol is sorbitol or mannitol.

7. The liquid pharmaceutical formulation of claim 1 in a unit-dose vial, multi-dose vial, cartridge, or pre-filled syringe.

8. The liquid pharmaceutical formulation of claim 1, wherein the liquid pharmaceutical formulation is reconstituted from a lyophilized composition.

9. The liquid pharmaceutical formulation of claim 1, wherein the liquid pharmaceutical formulation is isotonic to human blood serum.

10. The liquid pharmaceutical formulation of claim 1, wherein the absolute viscosity of the liquid pharmaceutical formulation is measured at a shear rate of at least about 0.5 $s^{-1}$ when measured using a cone and plate viscometer.

11. The liquid pharmaceutical formulation of claim 1, wherein the absolute viscosity of the liquid pharmaceutical formulation is measured at a shear rate of at least about 1.0 $s^{-1}$ when measured using a microfluidic viscometer.

12. A method of preparing the liquid pharmaceutical formulation of claim 1 comprising the step of combining the heparin or the dextran, the pharmaceutically acceptable solvent, and the one or more viscosity-lowering agents to thereby prepare the liquid pharmaceutical formulation.

13. The liquid pharmaceutical formulation of claim 1, wherein the liquid pharmaceutical formulation comprises the heparin.

14. The liquid pharmaceutical formulation of claim 1, wherein the liquid pharmaceutical formulation comprises the dextran.

15. The liquid pharmaceutical formulation of claim 1, wherein the viscosity-lowering agent comprises the Yellow 5 or a pharmaceutically acceptable salt thereof.

16. The liquid pharmaceutical formulation of claim 1, wherein the viscosity-lowering agent comprises the 4-aminopyridine or a pharmaceutically acceptable salt thereof.

17. The liquid pharmaceutical formulation of claim 1, wherein the viscosity-lowering agent comprises the BMP-Cl or a pharmaceutically acceptable salt thereof.

18. A method of administering to a subject a therapeutically effective amount of the heparin or the dextran, comprising subcutaneously or intramuscularly injecting the liquid pharmaceutical formulation of claim 1 into the subject to thereby administer the heparin or the dextran.

19. The method of claim 18, wherein the injecting is performed with a syringe.

20. The method of claim 19, wherein the syringe is a heated syringe and the formulation is administered at a temperature between 25° C. and 40° C.

21. The method of claim 19, wherein the syringe is a heated syringe, a self-mixing syringe, an auto-injector, a pre-filled syringe, or combinations thereof.

22. The method of claim 18, wherein the formulation produces a primary irritation index less than 3 when evaluated using a Draize scoring system.

23. The method of claim 18, wherein the injection force is at least 10% less than the injection force for a control formulation comprising the heparin or the dextran and the pharmaceutically acceptable solvent but without the viscosity-lowering agent.

24. The method claim 23, wherein the injection force is 20% less than the injection force of the control formulation.

25. The method of claim 18, wherein the injecting is performed with a needle between 27 and 31 gauge in diameter and the injection force is less than 30 N with the 27 gauge needle.

26. A lyophilized composition comprising:
(i) dextran or heparin;
(ii) one or more viscosity-lowering agents; wherein the one or more viscosity-lowering agents comprise:
Yellow 5 or a pharmaceutically acceptable salt thereof,
4-aminopyridine or a pharmaceutically acceptable salt thereof,
BMP-Cl or a pharmaceutically acceptable salt thereof, or any combination thereof; and
(iii) a pharmaceutically acceptable solvent.

27. The lyophilized composition of claim 26, wherein, once reconstituted, the dextran or the heparin have a concentration of at least 200 mg/ml.

28. The lyophilized composition of claim 26, wherein the lyophilized composition comprises heparin.

29. The lyophilized composition of claim 26, wherein the lyophilized composition comprises dextran.

30. The lyophilized composition of claim 26, wherein the viscosity-lowering agent comprises Yellow 5 or a pharmaceutically acceptable salt thereof.

31. The lyophilized composition of claim 26, wherein the viscosity-lowering agent comprises 4-aminopyridine or a pharmaceutically acceptable salt thereof.

32. The lyophilized composition of claim 26, wherein the viscosity-lowering agent comprises BMP-Cl or a pharmaceutically acceptable salt thereof.

* * * * *